United States Patent
Le Marié et al.

(10) Patent No.: US 12,121,603 B1
(45) Date of Patent: Oct. 22, 2024

(54) SKIN BARRIER PROTECTIVE DELIVERY SYSTEMS

(71) Applicant: BOBO LABS INC., New York, NY (US)

(72) Inventors: Edouard Le Marié, Antibes (FR); Bénédicte Le Marié, Antibes (FR); Lyndon Garcines, Fountain Valley, CA (US); Adriel Carolino, Huntington Beach, CA (US); Felipe Jimenez, Rialto, CA (US)

(73) Assignee: BOBO LABS INC., New York, NY (US)

( * ) Notice: Subject to any disclaimer, the term of this patent is extended or adjusted under 35 U.S.C. 154(b) by 0 days.

(21) Appl. No.: 18/703,841

(22) PCT Filed: Apr. 21, 2023

(86) PCT No.: PCT/US2023/019431
§ 371 (c)(1),
(2) Date: Apr. 23, 2024

(87) PCT Pub. No.: WO2023/205439
PCT Pub. Date: Oct. 26, 2023

Related U.S. Application Data

(60) Provisional application No. 63/434,179, filed on Dec. 21, 2022, provisional application No. 63/333,768, filed on Apr. 22, 2022.

(51) Int. Cl.
| | |
|---|---|
| *A61K 8/31* | (2006.01) |
| *A61K 8/04* | (2006.01) |
| *A61K 8/37* | (2006.01) |
| *A61K 8/92* | (2006.01) |
| *A61Q 17/00* | (2006.01) |

(52) U.S. Cl.
CPC ............. *A61K 8/31* (2013.01); *A61K 8/046* (2013.01); *A61K 8/37* (2013.01); *A61K 8/922* (2013.01); *A61Q 17/00* (2013.01)

(58) Field of Classification Search
CPC . A61K 8/31; A61K 8/046; A61K 8/37; A61K 8/922; A61Q 17/00
See application file for complete search history.

(56) References Cited

U.S. PATENT DOCUMENTS

| | | | |
|---|---|---|---|
| 6,261,575 | B1 | 8/2001 | Hoppe et al. |
| 9,289,373 | B2 | 3/2016 | Brown et al. |
| 9,351,911 | B1 | 5/2016 | Sweeney et al. |
| 9,499,419 | B2 | 11/2016 | De Rijk |
| 9,566,218 | B2 | 2/2017 | Matsumoto et al. |
| 2002/0006420 | A1 | 1/2002 | Philippe et al. |
| 2006/0165739 | A1 | 7/2006 | Kornesvarakul et al. |
| 2010/0221195 | A1 | 9/2010 | Tamarkin et al. |
| 2011/0044920 | A1 | 2/2011 | Hines et al. |
| 2012/0027702 | A1 | 2/2012 | Bernoud et al. |
| 2012/0258059 | A1 | 11/2012 | Iwama et al. |
| 2017/0143610 | A1 | 5/2017 | Bernoud et al. |
| 2018/0256479 | A1 | 9/2018 | Bernoud et al. |
| 2019/0343753 | A1 | 11/2019 | Bernoud et al. |
| 2021/0154110 | A1 | 5/2021 | Bernoud |

FOREIGN PATENT DOCUMENTS

WO   0062744 A2   10/2000

OTHER PUBLICATIONS

International Search Report and Written Opinion for Corresponding International Application No. PCT/US2023/019431, dated Oct. 2, 2023. 18 pages.
"Savan Skincare Lightweight Moisterizer", INCIDecoder, Mar. 15, 2021, incidecoder.com/products/savan-skincare-lightweight-moisterizer. 12 pages.

*Primary Examiner* — Robert A Wax
*Assistant Examiner* — Quanglong N Truong
(74) *Attorney, Agent, or Firm* — Leason Ellis LLP

(57) ABSTRACT

The present disclosure relates to compositions and methods for the treatment of topical skin conditions. Also provided are topically applied compositions and delivery systems. Also provided are methods of using the compositions and delivery systems in cosmetic, personal care and dermatology applications. Also provided is a sprayable composition that comprises petrolatum.

3 Claims, No Drawings

SKIN BARRIER PROTECTIVE DELIVERY SYSTEMS

CROSS-REFERENCE TO RELATED PATENT APPLICATIONS

This application is a U.S. National Stage Application under 35 U.S.C. § 371 of International Patent Application No. PCT/US2023/019431 filed Apr. 21, 2023, which claims the benefit of priority of U.S. Provisional Application No. 63/333,768 filed Apr. 22, 2022, and U.S. Provisional Application No. 63/434,179, filed Dec. 21, 2022, each of which are incorporated by reference in their entireties. The International Application was published on Oct. 26, 2023, as International Publication No. WO/2023/205439.

1. CROSS REFERENCE

This application claims the benefit of U.S. Provisional Application No. 63/333,768, filed Apr. 22, 2022, and U.S. Provisional Application No. 63/434,179, filed Dec. 21, 2022, the content of each of which is incorporated herein by reference in its entirety.

2. FIELD

The present disclosure relates to compositions and methods for the treatment of topical skin conditions. Also provided are topically applied compositions and delivery systems. Further provided are methods of using the compositions and delivery systems in cosmetic, personal care and dermatology applications. Also provided is a composition in the form of a sprayable gel.

3. BACKGROUND

The skin is the largest organ of the body and protects mammalian organisms from both aqueous and xerotic ambient environments. It is now generally accepted that the intercellular, lamellar bilayer sheets of stratum corneum lipids are the key constituents for a functional barrier. The maintenance of a barrier against excessive transcutaneous water loss to the environment is critical to survival of all terrestrial animals. Localized or generalized perturbations of the epidermal barrier occur in a variety of diseases and conditions of the skin and mucous membrane. These perturbations not only contribute significantly to the morphology of the cutaneous lesions, but also activate certain skin diseases.

Active agents are used in skin treatments of various and diverse dermatological conditions such as psoriasis, photoaging, age spots, aged appearance of the skin due to extrinsic and intrinsic causes, skin wrinkles, acne, hyperpigmentation and skin cancers. Active agents typically are prescription active agents and non-prescription active agents. Solvents used in dermatological formulations having skin treatment active agents may be strong solvents, such as acetone, or mild, i.e., gentle, solvents. However, strong solvents are known to cause skin condition effects that require additional treatment including disruption of the skin barrier and may interfere with patients' compliance with skin treatment regimens. Mild solvents, on the other hand, are known to be ineffective in delivery of active agents in transdermal and cutaneous uses. Furthermore, with present tendency toward extended use of dermatological formulations in skincare, there is a continued need for topical formulations of active agents for various skin treatments.

Common moisturizers and emollients also cause disruptions of the barrier function. There has been and remains a need for cosmetically elegant, non-unctuous, safe and effective topical compositions that not only protects the skin barrier but also effectively and safely delivers other functional and/or pharmaceutically active ingredients to the skin.

4. SUMMARY

One of the objectives of the present disclosure is to provide a cost effective composition, such as a smooth and non-sticky sprayable composition that is easy to apply and hygienic. In one embodiment, the present composition increases water retention and improves skin roughness (moisturization), repairs and protects the skin from harmful conditions.

Certain skincare formulations disclosed herein provide surprising, unexpected results. In certain embodiments, the disclosed delivery system comprises certain components that provide additive or synergistic results.

Provided in the present disclosure are compositions that are useful as skin moisturizers, skin softening agents, skin debridement agents, etc., as well as base composition for cosmetic formulations, compositions for therapeutics, e.g., pharmacological, formulations. In cosmetic formulations, the compositions can be used with added ingredients that are solely cosmetic. Alternatively, the cosmetic formulation can include ingredients that are both cosmetically efficacious and therapeutically effective, e.g., "cosmeceutical" ingredients.

In one embodiment, disclosed herein is a composition that corrects defective epidermal barrier in a skin or mucous membrane disease or condition. The compositions and methods disclosed fortify the barrier to prevent its disruption due to environmental insults. The disclosed composition is useful as moisturizers for emolliation and hydration of the epidermis and produces a neutral effect on barrier function, and in certain cases improves barrier function or enhance its recovery rate.

The disclosed composition also enhances the therapeutic activity of other pharmaceutical agents. Such agents include anti-inflammatory agents, antimicrobial agents, antineoplastic agents, antipruritic agents, antihistamines, analgesic agents, natural and synthetic vitamin analogs, carboxylic acids and their analogs, and artemisinin and its analogs.

By virtue of their effect on epidermal barrier function, the disclosed composition ameliorates epidermal hyperproliferation and diminishes inflammation. This results in significant prolonged or complete remission and prevents recurrences of skin disorders.

In certain embodiments, the skin barrier protective delivery system comprises a sprayable petrolatum that holds a higher concentration of an active ingredient without separation. It has unexpectedly been discovered that a composition comprising at least about 30% petrolatum by weight can be formulated as a spray. It has further been unexpectedly discovered that a formulation with such a high concentration of petrolatum as in the present disclosure is capable of being sprayed easily and efficiently providing even coverage on the skin. In certain embodiments, the sprayable formulation does not contain propellant gases as additives which may be harmful to the subject. In one embodiment, the composition forms an occlusive film on the skin.

In some embodiments, provided herein is a skin barrier protective delivery system of comprising (i) a mixture of Coconut Alkanes at a concentration range of 30-70 wt % and Coco-Caprylate/Caprate at a concentration range of 3-7 wt %; and (ii) petrolatum, wherein the petrolatum is present at a concentration of at least 30 wt %; wherein the delivery system is sprayable. In some embodiments, the petrolatum is present at a concentration of 40 wt %. In some embodiments, the petrolatum is present at a concentration of 50 wt %.

In some embodiments, a skin barrier protective delivery system comprises (i) a mixture of Coconut Alkanes at a concentration range of 30-65 wt % and Coco-Caprylate/Caprate at a concentration range of 3-7 wt %; and (ii) petrolatum, wherein the petrolatum is present at a concentration of at least 30 wt %, wherein the delivery system is sprayable. In some embodiments, the petrolatum is present at a concentration of 40 wt %. In some embodiments, the petrolatum is present at a concentration of 50 wt %.

In some embodiments, a skin barrier protective delivery system comprises (i) a mixture of Coconut Alkanes at a concentration range of 30-70 wt % and Coco-Caprylate/Caprate at a concentration range of 3-7 wt %, wherein the combined concentration of Coconut Alkanes and Coco-Caprylate/Caprate is at most 70 wt %; and (ii) petrolatum, wherein the petrolatum is present at a concentration of at least 30 wt %, wherein the delivery system is sprayable. In some embodiments, the petrolatum is present at a concentration of 40 wt %. In some embodiments, the petrolatum is present at a concentration of 50 wt %.

In some embodiments, provided herein is a skin barrier protective delivery system of comprising (i) a mixture of Coconut Alkanes at a concentration range of 30-70 wt % and Coco-Caprylate/Caprate at a concentration range of 3-7 wt %; and (ii) petrolatum, wherein the petrolatum is present at a concentration of 25-60 wt %; wherein the delivery system is sprayable. In some embodiments, the petrolatum is present at a concentration of 40 wt %. some embodiments, the petrolatum is present at a concentration of 50 wt %.

In some embodiments, provided herein is a skin barrier protective delivery system of comprising (i) a mixture of Coconut Alkanes at a concentration range of 30-65 wt % and Coco-Caprylate/Caprate at a concentration range of 3-7 wt %; and (ii) petrolatum, wherein the petrolatum is present at a concentration of 25-60 wt %; wherein the delivery system is sprayable. In some embodiments, the petrolatum is present at a concentration of 40 wt %. some embodiments, the petrolatum is present at a concentration of 50 wt %.

In some embodiments, a skin barrier protective delivery system comprises (i) a mixture of Coconut Alkanes at a concentration range of 30-70 wt % and Coco-Caprylate/Caprate at a concentration range of 3-7 wt %, wherein the combined concentration of Coconut Alkanes and Coco-Caprylate/Caprate is at most 70 wt %; and (ii) petrolatum, wherein the petrolatum is present at a concentration of 25-60 wt %, wherein the delivery system is sprayable. In some embodiments, the petrolatum is present at a concentration of 40 wt %. some embodiments, the petrolatum is present at a concentration of 50 wt %.

In some embodiments, the skin barrier protective delivery system of the present disclosure contains at least one, at least two, at least three, or at least four of ceramide, a triglyceride, a phytosterol, a phytosterol ester, a terpene (e.g., squalene), a plant-based ester or wax, tocopherol and/or a phospholipid. In some embodiments, the petrolatum is present at a concentration of 25-60 wt %. In some embodiments, the petrolatum is present at a concentration of at least 30 wt %. In some embodiments, the petrolatum is present at a concentration of 40 wt %. some embodiments, the petrolatum is present at a concentration of 50 wt %.

In some embodiments, the skin barrier protective delivery system of the present disclosure contains a plant-based ester or wax. In some embodiments, the plant-based ester or wax is selected from the group consisting of jojoba oils, jojoba esters, candelilla wax, carnauba wax, rice bran wax and sunflower wax. In some embodiments, the plant-based ester or wax comprises jojoba esters.

In some embodiments, the skin barrier protective delivery system of the present disclosure comprises a terpene. In some embodiments, the terpene is selected from the group consisting of a triterpene, a hemiterpene, a monoterpene, a sesquiterpene, a diterpene, a sesterterpene and a tetraterpene. In some embodiments, the terpene is a triterpene, for example squalene.

In some embodiments, the skin barrier protective delivery system of the present disclosure comprises a phytosterol ester comprising esters derived from a seed or nut oil. In some embodiments, the seed or nut oil is selected from the group consisting of macadamia oil, almond oil, avocado oil, canola oil, coconut oil, corn oil, cottonseed oil, grapeseed oil, hazelnut oil, palm oil peanut oil, pine seed oil, pecan oil pumpkin seed oil, safflower oil, sesame oil, soy oil, sunflower oil, and walnut oil. In some embodiments, the phytosterol ester is phytosteryl macadamiate.

In some embodiments, the skin barrier protective delivery system of the present disclosure comprises a ceramide, a triglyceride, a phytosterol, phytosterol macadamiate, squalene, jojoba esters, and tocopherol. In some embodiments, the skin barrier protective delivery system comprises a ceramide NP, ceramide AP, jojoba esters, squalene, phytosterols, phytosteryl macadamiate, tocopherol, a C18-C36 acid triglyceride, and a C12-18 acid triglyceride.

In some embodiments, the skin barrier protective delivery system of the present disclosure comprises at least one of a polysaccharide, a gum, a buffering agent (e.g., an acid), and a plant extract (e.g., a root plant extract).

In some embodiments, skin barrier protective delivery system of the present disclosure comprises a polysaccharide. In some embodiments, the polysaccharide is selected from the group consisting of maltodextrin, cellulose, hydroxyethylcellulose, hydroxypropylcellulose, carboxymethylcellulose, starch, hydrolyzed starch, partially hydrolyzed starch, xylans, inulin, cellobiose, scleroglucan, chitosan, ulvan, fucoidan, alginate, pectin, heparin, hyaluronic acid, and mixtures thereof. In some embodiments, the polysaccharide is maltodextrin.

In some embodiments, the skin barrier protective delivery system of the present disclosure comprises a gum. In some embodiments, the gum is selected from the group consisting of guar gums, xanthan gums, pullulan gums, agar-agar gums, carrageenan gums, gellan gums, gum arables, and tragacanth gums. In some embodiments, the gum is *Acacia senegal* gum.

In some embodiments, the skin barrier protective delivery system of the present disclosure comprises an extract derived from a plant. In some embodiments, the extract is derived from a root plant. In some embodiments, the root plant is selected from the group consisting of sweet potato, potato, beet, carrot, parsnip, horseradish and radish. In some embodiments, the root plant extract is *Ipomoea batatas* root extract.

In some embodiments, the skin barrier protective delivery system of the present disclosure comprises a buffering agent. In some embodiments, the buffering agent is an acid. In some embodiments, the acid is citric acid. In some embodiments, the acid is lactic acid.

In some embodiments, the skin barrier protective delivery system of the present disclosure comprises at least one of *Ipomoea batatas* root extract, citric acid, *Acacia senegal* gum, and maltodextrin. In some embodiments, the skin barrier protective delivery system of the present disclosure comprises *Ipomoea batatas* root extract, citric acid, *Acacia senegal* gum, and maltodextrin.

In some embodiments, the skin barrier protective delivery system of the present disclosure comprises ceramide NP, ceramide AP, jojoba esters, squalene, phytosterols, phytosteryl macadamiate, tocopherol, C18-C36 acid triglyceride, C12-18 acid triglyceride, *Ipomoea batatas* root extract, *Acacia senegal* gum, citric acid, and maltodextrin.

In some embodiments, the skin barrier protective delivery system of the present disclosure comprises (i) at least 30 wt % Petrolatum; (ii) Coconut Alkanes in the range of 30-70 wt %; (iii) Coco-Caprylate/Caprate in the range of 3-7 wt %; (iv) ceramide NP in the range of 0.01-0.1 wt %; (v) ceramide AP in the range of 0.01-0.1 wt %; (vi) Jojoba Esters in the range of 0.1-1.5 wt %; (vii) Squalene in the range of 0.1-1 wt %; (viii) Phytosteryl Macadamiate in the range of 0.01-0.1 wt %; (ix) Phytosterols in the range of 0.005-0.1 wt %; (x) Tocopherol in the range of 0.001-0.1 wt %; (xi) C18-36 Acid Triglyceride in the range of 0.5-5 wt %; (xii) C12-18 Acid Triglyceride in the range of 0.1-1 wt %; (xiii) *Ipomoea batatas* root extract in the range of 0.01-0.1 wt %; (xiv) citric acid in the range of 0.001-0.01 wt %; (xv) *Acacia senegal* gum in the range of 0.001-0.1 wt %; and (xvi) Maltodextrin in the range of 0.001-0.1 wt %. In some embodiments, the delivery system is a sprayable formulation. In some embodiments, the petrolatum is present at a concentration of 40 wt %. In some embodiments, the petrolatum is present at a concentration of 50 wt %.

In some embodiments, the skin barrier protective delivery system of the present disclosure comprises (i) 50 wt % Petrolatum; (ii) 42-43 wt % Coconut Alkanes; (iii) 4-5 wt % Coco-Caprylate/Caprate; (iv) 0.05 wt % ceramide NP; (v) 0.05 wt % ceramide AP; (vi) 0.75 wt % Jojoba Esters; (vii) 0.3-0.4 wt % Squalene; (viii) 0.05-0.06 wt % Phytosteryl Macadamiate; (ix) 0.01-0.02 wt % Phytosterols; (x) 0.0045 wt % Tocopherol; (xi) 1-2 wt % C18-36 Acid Triglyceride; (xii) 0.4-0.5 wt % C12-18 Acid Triglyceride; (xiii) 0.03-0.04 wt % *Ipomoea batatas* root extract; (xiv) 0.003-0.004 wt % citric acid; (xv) 0.03-0.04 wt % *Acacia senegal* gum; and (xvi) 0.03-0.04 wt % Maltodextrin. In some embodiments, the delivery system is a sprayable formulation.

In some embodiments, the skin barrier protective delivery system of the present disclosure further comprises zinc oxide. In some embodiments, the zinc oxide is present in a concentration range of about 10 wt % to about 15 wt %. In some embodiments, the zinc oxide is present in a concentration range of about 10% to about 25%. In some embodiments, the zinc oxide is about 15%.

In some embodiments, the skin barrier protective delivery system of the present disclosure comprises (i) 25-60 wt % Petrolatum; (ii) 10-25 wt % zinc oxide (ZnO); and (iii) 30-60 wt % Isohexadecane.

In some embodiments, the skin barrier protective delivery system of the present disclosure comprises (i) 40 wt % Petrolatum; (ii) 15 wt % zinc oxide (ZnO); and (iii) 45 wt % Isohexadecane.

In some embodiments, the skin barrier protective delivery system of the present disclosure has a viscosity of from about 500 cps to about 10,000 cps, for example from about 1,000 cps to about 5,000 cps.

In some embodiments, the skin barrier protective delivery system of the present disclosure further comprises an active ingredient as described herein. In some embodiments, the active ingredient is present in an amount of from about 0.0001% to about 35% by weight.

In some embodiments, the skin barrier protective delivery system of the present disclosure further comprises a pharmaceutically acceptable carrier or excipient. In some embodiments, the pharmaceutically acceptable carrier or excipient is selected from the group consisting of water and oil emulsions, suspensions, colloids, microemulsions, clear solutions, suspensions of nanoparticles, emulsions of nanoparticles, and anhydrous compositions.

In some embodiments, the present disclosure provides a pharmaceutical composition in the form of a spray, comprising the skin barrier protective delivery system as described herein. In some embodiments, the composition does not comprise a propellant.

In some embodiments, the present disclosure provides pharmaceutical composition in the form of a sprayable gel, comprising the skin barrier protective delivery system of the present disclosure. In some embodiments, the composition does not comprise a propellant, aerosol or bag-on-valve.

In some embodiments, the compositions of the present disclosure do not contain a flammable component. In some embodiments, the compositions of the present disclosure are free of a flammable solubilizer. In some embodiments, the compositions of the present disclosure are free of an alcohol.

In some embodiments, the present disclosure provides a device comprising the skin barrier protective delivery system of the present disclosure.

In some embodiments, the present disclosure provides a device comprising a pharmaceutical composition, the pharmaceutical composition comprising the skin barrier protective delivery system of the present disclosure.

In some embodiments, the device does not comprise a propellant or aerosol or bag-on-valve. In some embodiments, the device is in the form of an atomizer pump. In some embodiments, the device is a dip tube atomizer pump.

In some embodiments, the present disclosure provides a skin barrier protective delivery system comprising: (i) a mixture of long chain Alkanes having a carbon length greater than 10 carbons at a concentration range of 30-70 wt %; and (ii) petrolatum, wherein the petrolatum is present at a concentration of at least 30 wt %, wherein the delivery system is sprayable.

In some embodiments, the present disclosure provides a skin barrier protective delivery system comprising (i) a mixture of long chain Alkanes having a carbon length greater than 10 carbons at a concentration range of 30-70 wt % and esters of long chain alcohols at a concentration of 3-7 wt %; and (ii) petrolatum, wherein the petrolatum is present at a concentration of at least 30 wt %, wherein the delivery system is sprayable.

5. DETAILED DESCRIPTION

Disclosed are stable, non-irritating, skin treatment active agents containing formulations and delivery systems for topical application to the skin. The disclosed topical formulations and delivery systems provide controlled, gentle release of the active agents into the skin for the treatment of amenable skin conditions as well as for improvement of aesthetic skin properties. Also provided are methods for the formulation, manufacture and use of the disclosed formulations and delivery systems. Petrolatum is not known to have previously been utilized in non-aerosol (non-propellant based) spray formulations, meant to be dispensed via manual spray pump dispenser, as the viscosity of the petrolatum is high. Additionally, the percentage of petrolatum necessary to achieve a skin protective benefit is too high; thus, use of petrolatum can clog the spray pumps. The result would be a liquid or semi-solid (e.g., gel) composition that either does not spray at all or sprays inefficiently by sputtering through the orifice and leaving very uneven coverage on the skin. If any formulations did include petrolatum, the formulations did not include petrolatum in sufficient amounts to provide the necessary skin protectant benefits. It has now been unexpectedly discovered that a formulation with such a high concentration of petrolatum (e.g., 30% by weight or greater) as in the present disclosure is capable of being sprayed easily and efficiently providing even coverage on the skin. In certain embodiments, the sprayable formulation does not contain propellant gases as additives which can be harmful to the subject.

In certain embodiments, the formulation disclosed herein: i) allows for a reduction of use of main ingredients by a factor of 10× to 50×; ii) it is thus better for the environment; iii) the formulation leaves a silky and smooth sensation on the skin vs. a sticky, greasy and messy sensation obtained with known formulations and pure petrolatum jelly, for the same or better therapeutic effect; and iv) the formulation is a spray that provides significantly: 1) increased ease of use (at home and in hospital & nursing homes environments (e.g. one nurse vs. two) and 2) increased protection against cross bacteriological contamination (no fingers-spatula in the jar). The sprayable formulations can be applied to a skin surface without the need to touch or rub the skin surface. The risk of infection or contamination is therefore decreased. In certain embodiments, provided herein is a surprising finding of a composition comprising high percentage of petrolatum (e.g., 30% by weight or greater) in a sprayable form with improved sprayability compared to existing compositions comprising petrolatum.

The present disclosure provides skincare formulations, delivery systems and methods of use thereof for treating, alleviation or amelioration of dermatological conditions amenable to treatment with an active ingredient. Amenable conditions include, without limitation, inflammatory disorders of the skin and skin conditions characterized by increased cell turnover including psoriasis, photoaging, weather-beaten appearance, yellowing, loss of elasticity, loss of collagen rich appearance and/or youthfulness, redness, dryness, age spots, skin wrinkles, acne, rosacea, ichthyosis, xerosis, diaper rash, dermatitis, cracked skin on hands and feet, as well as skin cancers.

The compositions of the present disclosure can also be used as a healant for minor scrapes and burns; moisturizer for, e.g., face, hands, or feet and more; protective barrier for pet paws; Diaper rash; eye makeup remover; hair split end reducer; Skin stain prevention from hair dye or nail polish; perfume scents preserver; and lubricator for stuck objects.

The disclosed formulations are also useful for improvement in one or more aesthetic criteria, including, but not limited to, a perceived improvement in apparent skin age, skin tone, weather-beaten appearance, yellowing, loss of elasticity, redness, dryness, age spots, skin wrinkles, skin smoothness, brightness, radiance, as well as skin pores becoming less noticeable.

As used herein, the term "about" refers to +/−5% of the value specified.

As used herein, the terms "treatment" or "treating" with respect to a skin condition generally means administration with the intent to provide a pharmacodynamic effect, regardless of the outcome. In certain embodiments, "treatment" or "treating" means "having positive effect on a skin condition" and encompass reduction, amelioration, and/or alleviation of at least one symptom of a skin condition, a reduction, amelioration, and/or alleviation in the severity of the skin conditions, delay, prevention, or inhibition of the progression of the skin condition, or a perceived improvement or benefit as a result of the treatment. It may also mean achieving treatment results comparable or better to that of a prescription drug with a non-prescription product. Treatment, as used herein, therefore does not require total curing of the condition. In certain embodiments, a formulation or delivery system of the present disclosure may reduce the severity of a skin condition, reduce the severity of symptoms associated therewith, provide improvement to a patient's quality of life, or delay, prevent, inhibit the onset of one or more symptoms of a skin condition, or provide a perceived benefit. As used herein, these terms also encompass aesthetic improvements to the skin upon application of the disclosed active agents containing formulations.

As used herein, the term "wt %" with respect to an ingredient or combination of ingredients in a disclosed formulation means a concentration of that ingredient or combination of ingredients by weight based on the total weight of the formulation.

As used herein, the terms "application," "apply," and "applying" with respect to a disclosed topical formulation, or method of using a disclosed topical formulation, refer to any manner of administering a topical formulation to the skin of a patient which, in medical or cosmetology practice, delivers the formulation to the patient's skin surface. Smearing, rubbing, spreading, spraying a disclosed topical formulation, with or without the aid of suitable devices, on a subject's skin are all included within the scope of the term "application," as used herein. The terms "topical" or "topically" with respect to administration or application of a disclosed formulation refer to epicutaneous administration or application, or administration onto skin.

As used herein, the phrase "effective amount" or "therapeutically effective amount", used herein interchangeably, refers to an amount of a formulation, or component thereof, effective to alleviate or ameliorate a skin condition as noted above, including a range of effects, from a detectable local improvement in an area of topical application to substantial relief of symptoms to an improvement in one or more aesthetic criteria, including, but not limited to, a perceived improvement in damage from free radicals from sunlight (UVB, UVA, Visible Light), HEV (blue) light, Infrared (IR), pollution, irritants, allergens, or various environmental toxins, apparent skin age, radiation damage, sun or UV damage, skin tone, weather-beaten appearance, yellowing, appearance of fine lines, skin roughness, skin sagging, skin firmness, dryness, age spots, skin wrinkles, skin smoothness, brightness, radiance, as well as skin pores becoming less noticeable, hyperpigmentation, scars, skin surface irregularities, rosacea, acne, psoriasis, skin's regenerative and renewal process, redness, ichthyosis, severity of photodamage, lack of tactile smoothness, lack of visual smoothness, lack of softness, lack of luminosity, lack of radiance, skin texture, fine facial wrinkles, crow's feet, dyschromia, crepey skin texture, reduction in skin elasticity, and other damaging skin conditions. The effective amount can vary with the particular condition or conditions being treated, the severity of the condition, the duration of the treatment, the specific components of the composition being used, and other factors. In certain embodiments, the disclosed compositions and formulations provide a method for stabilizing and delivering active agents in an efficacious manner to the skin. Certain disclosed compositions, formulations, delivery system, and methods of use thereof may reduce, minimize, or eliminate normally-observed dermatoses including, inter alia, itching, severe skin flaking, breakdown of the skin barrier, discomfort, extreme dryness, cracking of the skin and sensitization. In certain embodiments, the disclosed compositions, formulations, delivery system, and methods of use thereof also provide aesthetic improvements in the skin, including but not limited to skin that appears younger, skin exhibiting a more even tone, skin in which the pores are less noticeable, and skin that is judged by the user to be smoother, and/or to be improved with respect to its weather-beaten or aged appearance, yellowing, loss of elasticity, redness, dryness, age spots, and/or skin wrinkles.

In certain embodiments, the delivery systems disclosed herein not only maintain product stability, including stability of the formulated active agent. In certain embodiments, the inventors surprisingly have found effectiveness of certain disclosed formulations in comparison with other skincare formulations. As such, the certain disclosed formulations, and methods of use thereof, function effectively in skincare treatments at a non-prescription strength, as compared with prescription strength active agents. In certain embodiments, the formulations cause reduced, minimal or no skin irritation and other possible side effects typically associated with such formulations, especially in daily, long-term use.

Without wishing to be bound by theory, it is contemplated that unexpected results associated with certain embodiments of the formulations are obtained by the synergistic operation of the delivery systems herein, i.e., the functioning of the delivery systems resulting in controlled release of the active agent(s). In this, the disclosed formulations of certain embodiments release the active agents at maximum, optimum strength and rate of release with minimal or no irritation to the skin.

Without wishing to be bound by theory, it is contemplated that in certain embodiments, the increased efficiency of delivery of the active agent coupled with the marked reduction in irritation observed upon administration of the presently disclosed formulations, permit the formulation and use of the delivery systems with significantly higher concentrations of an active ingredient than previously employed. As such, certain disclosed formulations and delivery systems provide effective skincare treatments at non-prescription strength, all while also being gentle on the skin and well-tolerated by consumers.

In some embodiments, the present disclosure provides a skin barrier protective delivery system comprising petrolatum. In some embodiments, the petrolatum is present at a concentration of at least 30 wt %. In some embodiments, the petrolatum is present at a concentration range of 25-60 wt %. In some embodiments, the petrolatum is present at a concentration of 40 wt %. In some embodiments, the petrolatum is present at a concentration of 50 wt %.

In some embodiments, provided herein is a skin barrier protective delivery system comprising: (i) a mixture of Coconut Alkanes at a concentration range of 30-70 wt % and Coco-Caprylate/Caprate at a concentration range of 3-7 wt %; and (ii) petrolatum, wherein the petrolatum is present at a concentration of at least 30 wt %. In some embodiments, the petrolatum is present at a concentration of 40 wt %. In some embodiments, the petrolatum is present at a concentration of 50 wt %. In some embodiments, the skin barrier protective delivery system is a sprayable composition. In some embodiments, the skin barrier protective delivery system is in the form of a sprayable liquid, semi-liquid or gel.

In some embodiments, provided herein is a skin barrier protective delivery system of comprising (i) a mixture of Coconut Alkanes at a concentration range of 30-70 wt % and Coco-Caprylate/Caprate at a concentration range of 3-7 wt %; and (ii) petrolatum, wherein the petrolatum is present at a concentration of 25-60 wt %; wherein the delivery system is sprayable. In some embodiments, the petrolatum is present at a concentration of 40 wt %. In some embodiments, the petrolatum is present at a concentration of 50 wt %. In some embodiments, the skin barrier protective delivery system is a sprayable composition. In some embodiments, the skin barrier protective delivery system is in the form of a sprayable gel.

In some embodiments, a skin barrier protective delivery system comprises (i) a mixture of Coconut Alkanes at a concentration range of 30-65 wt % and Coco-Caprylate/Caprate at a concentration range of 3-7 wt %; and (ii) petrolatum, wherein the petrolatum is present at a concentration of at least 30 wt %. In some embodiments, the petrolatum is present at a concentration of 40 wt %. In some embodiments, the petrolatum is present at a concentration of 50 wt %. In some embodiments, the skin barrier protective delivery system is a sprayable composition. In some embodiments, the skin barrier protective delivery system is in the form of a sprayable gel.

In some embodiments, a skin barrier protective delivery system comprises (i) a mixture of Coconut Alkanes at a concentration range of 30-65 wt % and Coco-Caprylate/Caprate at a concentration range of 3-7 wt %; and (ii) petrolatum, wherein the petrolatum is present at a concentration of 25-60 wt %; wherein the delivery system is sprayable. In some embodiments, the petrolatum is present at a concentration of 40 wt %. In some embodiments, the petrolatum is present at a concentration of 50 wt %. In some embodiments, the skin barrier protective delivery system is a sprayable composition. In some embodiments, the skin barrier protective delivery system is in the form of a sprayable gel.

It is understood that the mixture of Coconut Alkanes and Coco-Caprylate/Caprate in the compositions of the present disclosure is present at a concentration of at most about 70 by weight of the formulation. In some embodiments, the present disclosure comprises (i) a mixture of Coconut Alkanes and Coco-Caprylate/Caprate, wherein the combined concentration of Coconut Alkanes and Coco-Caprylate/Caprate is at most 70 wt %; and (ii) petrolatum, wherein the petrolatum is present at a concentration of at least 30 wt %. In some embodiments, the skin barrier protective delivery system is a sprayable composition. In some embodiments, the skin barrier protective delivery system is in the form of a sprayable gel.

In some embodiments, a skin barrier protective delivery system comprises (i) a mixture of Coconut Alkanes at a concentration range of 30-70 wt % and Coco-Caprylate/Caprate at a concentration range of 3-7 wt %, wherein the combined concentration of Coconut Alkanes and Coco-Caprylate/Caprate is at most 70 wt %; and (ii) petrolatum, wherein the petrolatum is present at a concentration of 25-60 wt %; wherein the delivery system is sprayable. In some embodiments, the petrolatum is present at a concentration of 40 wt %. In some embodiments, the petrolatum is present at a concentration of 50 wt %. In some embodiments, the skin barrier protective delivery system is a sprayable composition. In some embodiments, the skin barrier protective delivery system is in the form of a sprayable gel.

In some embodiments, a skin barrier protective delivery system comprises (i) a mixture of Coconut Alkanes at a concentration range of 30-70 wt % and Coco-Caprylate/Caprate at a concentration range of 3-7 wt %, wherein the combined concentration of Coconut Alkanes and Coco-Caprylate/Caprate is at most 70 wt %; and (ii) petrolatum, wherein the petrolatum is present at a concentration of at least 30 wt %. In some embodiments, the skin barrier protective delivery system is a sprayable composition. In some embodiments, the skin barrier protective delivery system is in the form of a sprayable gel.

Petrolatum

Petrolatum is a combination of hydrocarbons obtained as a semi-solid from dewaxing paraffinic residual oil. Petrolatum comprises predominantly saturated crystalline and liquid hydrocarbons, predominately having a carbon chain length of C25 and above.

Petrolatum is generally a safe and effective topical agent suitable for use in a wide range of topical applications including, but not limited to moisturizing creams and lotions; make-up; hand and foot creams and lotions; skin protectants; wound care; lip balms and lipsticks; salves and rubs; baby care; hair care. In pharmaceuticals, petrolatum is used as medicated pain balms, ointments, and creams. Petrolatum protects injured or exposed skin or mucous membrane surfaces from harmful stimuli and may help provide relief to such surfaces. More particularly, such products can help prevent (or temporarily protect; and, optionally, help to relieve) chafed, chapped, or cracked skin.

Lip products that contain petrolatum at a concentration recognized to be safe and effective by the FDA in its final Skin Protectant Monograph may claim, as a benefit, temporarily preventing dryness and helping to relieve chapping of the exposed surfaces of the lips.

Both skin and lip products that contain over 30% petrolatum may also claim helping to protect the skin/lips from the drying effects of wind and cold weather.

Despite its long history of safety and efficacy, petrolatum-based topical formulations are known to have certain limitations—they can be unctuous and cosmetically-inelegant. Application of topical products by means of a user introducing a hand or inanimate applicator (brushes, spatulas, swabs, sponges, puffs) into a container can be unhygienic, and can have potentially deleterious health consequences. Even if "clean" (e.g., not containing exogenous contaminants or disease-carrying organisms), the hand can contain microorganisms present in the skin microbiome. Applicators are often not cleaned between uses and can be colonized by microorganisms.

There has been and remains a need for cosmetically elegant, non-unctuous, and in certain embodiments, sprayable compositions that apply petrolatum at a safe and effective concentration of at least 30% by weight and other ingredients in a manner that not only protects the skin barrier but also effectively and safely delivers other functional and/or pharmaceutically active ingredients to the skin. Those needs are met by the skin barrier protective delivery systems of the present disclosure. Thus, one of the objectives of the present disclosure is to increase water retention and improve skin roughness (moisturization).

In some embodiments, petrolatum is present in the skin barrier protective system of the present disclosure at a concentration of at least about 30% by weight. In some embodiments, petrolatum is present in the skin barrier protective system of the present disclosure at a concentration range of about 25% to about 30%, about 25% to about 60%, about 30% to about 60%, about 30% to about 55%, about 30% to about 50%, about 30% to about 45%, about 30% to about 40%, about 30% to about 35%, about 35% to about 60%, about 35% to about 55%, about 35% to about 50%, about 35% to about 45%, about 35% to about 40%, about 40% to about 60%, about 40% to about 55%, about 40% to about 50%, about 40% to about 45%, about 45% to about 60%, about 50% to about 60%, about 50% to about 55%, or about 55% to about 60%. In some embodiments, petrolatum is present in the skin barrier protective system of the present disclosure at a concentration of at least about 25%, 30%, 35%, 40%, 45%, 50%, 55%, or 60%, by weight, or even higher. In some embodiments, the petrolatum is present at a concentration of 40 wt %. In some embodiments, the petrolatum is present at a concentration of 50 wt %.

Coconut Alkanes and Coco-Caprylate/Caprate

Coconut Alkanes are produced by reduction and hydrogenation of a mixture of fatty acids derived from Coconut Oil. Different carbon chain lengths and the distributions of different carbon chain lengths are commercially available, including from Biosynthis Ltd. (Saint-Cyr-sous-Dourdan France), ranging from C5-C14, including C8-C10, C9-C12 and C12-C14, and mixtures of the foregoing. Coconut Alkanes are described in US Pre-Grant Patent Application Publication Nos. 2012/0027702, 2017/0143610, 2018/0256479, 2019/0343753, 2019/0343753, and 2021/0154110, the disclosures of each of which are incorporated in pertinent part in their entireties.

Coco-Caprylate/Caprate (CAS #95912-86-0) is a mixture of esters of Coconut Alcohol (mixture of fatty alcohols derived from Coconut Oil) with Caprylic Acid and Capric Acid. Non-limiting examples of commercially available Coco-Caprylate/Caprate include Cetiol® LC (BASF Corporation, Florham Park, NJ), Dub 810 C (Stearinerie Dubois Fils, Boulogne Billancourt, France), and Lanol™ 2681 (Seppic, Paris, France).

A mixture of Coconut Alkanes and Coco-Caprylate/Caprate is commercially available, including under the tradenames Vegelight® 1214 (from Biosynthis) and Vesgesil™ 345 (Global Ingredient Solutions, Irvine, CA).

In some embodiments, mixtures of Coconut Alkanes and Coco-Caprylate/Caprate comprise Coconut Alkanes and Coco-Caprylate/Caprate at a ratio of about 99:1, about 95:5, about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, about 5:95, about 1:99, or any ratio in-between. In some embodiments, compositions of the present disclosure comprise a 90%:10% mixture of Coconut Alkanes and Coco-Caprylate/Caprate.

In some embodiments, compositions of the present disclosure comprise Coconut Alkanes at a concentration range of about 30-70 wt %, for example 30%-67%, 30%-65%, 30%-60%, 30%-55%, 30%-50%, 30%-45%, 30%-40%, 30%-35%, 35%-70%, 35%-67%, 35%-65%, 35%-60%, 35%-55%, 35%-50%, 35%-45%, 35%-40%, 40%-70%, 40%-67%, 40%-65%, 40%-60%, 40%-55%, 40%-50%, 40%-45%, 41%-42%, 42%-43%, 43%-44%, 44%-45%, 45%-70%, 45%-67%, 45%-65%, 45%-60%, 45%-55%, or 45%-50% by weight, based on the total weight of the formulation. In some embodiments, composition of the present disclosure comprise Coconut alkanes at a concentration of about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69% or 70% by weight, based on the total weight of the formulation.

In some embodiments, compositions of the present disclosure comprise Coco-Caprylate/Caprate at a concentration range of 3-7% by weight, for example 3%-6.5%, 3%-6%, 3%-5.5%, 3%-5%, 3%-4.5%, 3%-4%, 3%-3.5%, 3.5%-7%, 4%-7%, 4.5%-7%, 5%-7%, 5.5%-7%, 6%-7%, 6.5%-7%, 4%-7%, 4%-6.5%, 4%-6%, 4%-5.5%, 4%-5%, 4%-4.5% by weight, based on the total weight of the formulation. In some embodiments, composition of the present disclosure comprises Coco-Caprylate/Caprate at a concentration of about 3%, 3.5%, 4%, 4.1%, 4.2%, 4.3%, 4.4%, 4.5%, 4.6%, 4.7%, 4.8%, 4.9%, 5%, 5.5%, 6%, 6.5%, or 7% by weight, based on the total weight of the formulation.

In some embodiments, the compositions of the present disclosure comprise (i) about 30%-70% by weight Coconut Alkanes, and about (ii) 3%-7% by weight Coco-Caprylate/Caprate. In some embodiments, the compositions of the present disclosure comprise (i) about 30%-67% by weight Coconut Alkanes, and about (ii) 3%-7% by weight Coco-Caprylate/Caprate. In some embodiments, the compositions of the present disclosure comprise (i) about 30%-65% by weight Coconut Alkanes, and about (ii) 3%-7% by weight Coco-Caprylate/Caprate. In some embodiments, the compositions of the present disclosure comprise about 42%-43% by weight Coconut Alkanes and about 4%-5% by weight Coco-Caprylate/Caprate. In some embodiments, the compositions of the present disclosure comprise about 46.8% mixture of Coconut Alkanes and Coco-Caprylate/Caprate, wherein Coconut Alkanes comprise about 90% of the mixture (42.12% by weight of the composition), and Coco-Caprylate/Caprate comprise about 10% of the mixture (4.68% by weight of the composition).

In some embodiments, the present disclosure is directed to a skin barrier protective delivery system comprising or consisting essentially of: (a) Coconut Alkanes and/or Coco-Caprylate/Caprate, optionally, a mixture of the two or more, in a ratio of Coconut Alkanes to Coco-Caprylate/Caprate at from about 3:1 to about 9:1 and (b) Petrolatum at a concentration of at least about 30%. In some embodiments, the petrolatum is present at a concentration of 40 wt %. In some embodiments, the petrolatum is present at a concentration of 50 wt %.

In certain embodiments, a skin barrier protective delivery system comprises or consists essentially of: (a) Coconut Alkanes and/or Coco-Caprylate/Caprate, optionally, a mixture of the two, more, in a ratio of Coconut Alkanes to Coco-Caprylate/Caprate at from about 3:1 to about 9:1; and (b) Petrolatum at a concentration of at least about 30%; and the ratio of (a) to (b) is from about 7:3 to about 1:3. In some embodiments, the petrolatum is present at a concentration of 40 wt %. In some embodiments, the petrolatum is present at a concentration of 50 wt %.

In some embodiments, the present disclosure is directed to a skin barrier protective delivery system comprises or consists essentially of (a) Coconut Alkanes and/or Coco-Caprylate/Caprate, optionally, a mixture of the two or more, in a ratio of Coconut Alkanes to Coco-Caprylate/Caprate at from about 3:1 to about 9:1 and (b) Petrolatum at a concentration of at least about 30%; and the ratio of (a) to (b) is from about 7:3 to about 1:3, is that the skin barrier protective delivery system is sprayable. In some embodiments, the petrolatum is present at a concentration of 40 wt %. In some embodiments, the petrolatum is present at a concentration of 50 wt %.

In some embodiments of the skin barrier protective delivery system of the present disclosure, the ratio of (a) Coconut Alkanes and/or Coco-Caprylate/Caprate, optionally, a mixture of the two, to (b) Petrolatum is from about 7:3 to about 3:7. In some embodiments, the petrolatum is present at a concentration of 25-60 wt %. In some embodiments, the petrolatum is present at a concentration of 40 wt %.

In some embodiments of the skin barrier protective delivery system of the present disclosure, the ratio of (a) Coconut Alkanes and/or Coco-Caprylate/Caprate, optionally, a mixture of the two, to (b) Petrolatum is from about 2:1 to about 1:2. In other embodiments of the skin barrier protective delivery system of the present disclosure, the ratio of (a) Coconut Alkanes and/or Coco-Caprylate/Caprate, optionally, a mixture of the two, to (b) Petrolatum is from about 3:2 to about 2:3. In some embodiments, the petrolatum is present at a concentration of 25-60 wt %. In some embodiments, the petrolatum is present at a concentration of 40 wt %. In some embodiments, the petrolatum is present at a concentration of 50 wt %.

In still other embodiments of the skin barrier protective delivery system of the present disclosure, the ratio of (a) Coconut Alkanes and/or Coco-Caprylate/Caprate, optionally, a mixture of the two, to (b) Petrolatum is from about 5:4 to about 4:5, and in some embodiments, is about 10:9 to about 9:10, and about 1:1. In some embodiments, the ratio of (a) Coconut Alkanes and/or Coco-Caprylate/Caprate, optionally, a mixture of the two, to (b) Petrolatum is about 1:1. In some embodiments, the petrolatum is present at a concentration of 25-60 wt %. In some embodiments, the petrolatum is present at a concentration of 40 wt %. In some embodiments, the petrolatum is present at a concentration of 50 wt %.

In these embodiments, that ratio of (i) Coconut Alkanes to (ii) Coco-Caprylate/Caprate is from about 3:1 to about 9:1.

Other Excipients

In some embodiments, skin barrier protective delivery systems of the present disclosure further comprise at least one of a ceramide, a triglyceride, a phytosterol, a phytosterol ester, a terpene, a plant-based ester or wax, tocopherol and/or a phospholipid. In some embodiments, skin barrier protective delivery systems of the present disclosure comprise at least two of a ceramide, a triglyceride, a phytosterol, a phytosterol ester, a terpene, a plant-based ester or wax, tocopherol and/or a phospholipid. In some embodiments, skin barrier protective delivery systems of the present disclosure comprise at least three of a ceramide, a triglyceride, a phytosterol, a phytosterol ester, a terpene, a plant-based ester or wax, tocopherol and/or a phospholipid. In some embodiments, skin barrier protective delivery systems of the present disclosure comprise at least four of a ceramide, a triglyceride, a phytosterol, a phytosterol ester, a terpene, a plant-based ester or wax, tocopherol and/or a phospholipid. In some embodiments, skin barrier protective delivery systems of the present disclosure comprise a ceramide, a triglyceride, a phytosterol, a phytosterol ester, a terpene, a plant-based ester or wax, tocopherol and/or a phospholipid.

In some embodiments, skin barrier protective delivery systems of the present disclosure comprise a plant-based ester or wax. Plant oils, plant-derived esters and waxes, sterols, and esters of phytosterols and fatty acids (e.g., derived from plant seed oils) can be used in cosmetic, personal care and dermatology products.

In some embodiments, the plant-based ester or wax is selected from the group consisting of jojoba oils, jojoba esters, candelilla wax, carnauba wax, rice bran wax and sunflower wax. In some embodiments, the plant-based ester or wax is or comprises jojoba esters. *Simmondsia chinensis* (Jojoba) Seed Oil is the fixed oil expressed or extracted from seeds of the desert shrub, Jojoba, *Simmondsia chinensis*.

*Macadamia integrifolia* Seed Oil is a fixed oil obtained from the nut of *Macadamia integrifolia*.

Jojoba Oil/*Macadamia* Seed Oil Esters (CAS #97593-46-9) is a mixture of esters formed by the transesterification of Jojoba Seed Oil and *Macadamia integrifolia* Seed Oil.

In certain embodiments, the skin barrier protective delivery system of the present disclosure comprises at least one phytosterol and/or a terpene (e.g., squalene).

In some embodiments, skin barrier protective delivery system of the present disclosure comprises a terpene. Terpenes are organic compounds consisting of isoprene, a five-carbon building block. In some embodiments, skin barrier protective delivery system the present disclosure comprises a triterpene (C30), a hemiterpene (C5), a monoterpene (C10), a sesquiterpene (C15), a diterpene (C20), a sesterterpene (C25) a tetraterpene (C40), or any mixtures thereof.

In some embodiments, the terpene is a triterpene. In some embodiments, the triterpene is squalene. Squalene (CAS #111-02-4) is an unsaturated branched chain isoprenoid (triterpene) hydrocarbon found in a variety of plant oils or derived through fermentation.

In some embodiments, skin barrier protective delivery system of the present disclosure comprises at least one phytosterol. Phytosterols ($C_{17}H_{28}O$; CAS #949109-75-5) are a family of plant-derived alcohols of gonanes, a tetracyclic hydrocarbon with no double bonds. In some embodiments, the hydrogen atom in position 3 of the gonane is replaced by a hydroxyl group.

In some embodiments, skin barrier protective delivery system of the present disclosure comprises a phytosterol ester. In some embodiments, the phytosterol ester comprises esters derived from a plant, e.g., a seed or nut oil. In some embodiments, the seed or nut oil is selected from the group consisting of macadamia oil, almond oil, avocado oil, canola oil, coconut oil, corn oil, cottonseed oil, grapeseed oil, hazelnut oil, palm oil peanut oil, pine seed oil, pecan oil pumpkin seed oil, safflower oil, sesame oil, soy oil, sunflower oil, and walnut oil.

In some embodiments, the phytosterol ester is phytosteryl macadamiate. Phytosteryl Macadamiate (CAS #68990-51-2) is the ester of phytosterol and the fatty acids from *Macadamia integrifolia* Seed Oil.

In some embodiments, skin barrier protective delivery system of the present disclosure comprise tocopherol. Vitamin E is a plant-derived, lipid-soluble substance comprised of a chromanol ring with a side chain located at the C2 position. Tocopherol (CAS #10191-41-0) are forms of Vitamin E—designated alpha, beta, gamma, and delta, based on the number and position of methyl groups on the chromanol ring. Any form of tocopherol can be used in the compositions of the present disclosure.

In certain embodiments of the skin barrier protective delivery system of the present disclosure comprises at least one ceramide. In certain embodiments of the skin barrier protective delivery system of the present disclosure comprises at least two ceramides. In certain embodiments, the ceramides are one or both of Ceramide AP and/or Ceramide NP. Ceramides are a group of sphingolipids containing derivatives of sphingosine bases in amide linkage with a variety of fatty acids. Together with other stratum corneum lipids, ceramides play an essential role in structuring and maintaining the barrier function of the skin. In some embodiments, skin barrier protective delivery system of the present disclosure comprises Ceramide AP. In some embodiments, skin barrier protective delivery system of the present disclosure comprises Ceramide NP. Ceramide AP is an N-acylated sphingolipid consisting of phytosphingosine having a D-erythro structure linked to an alpha-hydroxy saturated or unsaturated fatty acid. Ceramide NP is an N-acylated sphingolipid consisting of phytosphingosine having a D-erythro structure linked to normal saturated or unsaturated fatty acid.

Many dermatological conditions and disorders that have a diminished skin barrier function are characterized by a decrease in ceramide content. Topical formulations that deliver lipids identical to, or that mimic, those in skin are reported to improve skin conditions. See, e.g., Coderch, L., López, O., de la Maza A., Parra J. "Ceramides and skin function" Am. J. Clin. Dermatol. 2003; 4(2):107-29.

In some embodiments, the skin barrier protective delivery system of the present disclosure comprises a triglyceride. In some embodiments, the triglyceride is a C18-C36 acid triglyceride. In some embodiments, the triglyceride is a C12-18 acid triglyceride.

In some embodiments, the skin barrier protective delivery system of the present disclosure comprises a mixture of jojoba esters, squalene, phytosteryl macadamiate, phytosterols, tocopherol, C18-C36 triglyceride and C12-C18 triglyceride in a combination solder under the tradename "L22®". Designed to mimic the distribution of skin lipids in "younger skin," L22® (Flora Technologies, Ltd., Chandler, AZ) is comprised of Jojoba Oil/*Macadamia* Seed Oil Esters, Squalene, Phytosteryl Macadamiate, Phytosterols and Tocopherol. The primary components of L22 are Jojoba Oil/*Macadamia* Seed Oil Esters (approx. 85%) and Squalene (12.5%). Phytosteryl Macadamiate and Phytosterols are present in L22 at a combined concentration of about 2.5%.

In certain embodiments, the skin barrier protective delivery system of the present disclosure comprises at least one ceramide, at least two ceramides, or at least one phytosterol and/or squalene.

In certain embodiments, the skin barrier protective delivery system of the present disclosure comprises at least one ceramide, at least two ceramides, or at least one phytosterol and squalene.

In certain embodiments, the skin barrier protective delivery system of the present disclosure comprises at least one ceramide, a triglyceride, a phytosterol, phytosterol macadamiate, squalene, jojoba esters, and tocopherol.

In certain embodiments, the skin barrier protective delivery system of the present disclosure comprises ceramide NP, ceramide AP, jojoba esters, squalene, phytosterols, phytosteryl macadamiate, tocopherol, C18-C36 acid triglyceride, and C12-18 acid triglyceride. Each of the embodiments can optionally comprise one or a mixture of plant-derived esters.

In certain embodiments, plant-derived esters include Jojoba Oil/*Macadamia* Seed Oil Esters and/or Phytosteryl Macadamiate. In certain embodiments, the skin barrier protective delivery system of the present disclosure comprises Jojoba Oil/*Macadamia* Seed Oil Esters and Phytosteryl Macadamiate.

Plant-based esters, when present, are included in the skin barrier protective delivery system of the present disclosure alone, or in combination with one or more plant oils or waxes, at a combined concentration of up to about 20 wt %, up to about 15 wt %, up to about 10 wt %, up to about 5 wt %, or up to about 1 wt %. For example, plant-based esters can be present in an amount of about 0.1-0.15 wt %, about 0.15-0.2 wt %, about 0.2-0.25 wt %, about 0.25-0.3 wt %, about 0.3-0.35 wt %, about 0.35-0.4 wt %, about 0.4-0.45 wt %, about 0.45-0.5 wt %, about 0.5-0.55 wt %, about 0.55-0.6 wt %, about 0.6-0.65 wt %, about 0.65-0.7 wt %, about 0.7-0.75 wt %, about 0.75-0.8 wt %, about 0.8-0.85 wt %, about 0.85-0.9 wt %, about 0.9-0.95 wt %, about 0.95-1 wt %, about 1-1.5 wt %, about 1.5-2 wt %, about 2-3 wt %, about 3-4 wt %, about 4-5 wt %, about 5-6 wt %, about 6-7 wt %, about 7-8 wt %, about 8-9 wt %, about 9-10 wt %, about 10-15 wt %, or about 15-20 wt %, based on total weight of the formulation.

Terpene (e.g., squalene), when present, is included in the skin barrier protective delivery system of the present disclosure at a concentration of up 5 wt %, less than about 4 wt %, less than about 3%, less than about 2 wt %, less than about 1 wt %, or less than about 0.5 wt %. For example, a terpene (e.g., squalene) can be present in an amount of about 0.1-0.15 wt %, about 0.15-0.2 wt %, about 0.2-0.25 wt %, about 0.25-0.3 wt %, about 0.3-0.35 wt %, about 0.35-0.4 wt %, about 0.4-0.45 wt %, about 0.45-0.5 wt %, about 0.5-0.55 wt %, about 0.55-0.6 wt %, about 0.6-0.65 wt %, about 0.65-0.7 wt %, about 0.7-0.75 wt %, about 0.75-0.8 wt %, about 0.8-0.85 wt %, about 0.85-0.9 wt %, about 0.9-0.95 wt %, about 0.95-1 wt %, about 1-1.5 wt %, about 1.5-2 wt %, about 2-3 wt %, about 3-4 wt %, or about 4-5 wt % based on the total weight of the formulation. In some embodiments, squalene is present in an amount of about 0.37% based on the total weight of the formulation.

In one embodiment, the at least one ceramide, when present, is included in the skin barrier protective delivery system of the present disclosure is at a concentration ranging from about 0.01% to about 0.5%. For example, a ceramide can be present at a concentration of about 0.01% to about 0.1%, about 0.05 wt %-0.4 wt %, about 0.05-0.3 wt %, about 0.05-0.2 wt %, about 0.05-0.1 wt %, about 0.05 wt %-0.06 wt %, about 0.06 wt %-0.06 wt %, about 0.07 wt %-0.08 wt %, about 0.08 wt %-0.09 wt %, about 0.09 wt %-0.1 wt %, In some embodiments, the skin barrier protective delivery system of the present disclosure further comprises at least one of a polysaccharide, a gum, a buffering agent (e.g., an acid), and a root plant extract.

In some embodiments, the skin barrier protective delivery system of the present disclosure comprises at least one polysaccharide. In some embodiments, at least one polysaccharide can be, for example, maltodextrin, cellulose, hydroxyethylcellulose, hydroxypropylcellulose, carboxymethylcellulose, starch, hydrolyzed starch, partially hydrolyzed starch, xylans, inulin, cellobiose, scleroglucan, chitosan, ulvan, fucoidan, alginate, pectin, heparin, hyaluronic acid, and mixtures thereof. In some embodiments, the polysaccharide is maltodextrin.

In some embodiments, the skin barrier protective delivery system of the present disclosure comprises at least one gum. In some embodiments, the at least one gum can be, for example, selected from the group consisting of guar gums, xanthan gums, pullulan gums, agar-agar gums, carrageenan gums, gellan gums, gum arables, and tragacanth gums. In some embodiments, the gum is *Acacia senegal* gum.

In some embodiments, the skin barrier protective delivery system of the present disclosure comprises at least one plant extract. In some embodiments, the skin barrier protective delivery system of the present disclosure comprises at least one root plant extract. In some embodiments, the skin barrier protective delivery system of the present disclosure comprises at least one fruit extract. In some embodiments, the skin barrier protective delivery system of the present disclosure comprises at least one vegetable extract. In some embodiments, at least one root plant extract is selected from the group consisting of sweet potato, potato, beet, carrot, parsnip, horseradish and radish. In some embodiments, the root plant extract is *Ipomoea batatas* root extract. In some embodiments, the at least one plant extract is derived from cucumber, garlic, pepper, berries (including raspberry, blackberry, strawberry, elderberry, blueberry, bilberry), asparagus, and the like. In some embodiments, the plant extract is a *Vaccinium myrtillus* Fruit Extract. In some embodiments, the plant extract is a *Cucumis sativus* (Cucumber) Fruit Extract. In some embodiments, the plant extract is a Garlic (*Allium sativum*) Extract. Plant extracts can be present in the compositions of the present disclosure in the range of 0.01-0.1 wt %. In some embodiments, a plant extract is present in a concentration range of about 0.01-0.9 wt %, about 0.01-0.85 wt %, about 0.01-0.8 wt %, about 0.01-0.75 wt %, about 0.01-0.7 wt %, about 0.01-0.65 wt %, about 0.01-0.6 wt %, about 0.01-0.55 wt %, about 0.01-0.5 wt %, about 0.01-0.45 wt %, about 0.01-0.4 wt %, about 0.01-0.35 wt %, about 0.01-0.3 wt %, about 0.01-0.25 wt %, about 0.01-0.2 wt %, about 0.01-0.15 wt %, about 0.01-0.1 wt %, about 0.01-0.02 wt %, about 0.02-0.03 wt %, about 0.03-0.04 wt %, about 0.04-0.05 wt %, about 0.0-0.06 wt %, about 0.06-0.07 wt %, about 0.07-0.08 wt %, about 0.08-0.09 wt %, or about 0.09-0.1 wt % based on the weight of the formulation.

In some embodiments, the skin barrier protective delivery system of the present disclosure comprises at least one buffering agent. In some embodiments, the buffering agent is an acid. In some embodiments, the acid is citric acid. In other embodiments, the acid can be a carboxylic acid. In some embodiments, the acid is selected from the group consisting of citric acid, acetic acid, succinic acid, lactic acid, maleic acid, fumaric acid, palmitic acid, cholic acid, pamoic acid, mucic acid, D-glutamic acid, D-camphoric acid, glutaric acid, phthalic acid, tartaric acid, lauric acid, stearic acid, salicyclic acid, sorbic acid, benzoic acid, and cinnamic acid, and their salts, e.g., alkali or alkali earth metal salts thereof. In some embodiments, the acid is citric acid/sodium citrate. In some embodiments, the buffering agent is present at a concentration of about 0.001-1 wt %, about 0.001-0.5 wt %, about 0.001-0.1 wt %, about 0.001-0.05 wt %, about 0.001-0.01 wt %, about 0.001-0.005 wt %, about 0.001-0.003 wt %, about 0.001-0.002 wt %, about 0.01-5 wt %, about 0.01-1 wt %, about 0.1-1 wt %, about 0.5-1 wt %, about 0.01-0.05 wt %, about 0.05-0.1 wt %, about 0.1-0.15 wt %, about 0.15-0.2 wt %, about 0.2-0.25 wt %, about 0.25-0.3 wt %, about 0.3-0.35 wt %, about 0.35-0.4 wt % or about 0.4-0.45 wt %, about 0.45-0.5 wt %, about 0.5-0.55 wt %, about 0.55-0.6 wt %, about 0.6-0.65 wt %, about 0.65-0.7 wt %, about 0.7-0.75 wt %, about 0.75-0.8 wt %, about 0.8-0.85 wt %, about 0.85-0.9 wt %, about 0.9-0.95 wt %, about 0.95-1 wt %, about 1-1.5 wt %, about 1.5-2 wt %, about 2-3 wt %, about 3-4 wt %, about 4-5 wt %, about 5-6 wt %, about 6-7 wt %, about 7-8 wt %, about 8-9 wt %, about 9-10 wt %, about 10-15 wt %, about 15-20 wt %, or about 20-30 wt %, based on total weight of the formulation.

In some embodiments, the skin barrier protective delivery system of the present disclosure comprises at least one of *Ipomoea batatas* root extract, citric acid, *Acacia senegal* gum, and maltodextrin. In some embodiments, the skin barrier protective delivery system of the present disclosure comprises *Ipomoea batatas* root extract, citric acid, *Acacia senegal* gum, and maltodextrin. A combination of *Ipomoea batatas* root extract, citric acid, *Acacia senegal* gum, and maltodextrin is commercially sold under the trade name Natpure Xfine Potato SP313.

In some embodiments, the skin barrier protective delivery system of the present disclosure comprises ceramide NP, ceramide AP, jojoba esters, squalene, phytosterols, phytosteryl macadamiate, tocopherol, C18-C36 acid triglyceride, C12-18 acid triglyceride, *Ipomoea batatas* root extract, *Acacia senegal* gum, citric acid, and maltodextrin.

In some embodiments, the skin barrier protective delivery system of the present disclosure further comprises zinc oxide. In some embodiments, zinc oxide is present at a concentration range of about 1-23 wt %, e.g., about 5-15%, about 8-10 wt %, about 10-12 wt %, about 12-14 wt %, about 10-15 wt %, about 15-20 wt %, about 20-25 wt %, or about 25-30 wt %. In some embodiments, zinc oxide is present at a concentration of about 10 wt %, about 10.5 wt %, about 11 wt %, about 11.5 wt %, about 12 wt %, about 12.5 wt %, about 13 wt %, about 13.5 wt %, about 14 wt %, 1 about 4.5 wt %, or about 15 wt %.

Excipients in the skin barrier protective delivery system of the present disclosure can be present, individually or cumulatively, in a concentration range of about 0.001-10 wt %, about 0.001-5 wt %, about 0.001-1 wt %, about 0.001-0.5 wt %, about 0.001-0.4 wt %, about 0.001-0.3 wt %, about 0.001-0.25 wt %, about 0.001-0.2 wt %, about 0.001-0.15 wt %, about 0.001-0.1 wt %, about 0.001-0.05 wt %, about 0.001-0.04 wt %, about 0.001-0.03 wt %, about 0.001-0.01 wt %, about 0.001-0.025 wt %, about 0.001-0.02 wt %, about 0.001-0.015 wt %, about 0.005-0.01 wt %, about 0.01-0.05 wt %, about 0.05-0.1 wt %, about 0.1-0.15 wt %, about 0.15-0.2 wt %, about 0.2-0.25 wt %, about 0.25-0.3 wt %, about 0.3-0.35 wt %, about 0.35-0.4 wt %, or about 0.4-0.45 wt % to any of about 0.45-0.5 wt %, about 0.5-0.55 wt %, about 0.55-0.6 wt %, about 0.6-0.65 wt %, about 0.65-0.7 wt %, about 0.7-0.75 wt %, about 0.75-0.8 wt %, about 0.8-0.85 wt %, about 0.85-0.9 wt %, about 0.9-0.95 wt %, about 0.95-1 wt %, about 1-1.5 wt %, about 1.5-2 wt %, about 2-3 wt %, about 3-4 wt %, about 4-5 wt %, about 5-6 wt %, about 6-7 wt %, about 7-8 wt %, about 8-9 wt %, about 9-10 wt %, about 10-15 wt %, about 15-20 wt %, or about 20-30 wt %, based on total weight of the formulation.

Exemplary Compositions

In some embodiments, the skin barrier protective delivery system of the present disclosure comprises (i) at least 30 wt % Petrolatum; (ii) Coconut Alkanes in the range of 30-70 wt %; (iii) Coco-Caprylate/Caprate in the range of 3-7 wt %; (iv) ceramide NP in the range of 0.01-0.1 wt %; (v) ceramide AP in the range of 0.01-0.1 wt %; (vi) Jojoba Esters in the range of 0.1-1.5 wt %; (vii) Squalene in the range of 0.1-1 wt %; (viii) Phytosteryl Macadamiate in the range of 0.01-0.1 wt %; (ix) Phytosterols in the range of 0.005-0.1 wt %; (x) Tocopherol in the range of 0.001-0.1 wt %; (xi) C18-36 Acid Triglyceride in the range of 0.5-5 wt %; (xii) C12-18 Acid Triglyceride in the range of 0.1-1 wt %; (xiii) *Ipomoea batatas* root extract in the range of 0.01-0.1 wt %; (xiv) citric acid in the range of 0.001-0.01 wt %; (xv) *Acacia senegal* gum in the range of 0.001-0.1 wt %; and (xvi) Maltodextrin in the range of 0.001-0.1 wt %. In some embodiments, the delivery system is a sprayable formulation.

In some embodiments, the skin barrier protective delivery system of the present disclosure comprises (i) at least 30 wt % Petrolatum; (ii) Coconut Alkanes in the range of 30-67 wt %; (iii) Coco-Caprylate/Caprate in the range of 3-7 wt %; (iv) ceramide NP in the range of 0.01-0.1 wt %; (v) ceramide AP in the range of 0.01-0.1 wt %; (vi) Jojoba Esters in the range of 0.1-1.5 wt %; (vii) Squalene in the range of 0.1-1 wt %; (viii) Phytosteryl Macadamiate in the range of 0.01-0.1 wt %; (ix) Phytosterols in the range of 0.005-0.1 wt %; (x) Tocopherol in the range of 0.001-0.1 wt %; (xi) C18-36 Acid Triglyceride in the range of 0.5-5 wt %; (xii) C12-18 Acid Triglyceride in the range of 0.1-1 wt %; (xiii) *Ipomoea batatas* root extract in the range of 0.01-0.1 wt %; (xiv) citric acid in the range of 0.001-0.01 wt %; (xv) *Acacia senegal* gum in the range of 0.001-0.1 wt %; and (xvi) Maltodextrin in the range of 0.001-0.1 wt %. In some embodiments, the delivery system is a sprayable formulation.

In some embodiments, the skin barrier protective delivery system of the present disclosure comprises (i) at least 30 wt % Petrolatum; (ii) Coconut Alkanes in the range of 30-65 wt %; (iii) Coco-Caprylate/Caprate in the range of 3-7 wt %; (iv) ceramide NP in the range of 0.01-0.1 wt %; (v) ceramide AP in the range of 0.01-0.1 wt %; (vi) Jojoba Esters in the range of 0.1-1.5 wt %; (vii) Squalene in the range of 0.1-1 wt %; (viii) Phytosteryl Macadamiate in the range of 0.01-0.1 wt %; (ix) Phytosterols in the range of 0.005-0.1 wt %; (x) Tocopherol in the range of 0.001-0.1 wt %; (xi) C18-36 Acid Triglyceride in the range of 0.5-5 wt %; (xii) C12-18 Acid Triglyceride in the range of 0.1-1 wt %; (xiii) *Ipomoea batatas* root extract in the range of 0.01-0.1 wt %; (xiv) citric acid in the range of 0.001-0.01 wt %; (xv) *Acacia senegal* gum in the range of 0.001-0.1 wt %; and (xvi) Maltodextrin in the range of 0.001-0.1 wt %. In some embodiments, the delivery system is a sprayable formulation.

In some embodiments, the skin barrier protective delivery system of the present disclosure comprises (i) 50 wt % Petrolatum; (ii) 42-43 wt % Coconut Alkanes; (iii) 4-5 wt % Coco-Caprylate/Caprate; (iv) 0.05 wt % ceramide NP; (v) 0.05 wt % ceramide AP; (vi) 0.75 wt % Jojoba Esters; (vii) 0.3-0.4 wt % Squalene; (viii) 0.05-0.06 wt % Phytosteryl Macadamiate; (ix) 0.01-0.02 wt % Phytosterols; (x) 0.0045 wt % Tocopherol; (xi) 1-2 wt % C18-36 Acid Triglyceride; (xii) 0.4-0.5 wt % C12-18 Acid Triglyceride; (xiii) 0.03-0.04 wt % *Ipomoea batatas* root extract; (xiv) 0.003-0.004 wt % citric acid; (xv) 0.03-0.04 wt % *Acacia senegal* gum; and (xvi) 0.03-0.04 wt % Maltodextrin.

In some embodiments, the skin barrier protective delivery system of the present disclosure comprises (i) 25-60 wt % Petrolatum; (ii) 10-25 wt % zinc oxide (ZnO); and (iii) 30-60 wt % Isohexadecane.

In some embodiments, the skin barrier protective delivery system of the present disclosure comprises (i) 40 wt % Petrolatum; (ii) 15 wt % zinc oxide (ZnO); and (iii) 45 wt % Isohexadecane.

In some embodiments, other long chain Alkanes can be used in place of Coconut Alkanes to dissolve Petrolatum. In some embodiments, long chain Alkanes can have a carbon length greater than 10 carbons, for example 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 carbons, or even greater. In some embodiments, the long chain Alkanes comprise from 10 to 40 carbon atoms, for example 10-25, 10-20, 10-15, 20-30, 25-30, 30-35, 35-40 and the like.

In some embodiments, esters of long chain Alcohols and carboxylic acids (e.g., fatty acids) can be used in place of Coco-Caprylate/Caprate to dissolve Petrolatum. For examples, the esters can comprise long chain alcohols having a carbon length greater than 10 carbons, for example 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 carbons, or even greater. In some embodiments, the long chain alcohol comprises from 10 to 40 carbon atoms, for example 10-25, 10-20, 10-15, 20-30, 25-30, 30-35, 35-40 and the like. Carboxylic acids can comprise from about 10 to about 30 carbon atoms. Suitable carboxylic acids are fatty acids including saturated and non-saturated fatty acids. Non-limiting examples of fatty acids include oleic, linoleic, palmitic, stearic, docosahexaenoic acid (DHA), and eicosapentaenoic acid (EPA). Unsaturated 18-carbon fatty acids with double bonds occurring at C9-C10 (oleic acid); at C9-C10 and C12-C13 (linoleic acid); and at C9-C10, C12-C13, and C15-C16 (linolenic acid) can also be used.

In some embodiments, the present disclosure provides a skin barrier protective delivery system comprising: (i) a mixture of long chain Alkanes having a carbon length greater than 10 carbons at a concentration range of 30-70 wt %; and (ii) petrolatum, wherein the petrolatum is present at a concentration of at least 30 wt %, wherein the delivery system is sprayable.

In some embodiments, the present disclosure provides a skin barrier protective delivery system comprising (i) a mixture of long chain Alkanes having a carbon length greater than 10 carbons at a concentration range of 30-70 wt % and esters of long chain alcohols at a concentration of 3-7 wt %; and (ii) petrolatum, wherein the petrolatum is present at a concentration of at least 30 wt %, wherein the delivery system is sprayable.

Active Ingredients

A variety of functional ingredients, including natural, including plant- and algal-derived ingredients, as well as active pharmaceutical ingredients, can be incorporated in the skin barrier protective delivery systems of the present disclosure.

"Active ingredients" may be incorporated (i.e., included) in the skin barrier protective delivery system of the present disclosure at a concentration ranging from about 0.001% to about 20%, from about 0.005% to about 10% by weight, from about 0.01% to about 5% by weight, or from about 0.1% to about 2.0%, and include: agents for the treatment of inflammatory dermatosis (including, but not limited to, acne, eczema, psoriasis, rosacea, and from radiation exposure), both steroidal and non-steroidal; anti-microbial and anti-fungal actives; anti-itch agents; topical anesthetics; sunscreens; emollients and skin soothing agents; humectants and moisturizing agents, including hyaluronic acid; skin barrier protectants (as defined in the U.S. FDA OTC Final Monograph); lipids, including vegetal-derived oils and butters; antioxidants and agents that reduce the appearance of fine lines and wrinkles, including vitamins, proteins and peptides; skin bleaching and lightening agents; agents that contribute to wound healing/wound cosmesis; agents that reduce inflammation (including erythema) and/or edema; active pharmaceutical ingredients (over-the-counter or prescription) that prevent or treat (or help prevent or treat) a pathophysiological condition (e.g., disease), including but not limited to ulcerated skin.

One non-limiting "active" ingredient that is included in the skin barrier protective delivery system of the present disclosure is *Ipomoea batatas* Root Extract, which when applied in accordance with the present disclosure has been shown to reduce edema in extremities. *Ipomoea batatas* root extract can be present in the compositions of the present disclosure in the range of 0.01-0.1 wt %. In some embodiments, *Ipomoea batatas* root extract is present in a concentration range of about 0.01-0.9 wt %, about 0.01-0.85 wt %, about 0.01-0.8 wt %, about 0.01-0.75 wt %, about 0.01-0.7 wt %, about 0.01-0.65 wt %, about 0.01-0.6 wt %, about 0.01-0.55 wt %, about 0.01-0.5 wt %, about 0.01-0.45 wt %, about 0.01-0.4 wt %, about 0.01-0.35 wt %, about 0.01-0.3 wt %, about 0.01-0.25 wt %, about 0.01-0.2 wt %, about 0.01-0.15 wt %, about 0.01-0.1 wt %, about 0.01-0.02 wt %, about 0.02-0.03 wt %, about 0.03-0.04 wt %, about 0.04-0.05 wt %, about 0.05-0.06 wt %, about 0.06-0.07 wt %, about 0.07-0.08 wt %, about 0.08-0.09 wt %, or about 0.09-0.1 wt % based on the weight of the formulation. In some embodiments, the skin barrier protective delivery system of the present disclosure is applied by spraying or misting. In one embodiment, the skin barrier protective delivery system of the present disclosure has a viscosity (TE@10) of from about 500 cps to 10,000 cps. In one embodiment, the skin barrier protective delivery system of the present disclosure has a viscosity (TE@10) of from about 1,000 cps to 5,000 cps.

In some embodiments, it has been unexpectedly discovered that the skin barrier protective delivery system of the present disclosure can be formulated as a gel that has sprayable properties. In some embodiments, the skin barrier protective delivery system of the present disclosure can be formulated as a liquid or gel-like composition that has sprayable properties. It has been discovered that the petrolatum-containing composition yields a gel-like mixture that is sprayable through, e.g., an atomizer (a fine sprayer typically used to create fine mists of fragrances). In some embodiments, no pressure (i.e., aerosol or bag-on-valve) is needed in order to spray the gel.

In some embodiments, the present disclosure provides pharmaceutical composition in the form of a sprayable gel, comprising the skin barrier protective delivery system of the present disclosure. In some embodiments, the composition does not comprise a propellant, aerosol or bag-on-valve.

In some embodiments, the compositions of the present disclosure do not contain a flammable component. In some embodiments, the compositions of the present disclosure are free of a flammable solubilizer. In some embodiments, the compositions of the present disclosure are free of an alcohol.

In some embodiments, the present disclosure provides a device comprising the skin barrier protective delivery system of the present disclosure. In some embodiments, the present disclosure provides a device comprising a pharmaceutical composition, the pharmaceutical composition comprising the skin barrier protective delivery system in the present disclosure. In some embodiments, the device does not comprise a propellant. In some embodiments, the device does not comprise an aerosol. In some embodiments, the device does not comprise a bag-on-valve. In some embodiments, the device is in the form of an atomizer pump. In some embodiments, the device is a dip tube atomizer pump.

Devices that may be used for spraying or misting include pump sprays, trigger sprays, atomizers, aerosol containers (pressurized with a propellant, for example a non-fluorocarbon propellant, including bag-on-valve dispensers). In some embodiments, spray compositions of the present disclosure can be applied directly to a skin of a subject using a device. The device can be, for example, a metering atomizing spray pump, e.g., a single, bi-dose or multiuse spray device. In some embodiments, the device does not contain a propellant.

Numbers used in describing quantities of ingredients are to be understood as being modified in all instances by the term "about."

Unless otherwise indicated, percentages are to be understood as based upon the total weight of the skin barrier protective delivery system.

Numerical ranges are meant to include numbers within the recited range, and combinations of subranges between, the given ranges. For example, a range from 1-5, includes 1, 2, 3, 4 and 5, as well as subranges such as 2-5, 3-5, 2-3, 2-4, 1-4, etc.

"At least one" means one or more, and also includes individual components as well as mixtures/combinations.

The disclosed compositions can also function as a base for the delivery of other therapeutic agents, and when so used, will enhance the clinical response to such agents.

Examples of these other therapeutic agents are:

(1) Anti-inflammatory agents, examples of which are corticosteroids, colchicine, sulfasalazine, and sulfones;

(2) Antibiotics, examples of which are quinolones, macrolides, penicillins, cephalosporins, sulfonamides, and tetracyclines;

(3) Antivirals, examples of which are acyclovir, idoxuridine, zidovudine, ddI, vidarabine, and trifluridine;

(4) Antifungals, examples of which are ketoconazole, econazole, griseofulvin, cicloprix, and naftidine;

(5) Antihistamines, examples of which are diphenhydramine, astemizole, hydroxyzine, doxepin, amitriptyline, cyproheptadine, and sodium cromolyn;

(6) Antipruritics, examples of which are camphor, menthol, phenol, benzocaine, benzyl alcohol, salicylic acid, dyclonine, and pramoxine;

(7) Antineoplastic agents, examples of which are methotrexate, piritrexim, cisplatin, 5-fluorouracil, bleomycin, carmustine, hydroxyurea, azathioprine, and nitrogen mustard;

(8) Carboxylic acid analogs, examples of which are 1-monolaurin, azelaic acid and dodecanedioic acid;

(9) Natural and synthetic vitamins and analogs, examples of which are vitamin D, calcipitriol, 1,25-dihydroxy cholecalciferol, retinol, retinyl palmitate, retinyl ascorbate, isotretinoin, etretinate and retinoic acid; and

(10) Artemisinin analogs, examples of which are artesunate, arteether, artemether, dihydroartemisinin and artelenic acid;

The concentrations of these therapeutic ingredients may vary. A typical range is from about 0.01% to about 10%. The most appropriate concentration will depend on the clinical indication and will be apparent to those skilled in the art.

6. PHARMACEUTICAL FORMULATIONS

Other cosmetic and/or pharmaceutical agents or excipients can be provided in the formulations of the present disclosure, so long as they are non-toxic and physiologically acceptable and suitable for use in combination with the therapeutically effective amount of an active ingredient provided in the formulations.

For example, the claimed formulations of the present disclosure can include chemically compatible pharmaceutically acceptable vehicles and excipients such as water and/or alcohol. The formulations can also include emollients, such as petrolatum, zinc oxide, paraffin, mineral oil, glycerin, beeswax, olive oil, coconut oil, jojoba oil, lanolin, cocoa butter, butyl stearate, stearic acid, di-glycol laurate, 2-ethylhexanol, almond butter, aloe vera gel, batana oil, caprylic/capric triglyceride, caprylyl-caprylate/caprate, cetyl palmitate, chia seed oil, coco-caprylate, collodion, dhupa butter, dicaprylyl carbonate, dihydroxyacetone, dimethicone, myristates, shea butter, plant oils, fatty acids, fatty alcohols, triglycerides, benzoates, palmitates, squalene and ceramides, derivatives, combinations and mixtures thereof. The compositions can include skin conditioning agents, such as butyl alcohol, cholesterol, lanolin, fatty acid esters, fatty acid ethers, cetyl acetate, silicones, plant oils, panthenol, panthenol triacetate, vitamin B, vitamin C, vitamin D, vitamin E, vitamin D, keratin, lysine, arginine, hydrolyzed wheat proteins, hydrolyzed silk proteins, colloidal oatmeal, zinc, coal tar, hydrocortisone, sulfides, emollients, derivatives, combinations and mixtures thereof.

The formulations can include pH adjusting agent(s), such as alpha-hydroxy acids, buytlated hydroxy toluene (BHT), ethylene diamine tetra-acetic acid (EDTA), triethanolamine (TEA), cosmetics salts, glycerine, propylene glycol and derivatives, combinations and mixtures thereof.

Other acceptable ingredients include humectants, such as glycerine, propylene glycol, sorbitol, hexylene glycol, butylene glycol, urea, alpha-hydroxy acids, polyhydric alcohols, sorbital, hydroxypropyl sobitol, hexylene glycol, 1-3 dibutylene glycol, 1,2,6-hexanetriol, ethoxylated glycerol, propoxylated glycerol, and derivatives, combinations and mixtures thereof can be incorporated herein. Pharmaceutical acceptable buffering agents, such as citric acid, sodium citrate, their derivatives, combinations and mixtures thereof are also useful beneficial.

Other components that can be included are viscosity adjusting agents, such as salts, carbomer gelling agents, gum derivatives, and derivatives, combinations and mixtures thereof. Preservatives, such as methylparaben, ethylparaben, butylparaben, formaldehyde, DMDM hydantoin, leucidal liquid, propylparaben, phenoxyethanol and derivatives, combinations, and mixtures thereof are also useful in small amounts. The inventive formulations can include emulsifying agents, such as polysorbate 80, glyceryl disterate, POE (2) stearyl ether, POE 10 stearyl ether, ceateareth 20, stearyl alcohol, ceteareth 20, cetearyl alcohol, lecithin and derivatives, combinations and mixtures thereof. For example, the inventive formulations my include chelating agents such as ethylenediamine tetra acetic acid (EDTA), dihydroxyethyl glycine, tartaric acid, derivatives, combination, and mixtures thereof. These formulations may also include thickening agents, such as salt, silica, bentonite, magnesium aluminum silicate, carbomer, gum, xanthan gum, gelatin, cetyl alcohol, stearyl alcohol, carnauba wax, stearic acid, polyacrylamide, C13-C14 isoparafin, laureth-, and derivatives, combinations and mixtures thereof.

Additional optional elements of the formulations of the present disclosure include antioxidants, such as green tea extract, ascorbyl palmitate, tocopheryl acetate, BHT, BHA, alpha lipoic acid, beta-glucan, coenzyme Q10, grape seed extract, green tea, soybean sterols, superoxide dismutase, vitamin C (ascorbyl palmitate and magnesium ascorbyl palmitate), and vitamin E (alpha tocopherol, tocotrienols, tocopherol acetate), pomegranate, curcurmin, turmeric, butylated hydroanisole (BHA), phenyl-naphthylamine, hydroquinone, propyl gallate, melatonin, nordihydroquiaretic acid, and derivatives, combinations and mixtures thereof.

The formulations of the present disclosure can also include anti-aging agents, such as agents for treating wrinkles or preventing development thereof. Anti-ageing, anti-wrinkle, anti-skin atrophy and skin repair actives can be effective in replenishing or rejuvenating the epidermal layer. These ingredients generally provide desirable skin care benefits by promoting or maintaining the natural process of desquamation. Examples of anti-wrinkle and anti-skin atrophy actives include those selected from one or more of the list consisting of: alpha-lipoic acid, lycopene, ergothioneine, resveratol, grape seed extract, cis-urocaninic acid (see U.S. Pat. No. 5,620,680), compositions containing farnesol and/or bisabolol (see PCT Publication No. WO 00/62744), 2-amino-1,3-alkanediols, including but not limited to, 2-amino-1,3-octadecanediol, 2-N-acetylamino-1,3-octadecanediol, 2-N-octanoylamino-1,3-octadecanediol, 2-N-(2-hydroxyhexadecanoyl)amino-1,-3-octadecanediol, 2-N-(2-hydroxydocosanoyl)amino-1,3-octadecanediol, 2-amino-1, 3,4-octadecanetriol, 2-N-(2-hydroxyhexadecanoyl)amino-1, 3,4-oct-adecanetriol, 2-N-hexanoylamino-1,3-octadecanediol, 2-N-octanoylamino-1,3,4-octadecanetriol (see U.S. patent Publication No. 2002/0006420 to Philippe et al.), ubiquinones and plastoquinones (coenzymes Qn), particularly coenzymes. Q9 and Q10, prasterone, DHEA, dehydroepiandrosterone, formulations containing one or more compounds chosen from the group consisting of sterols (such as zoosterols including cholesterol, dihydrocholesterol, 7-dehydrocholesterol, lanosterol, dihydrolanosterol, spongosterol and stellasterol, phytonterols including ergosterol, sitosterol, stigmasterol, fucosterol, brassicasterol and campesterol, mycosterols including ergosterol, fungisterol and zymosterol) and biochemical precursors thereof (such as mevalonic acid, famesol and squalane) in combination with one or more compounds including ubiquinones and derivatives thereof and plastoquinones and derivatives thereof (see U.S. Pat. No. 6,261,575), bertholletia extracts, betulinic acid, biotin, blackberry bark extract, blackberry lily extracts, black cohosh extract, blue cohesh extract, butanoyl betulinic acid, carboxymethyl 1,3 beta glucan, chalcones, chaste tree extract, clover extracts, coumestrol, daidzein, dang gui extract, darutoside, debromo laurinterol, 1-decanoyl-glycero-phosphonic acid, dehydrodicreosol, dehydrodieugenol, dehydroepiandrosterone, dehydroepiandersterone sulfate, dianethole, diosgenin, dodecanedioic acid, ergosterol, fennel extract, fenugreek seed extract, formononetin, forsythia fruit extract, genistein, genisteine, genistic acid, gentisyl alcohol, gingko bilboa extracts, ginseng extracts, ginsenoside, 25-hydroxycholesterol, 7-hydroxylated sterols, hydroxyethyl isostearyloxy isopropanolamine, hydroxytetra methyl piperidinyloxy, hypotaurine, ibukijakou extract, isoflavones, isoflavone SG 10 (available from Barnet Products), kinetin, kohki extract, lectins, lichochalcone LF15 (available from Maruzen), licorice extracts, lignan, lumisterol, lupenes, luteolin, lysophosphitidic acid, naringenin, neotigogenin, o-desmethylangoiensin, oat beta glucan, oleanolic acid, placental extracts, pratensein, pregnenolone, pregnenolone acetate, pregnenolone succinate, soya extracts, spleen extracts, tachysterol, tigogenin, vitex extract, yam extract, yamogenin, zeatin, hyaluronic acid.

The formulations of the present disclosure can also include anti-acne agents selected from one or more of the list consisting of: phenoxyethanol, phenoxypropanol, phenoxyisopropanol, ethyl acetate, sebostats such as flavonoids and bioflavonoids; bile salts such as scymnol sulfate and its derivatives, deoxycholate, and cholate; allantoin; aloe extracts; barberry extracts; bearberry extracts; *Belamcanda chinensis*; berberine; BIODERMINE (available from Sederma); bioflavinoids; bisabolol; carrot extracts; cassin oil; clove extracts; citral; citronellal; cucumber extracts; ethyl hexyl monoglyceryl ether; ethyl 2-hydroxy undecanoate; farnesol; farnesol acetate; geranoil; glabridin; glyceryl monocaprate; grapefruit seed extract; gugu lipid; hesperitin; hinokitol; hops extract; hydrogenated rosin; lemon grass oil; linoleic acid; LIPACIDE C8CO (available from Seppic,); mukurossi; neem seed oil; panthenol; 1-pentadecanol; peonia extract; peppermint extract; phelladendron extract; phloretin; PHLOROGINE (available from Secma); quercetin; red sandalwood extract; rosemary extract; rutin; sage extract; skull cap extract; siber hegner extract; siberian saxifrage extract; *Sophora* Extract (available from Maruzen); sunder vati extract; tea tree oil; thyme extract; trehalose 6-undecylenoate; 3-tridecene-2-ol; triclosan; white thyme oil; willow bark extract; wogonin; Ylang Ylang; zinc glycerolate; zinc linoleate; zinc oxide; zinc pyrithione; zinc sulfate; urea; triclosan, phenoxy ethanol and phenoxy proponol, ethylacetate, chlorhexidine and its derivatives such as chlorhexidine gluconate; sebostats such as flavinoids, prasterone, and antiseptic type antimicrobial agents and disinfectant type antibacterial agents such as chlorxylenol, chloroxylenol, octowynol and nonoxynol (see Martindale The Extra Pharmacopoeia 29$^{th}$ Edition), urea, allantoin, povidone-iodine and phenol.

Lip balms compositions can comprise behenic acid or acexaminc acid, and antiseptic type antimicrobial agents and disinfectant type antibacterial agents such as chlorxylenol, chloroxylenol, octowynol and nonoxynol (see Martindale The Extra Pharmacopoeia 29$^{th}$ Edition), urea, allantoin, povidone-iodine and phenol, menthol, camphor, triclosan, phenoxy ethanol, phenoxy proponol, ethylacetate, chlorhexidine and its derivatives such as chlorhexidine gluconate.

The formulations of the present disclosure can also include skin conditioning agents such as agents that smooth or soften the skin, selected from one or more of the list consisting of aloe vera extracts, Biocare SA (available from Amerchol); egg albumen; Flexan 130 (available from National Starch); Gatuline Lifting (available from Gattefosse); Pentacare HP (available from Pentapharm); Vegeseryl (available from Laboratories Serobioloques), candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*).

The formulations of the present disclosure can also include skin barrier repair ingredients which can help repair and replenish the natural moisture barrier function of the epidermis. Non-limiting examples of skin barrier repair actives include Alpha Lipid (available from Lucas Meyer); biotin; biotin esters; brassicasterol; caffeine; campesterol; canola derived sterols; Cennamides (available from Ennagram); Ceramax (available from Alban Muller); CERAMAX, (available from Quest, located in Ashford, England); CERAMIDE 2 and CERAMIDE HO3™ (both available from Sederma); CERAMIDE II (available from Quest); CERAMIDE III and IIIB (both available from Cosmoferm, located in Deft, Netherlands); CERAMIDE LS 3773 (available from Laboratories Serobiologiques); CERAMINOL (available from Inocosm); Cerasol and Cephalip (both available from Pentapharm); cholesterol; cholesterol hydroxystearate; cholesterol isostearate; 7 dehydrocholesterol; DERMATEIN BRC and, DERMATEIN GSL (both available from Hormel); ELDEW CL 301 AND ELDEW PS 203 (both available from Ajinomoto); Fitobroside (available from Pentapharm); galactocerebrosides; Generol, 122 (available from Henkel); glyceryl serine amide; hydroxyethyl isostearyl isopropanolamine; lanolin; lanolin alcohols; lanosterol; lauric acid N laurylglucamide; lipoic acid; N-acetyl cysteine; N-acetyl-L-serine; N-methyl-L-Serine; Net Sterol-ISO (available from Barnet Products); palmitic acid; panthenol; panthetine; PHYTOSPHINGOSINE (available from Gist Brocades, located in King of Prussia, Pa.); PSENDOFILAGGRIN (available from Brooks Industries, located in South Plainfield, N.J.); QUESTAMIDE H (available from Quest); serine; sigmasterol; sitosterol; soybean derived sterols; sphingosine; sphingomylinase; S-lactoyl glutathione; stearic acid; Structurine (available from Silah); SUPER STEROL ESTERS (available from Croda); thioctic acid; THSC CERAMIDE OIL (available from Campo Research); trimethyl glycine; tocopheryl nicotinate; vitamin D$_3$; and Y2 (available from Ocean Pharmaceutical).

The formulations of the present disclosure can also include sebum stimulators that can increase the production of sebum by the sebaceous glands. These skin care actives are especially useful for post-menopausal women who are sebum deficient. Examples of sebum stimulating actives include bryonolic acid, completech MBAC-DS, dehydroepiandrosterone (also known as DHEA), orizanol and mixtures thereof.

The formulations of the present disclosure can also include sebum inhibitors that can decrease the production of sebum by the sebaceous glands. Examples of sebum inhibiting actives include aluminium hydroxy chloride, ASEBIOL (available from Laboratories Serobiologiques), BIODERMINE (available from Sederma), cucumber extracts, gugulipiu, Lichochalcone LR 15 (available from Maruzen), phloretin, PHLOROGINE (available from Seema), S-carboxylmethyl cysteine, sepicontrol AS, zincidone (UC1B), and mixtures thereof.

The formulations of the present disclosure can also include moisturizing agent selected from the group consisting of: glycerol, propylene glycol, dipropylenen glycol, butylene glycol, sorbitol, honey and honey derivatives such as honeyquat, urea and urea derivatives such as hydroxyethyl urea, ammonium lactate, sodium lactate, potassium lactate, pyroglutamic acid and its salts, sodium malates, polydextrose, triacetin, mannitol, oxidised polyethylene, isomalt, maltitol and maltitol syrup, lactitol, xylitol, erythrit, and combinations thereof.

The formulations of the present disclosure can also include a pharmaceutically acceptable carrier, which can be any cosmetic vehicle that is toxicologically and pharmaceutically acceptable. Typical pharmaceutically acceptable carriers that can be used in compositions of the present disclosure include water, ethanol, acetone, isopropyl alcohol, stearyl alcohol, freons, polyvinyl pyrrolidone, propylene glycol, polyethlyene glycol, fragrances, gel-producing materials, mineral oil, stearic acid, spermaceti, sorbitan, monoleate, polysorbates, "Tweens," sorbitol, methyl cellulose, petrolatum, a mineral oil (vaseline oil), which may be any petroleum based product; modified or unmodified vegetable oils such as peanut oil, wheatgerm oil, linseed oil, jojoba oil, apricot kernel oil, walnut oil, palm oil, pistachio oil, sesame oil, colza oil, cade oil, corn germ oil, peach kernel oil, poppyseed oil, pine oil, castor oil, soya oil, safflower oil, coconut oil, hazelnut oil, grapeseed oil, avocado oil, soy oil, sweet almond oil, calophyllum oil, castor oil, olive oil, sunflower oil, or animal oils such as whale oil, seal oil, menhaden oil, halibut liver oil, cod liver oil, cod, tuna, turtle tallow, horse's hoof, sheep's foot, mink, otter, marmot oil and the like; synthetic oils such as silicon oil such as dimethylpolysiloxane; alkyl and alkenyl esters of fatty acids, such as isopropyl esters of myristic, palmitic and stearic acids and fatty esters which are solid at room temperature; waxes such as lanolin wax, candelilla wax, spermaceti, cocoa butter, karite butter, silicon waxes, hydrogenated oils which are solid at room temperature, sucro-glycerides, oleates, myristates, linoleates, stearates, paraffin, beeswax, carnauba wax, ozokerite, candelilla wax, microcrystalline wax; fatty alcohols such as lauryl, cetyl, myristyl, stearyl, palmityl and oleyl alcohols; polyoxyethylated fatty alcohols; and wax esters, lanolin and its derivatives, perhydrosqualene and saturated esters, ethyl palmitate, isopropyl palmitate, alkyl myristates such as isopropyl myristate, butyl myristate and decyl myristate, hexyl stearate, triglyceride esters, triglycerides of octanoic and decanoic acid, cetyl ricinoleate, stearyl octanoate (Purcellin oil), fatty acids, polyhydric alcohols, polyether derivatives, fatty acid monoglycerides, polyethylene gylcol, propylene glycol, alkyl ethoxy ether sulfonates, ammonium alkyl sulfates, fatty acid soaps, and hydrogenated polyisobutene, and mixtures of waxes and oils.

The formulations of the present disclosure can also include a solvent. In some embodiments, the solvent is selected from the group consisting of water, ethanol, isopropyl alcohol, water, dimethyl ether, diethyl ether, butane, propane, isobutene, 1,1, difluoroethane, 1,1,1,2 tetrafluorethane, 1,1,1,2,3,3,3-heptafluoropropane, 1,1,1,3,3,3 hexafluoropropane, ethyl acetate, acetone, iso-amyl acetate, denatured alcohol, methanol, propanol, isobutene, pentane, hexane, chlorobutanol, turpentine, cytopentasiloxane, cyclomethicone, methyl ethyl ketone, and combinations thereof. In other embodiments, the solvent is selected from the group consisting of 1,2,6-hexanetriol, alkyltriols, alkyldiols, acetyl monoglycerides, tocopherol, alkyl dioxolanes, p-propenylanisole, anise oil, apricot oil, dimethyl isosorbide, alkyl glucoside, benzyl alcohol, bees wax, benzyl benzoate, butylene glycol, caprylic/capric triglyceride, caramel, cassia oil, castor oil, cinnamaldehyde, cinnamon oil, clove oil, coconut oil, cocoa butter, cocoglycerides, coriander oil, corn oil, coriander oil, corn syrup, cottonseed oil, cresol, cyclomethicone, diacetin, diacetylated monoglycerides, diethanolamine, dietthylene glycol monoethyl ether, diglycerides, ethylene glycol, *eucalyptus* oil, fat, fatty alcohols, flavors, liquid sugars, ginger extract, glycerin, high fructose corn syrup, hydrogenated castor oil, IP palmitate, lemon oil, lime oil, limonene, milk, monoacetin, monoglycerides, nutmeg oil, octyidodecanol, olive alcohol, orange oil, palm oil, peanut oil, PEG vegetable oil, peppermint oil, petrolatum, phenol, pine needle oil, polypropylene glycol, sesame oil, spearmint oil, soybean oil, vegetable oil, vegetable shortening, vinyl acetate, wax, 2-(2-(octadecyloxy)ethoxy)ethanol, benzyl benzoate, butylated hydroxyanisole, candelilla wax, carnauba wax, ceteareth-20, cetyl alcohol, polyglyceryl, dipolyhydroxy stearate, PEG-7 hydrogenated castor oil, diethyl phthalate, diethyl sebacate, dimethicone, dimethyl phthalate, PEG fatty acid esters, PEG-stearate, PEG-oleate, PEG laurate, PEG fatty acid diesters, PEG-dioleate, PEG-distearate, PEG-castor oil, glyceryl behenate, PEG glycerol fatty acid esters, PEG glyceryl laurate, PEG glyceryl stearate, PEG glyceryl oleate, hexylene glycerol, lanolin, lauric diethanolamide, lauryl lactate, lauryl sulfate, medronic acid, methacrylic acid, multisterol extract, myristyl alcohol, neutral oil, PEG-octyl phenyl ether, PEG-alkyl ethers, PEG-cetyl ether, PEG-stearyl ether, PEG-sorbitan fatty acid esters, PEG-sorbitan diisosterate, PEG-sorbitan monostearate, propylene glycol fatty acid esters, propylene glycol stearate, propylene glycol, caprylate/caprate, sodium pyrrolidone carboxylate, sorbitol, squalene, stear-o-wet, triglycerides, alkyl aryl polyether alcohols, polyoxyethylene derivatives of sorbitan-ethers, saturated polyglycolyzed C8-C10 glycerides, N-methyl pyrrolidone, honey, polyoxyethylated glycerides, dimethyl sulfoxide, azone and related compounds, dimethylformamide, N-methyl formamaide, fatty acid esters, fatty alcohol ethers, alkyl-amides (N,N-dimethylalkylamides), N-methyl pyrrolidone related compounds, ethyl oleate, polyglycerized fatty acids, glycerol monooleate, glyceryl monomyristate, glycerol esters of fatty acids, silk amino acids, PPG-3 benzyl ether myristate, Di-PPG2 myreth 10-adipate, honeyquat, sodium pyroglutamic acid, abyssinica oil, dimethicone, macadamia nut oil, limnanthes alba seed oil, cetearyl alcohol, PEG-50 shea butter, shea butter, aloe vera juice, phenyl trimethicone, hydrolyzed wheat protein, and combinations thereof.

When present, the solvent can be present a concentration of about 0.01-25 wt %, 0.01-20 wt %, 0.01-15 wt %, 0.01-10 wt %, about 0.01-5 wt %, about 0.01-1 wt %, 0.1-25 wt %, 0.1-20 wt %, 0.1-15 wt %, 0.1-10 wt %, about 0.1-5 wt %, about 0.1-1 wt %, about 0.5-1 wt %, about 0.01-0.05 wt %, about 0.05-0.1 wt %, about 0.1-0.15 wt %, about 0.15-0.2 wt %, about 0.2-0.25 wt %, about 0.25-0.3 wt %, about 0.3-0.35 wt %, about 0.35-0.4 wt %, or about 0.4-0.45 wt %, about 0.45-0.5 wt %, about 0.5-0.55 wt %, about 0.55-0.6 wt %, about 0.6-0.65 wt %, about 0.65-0.7 wt %, about 0.7-0.75 wt %, about 0.75-0.8 wt %, about 0.8-0.85 wt %, about 0.85-0.9 wt %, about 0.9-0.95 wt %, about 0.95-1 wt %, about 1-1.5 wt %, about 1.5-2 wt %, about 2-3 wt %, about 3-4 wt %, about 4-5 wt %, about 5-6 wt %, about 6-7 wt %, about 7-8 wt %, about 8-9 wt %, about 9-10 wt %, about 10-15 wt %, about 15-20 wt %, or about 20-30 wt %, based on total weight of the formulation.

The formulations of the present disclosure can include nutrients and amino acids such as alanine, arginine, asparagine, aspartic acid, cysteine, cystine, glutamic acid, glutamine, glycine, histidine, isoleucine, leucine, lysine, methionine, phenylalanine, proline, serine, threonine, tryptophan, tyrosine, valine, minerals and vitamin A, vitamin B, vitamin C, vitamin D, vitamin E, vitamin K, and derivatives, combinations, and mixtures thereof. the inventive formulations may include fragrances, such as *eucalyptus* oil, camphor synthetic, peppermint oil, clove oil, olive oil, lavender, chamomile, flavor fragrances such as chocolate, vanilla, mint, derivatives, combinations and mixtures thereof. The formulations of present disclosure can also include other food additives commonly contained in supplements such as gelatin, rice, flour, wheat, citric acid, natural and artificial flavors, derivatives, combinations and mixtures thereof.

The formulations may also include antioxidant ingredients and compositions selected from, but not limited to, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), α-Lipoic acid, Niacinamide lipoate, Glutathione, Andrographolide (*Andrographis paniculata*), Carnosine, Niacinamide, *Potentilla erecta* extract, Polyphenols, Grapeseed extract, Pycnogenol (Pine Bark extract), Pyridoxine, Magnolol, Honokiol, Paeonol, Resacetophenone, Quinacetophenone, arbutin, kojic acid, and combinations thereof. The antioxidants can be present, individually or cumulatively, in a concentration of about 0.001-0.01 wt %, about 0.01-0.05 wt %, about 0.05-0.1 wt %, about 0.1-0.15 wt %, about 0.15-0.2 wt %, about 0.2-0.25 wt %, about 0.25-0.3 wt %, about 0.3-0.35 wt %, about 0.35-0.4 wt %, or about 0.4-0.45 wt % to any of about 0.45-0.5 wt %, about 0.5-0.55 wt %, about 0.55-0.6 wt %, about 0.6-0.65 wt %, about 0.65-0.7 wt %, about 0.7-0.75 wt %, about 0.75-0.8 wt %, about 0.8-0.85 wt %, about 0.85-0.9 wt %, about 0.9-0.95 wt %, about 0.95-1 wt %, about 1-1.5 wt %, about 1.5-2 wt %, about 2-3 wt %, about 3-4 wt %, about 4-5 wt %, about 5-6 wt %, about 6-7 wt %, about 7-8 wt %, about 8-9 wt %, about 9-10 wt %, about 10-15 wt %, about 15-20 wt %, or about 20-30 wt %, based on total weight of the formulation.

The formulations can also include blood micro-circulation improvement ingredients and compositions selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Ginger Root Extract (*Zingiber officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), Amni visnaga extract, extract of Red Vine (*Vitis vinifera*) leaves, apigenin, phytosan, luteolin, and combinations thereof.

The formulations can also include anti-inflammatory ingredients or compositions selected from, but not limited to, at least one antioxidant class of Cyclo-oxygenase (for example, COX-1 or COX-2) or Lipoxygenase (for example, LOX-5) enzyme inhibitors such as Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, and Emblica extract. Anti-inflammatory composition can additionally be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Sericoside, Visnadine, Thiocolchicoside, Grapeseed Extract, Ginger Root Extract (*Zingiber officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), Amni visnaga extract, extract of Red Vine (*Vitis-Vinifera*) leaves, apigenin, phytosan, luteolin, and combinations thereof.

Certain divalent and polyvalent metal ions can also be present in the compositions of the present disclosure. The examples of such metal ions include zinc, copper, manganese, vanadium, chromium, cobalt, and iron.

The formulations can also include colorants, such as zinc oxide (white), titanium dioxide (white), calcium carbonate, kaolin, blue, green, orange, red, violet, yellow and black pigments. The formulations may also include mixtures and combinations of any of the above, as well as one or more active ingredients in addition to the therapeutically effective dose of an active ingredient, for example and without limitation, other therapeutic agents for the prevention and treatment of one or more conditions or disease states.

The formulations of the present disclosure can also include skin whitening agent is selected from the group consisting of hydroquinone, arbutin, hydroquinone derivatives, Paper Mulberry extract (*Broussonetia kazinoke*), Mitracarpe extract (*Mitracarpus scaber*), Bearberry extract (*Arctostaphylos uva ursi*), Yellow Dock extract (*Rumex crispus* and *Rumex occidentalis*), Glutathione, Leucocyte extract, *Aspergillus orizae* extract (*Aspergillus orizae*), Licorice Root extract (*Glycyrrhiza glabra*), Rosmarinic acid (*Rosmarinus officinalis*), Tetrahydrocurcumin, Green Tea extract (*Camellia sinensis*), Yohimbe extract (*Pausinystalia yohimbe*), Ecklonia cava extract, niacinamide, Hydroxytetronic acid, *Spondias mombin* extract, *Maprounea guianensis* extract, *Walteria indica* extract, *Gouania blanchetiana* extract, *Cordia schomburgkii* extract, *Randia armata* extract, *Hibiscus furcellatus* extract, 2-hydroxyacetophenone, 3-hydroxyacetophenone, 4-hydroxyacetophenone, 2,3-dihydroxyacetophenone, 2,4-dihydroxyacetophenone, 2,5-dihydroxyacetophenone, 2,6-dihydroxyacetophenone, 3,4-dihydroxyacetophenone, 3,5-dihydroxyacetophenone, 2,4,6-trihydroxyacetophenone, 2,3,4-trihydroxyacetophenone, 2,3,5-trihydroxyacetophenone, 2,3,6-trihydroxyacetophenone, 2,4,5-trihydroxyacetophenone, 3,4,5-trihydroxyacetophenone, Resacetophenone, 2-Acetyl resorcinol, 4-Acetyl resorcinol, 3,4-Dihydroxyacetophenone, acetyl quinol, Quinacetophenone, 1-(3-Hydroxy-4-methoxy-5-methylphenyl) ethanone, 1-(3-hydroxy-4-methoxyphenyl) ethanone, Paeonol, 5'-Bromo-2'-hydroxyacetophenone, 5'-Chloro-2'-hydroxyacetophenone, 3',5'-Dichloro-2'-hydroxyacetophenone, 3',5'-Dibromo-4'-hydroxyacetophenone, 5-Chloro-3-bromo-2-hydroxyacetophenone, and combinations thereof. The quantities of such compositions can be safe and effective amounts as needed, and not limited to any specific limits.

The formulations of the present disclosure can also include sun protecting ingredients with an SPF of 6-95. Sun protecting ingredients include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl) aminobenzoate, 2-ethylhexyl-2-cyano-3,3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this disclosure will vary depending on the specific UV absorption wavelength(s) of the specific sunscreen active(s) used and can be from about 0.1 to about 10 percent by weight, from about 2 to about 8 percent by weight. In one embodiment, the active ingredient is present in the formulations of the present disclosure at concentrations of from about 0.1% to about 60.0%. In one embodiment, the active ingredient is present in the formulations at concentrations of from about 0.1% to about 80.0%. In one embodiment, the active ingredient is present in the formulations of the present disclosure at concentrations of from about 1.0% to about 50.0% for topical and transdermal applications and at concentrations of from about 50% to 98% for oral formulations.

The formulations of the present disclosure can also include Analgesics, such as Lanocaine, lidocaine, prilocalne, salicylates, NSAIDs, acetaminophen, capsaicins, camphor, menthol, methyl salicylate, methyl nicotinate, ketamine and trolamine salicylate.

The formulations of the present disclosure can also include an agent for wound healing, such as apain, trypsin, allantoin, chymo-trypsin, streptokinase, streptodornase, ficin, pepsin, carboxypeptidase, amino-peptidase, chymopapain, and bromelin.

The formulations of the present disclosure can also include anti-infectives, such as Bacitracin, polymixin B, mupirocin, neomycin, tetracyclines (chlortetracycline hydrochloride, oxytetracycline hydrochloride and tetracycline hydrochoride), clindamycin, gentamicin sulfate, benzalkonium chloride, benzethonium chloride, hexylresorcinol, methylbenzethonium chloride, and phenol.

The formulations of the present disclosure can also include antiseptics, such as thymol, Menthol, Benzalkonium Chloride, Chlorhexidine gluconate, and natural oils including Tea Tree Oil.

The formulations of the present disclosure can also include astringents and drying agents, such as Calamine, witch hazel, sodium bicarbonate, aluminum hydroxide and zinc oxide.

The formulations of the present disclosure can also include anti-fungals, such as miconazole, econazole, tolnaftate, ketoconazole, undecylenic acid, amphotericin, carbolfuchsin, ciclopirox, clotrimzole, haloprogin, mafenide, naftifine, nystatin, oxiconazole, silver, sulfadiazine, sulconazole, terbinafine, tioconazole, undecylenic acid Anti-Acne salicylic acid, benzoyl peroxide, Acne, rosacea, seborheic resorcinol, sulfur, dermatitis sodium sulfacetamide, retinoic acid, isotretinoin, erythromycin, zinc, retinol, citric acid, and alpha hydroxy acid.

In certain embodiments, retinol is included in the delivery systems described herein and include about 0.01-10 wt %, about 0.01-5 wt %, about 0.01-4 wt %, about 0.01-3%, about 0.01-2 wt %, about 0.01-1 wt %, about 0.1-5 wt %, about 0.1-4 wt %, about 0.1-3 wt %, about 0.1-2 wt %, about 0.1-1 wt %, about 1-10 wt %, about 10-20 wt %, about 20-30 wt %, about 30-40 wt %, about 40-50 wt %, about 50-60 wt %, about 60-70 wt %, about 70-80 wt %, about 80-85 wt %, about 85-90 wt %, about 90-95 wt %, about 95-96 wt %, about 96-97 wt %, about 97-98 wt %, about 98-99 wt %, about 99-99.5 wt %, or about 99.5 wt % retinol, based on total weight of the retinol and derivatives thereof in the delivery systems described herein.

The formulations of the present disclosure can also include anti-virals, such as acyclovir, docosanol, pencyclovir, cidofovir, desciclovir, famciclovir, ganciclovir, lobucavir, PMEA, valacyclovir, 2242, PAA, PFA, H2G, sorivudine, trifluridin, tromantadine, adenine, arabinoside, arabinosyladenine-monophosphate, and lobucavir.

The formulations of the present disclosure can also include immunomodulators, such as pimecrolimus, tacrolimus, muramyl dipeptide, cyclosporins, interferons (including alpha, beta, and gamma interferons), interleukin-2, cytokines, tumor necrosis factor, pentostatin, thymopentin, transforming factor beta2, and erythropoetin.

The formulations of the present disclosure can also include cleansers, such as ammonium lauryl sulfate, cold creams, glycerin, glycolic or salicylic acid, sodium bicarbonate, calcium carbonate, magnesium hydroxide, aluminum hydroxide, sodium hydroxide, polyethylene beads, aluminum oxide, syndet cleansers, bicarbonate of soda, waxes and minerals with borax-based detergents, or a combination thereof.

In certain embodiments, the composition comprises petroleum jelly, yellow 5 lake, petrolatum, white petrolatum or a combination thereof. In certain embodiments, the petroleum is present in at a concentration of about 10-15%, 15-20%, 20-30%, 30-40%, 40-50%, 50-60%, 60-70%, 70-80%, 80-90%, 90-95%, 95-98% by weight.

In certain embodiments, the composition of the present disclosure comprises Cedarleaf Oil, Nutmeg Oil, Special Petrolatum, Thymol, Turpentine Oil, fragrance, or a combination thereof.

In certain embodiments, the composition of the present disclosure comprises Camphor 4%-5% (Cough Suppressant and Topical Analgesic) *Eucalyptus* Oil (1-5%) (Cough Suppressant) Menthol 1-5% (Cough Suppressant and Topical Analgesic), or a combination thereof.

In certain embodiments, the composition comprises Deionized Water, Glycerin, Petrolatum, Distearyldimonium Chloride, Isopropyl Palmitate, Cetyl Alcohol, Dimethicone, Allantoin, T36-C5, *Melaleuca* Oil, Benzyl Alcohol, or a combination thereof. In certain embodiments, the composition comprises Mineral Oil, Ceresin, Lanolin Alcohol, Panthenol, Glycerin, Bisabolol, or a combination thereof. In certain embodiments, the composition comprises Caprylic/Capric Triglyceride, *Persea gratissima* (Avocado) Oil, Microcrystalline Wax, Beeswax, Butyrospermum Parkii (Shea) Butter, Tocopherol, Panthenol, Glycerin, Bisabolol, or a combination thereof. In certain embodiments, the composition comprises hydrocortisone, at concentration ranges of about 0.5-1.5%, 1.5-3%, 3-5%, 5-10%, 10-15%, 15-20% by weight, based on total weight of the formulation.

In certain embodiments, the composition comprises Petrolatum, Mineral Oil, Ceresin, Lanolin Alcohol, Panthenol, Glycerin, Bisabolol, Menthoxypropanediol, or a combination thereof.

In certain embodiments, the composition comprises Bacitracin 500 units: First aid antibiotic Neomycin Sulfate 3.5 mg: antibiotic Polymyxin B Sulfate 10,000 units: First aid antibiotic Pramoxine HCI 10 mg: External analgesic, or a combination thereof.

In certain embodiments, the composition comprises Petrolatum, *Gossypium herbaceum* (Cotton) Seed Oil, *Olea europaea* (Olive) Fruit Oil, *Theobroma cacao* (Cocoa) Seed Butter, Tocopheryl Acetate, Sodium Pyruvate, or a combination thereof.

In certain embodiments, the composition comprises Camphor (w/w) (1-5%) (External Analgesic), Menthol (w/w)(1-5%) (External Analgesic), Petrolatum (w/w) 10-70% (Lip Protectant), Phenol (w/w) (0.5-1%) (External Analgesic), or a combination thereof.

In certain embodiments, the composition comprises Beeswax, Benzyl Alcohol, Diisopropyl Adipate, Flavors, Fragrances, Lanolin, Menthoxypropanediol, Microcrystalline Wax, Myristyl Myristate, *Ricinus communis* Seed Oil (Castor), Saccharin, *Theobroma cacao* (Cocoa) Seed Butter or a combination thereof.

In certain embodiments, the composition comprises Dimethicone (w/w) (1-5%, e.g., 1 wt %, 1.5 wt %, 2 wt %, 2.5 wt %, 3 wt %, 3.5 wt %, 4 wt %, 4.5 wt % or 5 wt %) (Lip protectant), Octinoxate (w/w)—(1-10%, e.g, 1 wt %, 1.5 wt %, 2 wt %, 2.5 wt %, 3 wt %, 3.5 wt %, 4 wt %, 4.5 wt % or 5 wt %, 5.5 wt %, 6 wt %, 6.5 wt %, 7 wt %, 7.5 wt %, 8 wt %, 8.5 wt %, 9 wt %, 9.5 wt % or 10 wt %) (Sunscreen), Octisalate (w/w)—(1-5%, e.g, 1 wt %, 1.5 wt %, 2 wt %, 2.5 wt %, 3 wt %, 3.5 wt %, 4 wt %, 4.5 wt % or 5 wt %)) (Sunscreen), or a combination thereof.

In certain embodiments, the composition comprises Beeswax, Camphor, Cetyl Alcohol, Cetyl Palmitate, *Euphorbia cerifera* (Candelilla) Wax, Flavor, Isopropyl Myristate, Lanolin, Lanolin Oil, Menthol, Methyl Salicylate, Mineral Oil, Ozokerite, Paraffin, Petrolatum, Polybutene, Red 6 Lake, *Theobroma cacao* (Cocoa) Seed Butter, Titanium Dioxide, Phenoxyethanol, or a combination thereof.

In certain embodiments, the composition comprises Mineral Oil, Paraffin, Ozokerite, Dimethicone, Ceramide NP, Ceramide AP, Ceramide EOP, Carbomer, Water, Sodium Lauroyl Lactylate, Proline, Cholesterol, Phenoxyethanol, Tocopheryl Acetate, Tocopherol Hydrolized Hyaluronic Acie, Panthenol, Pantolactone, Phytosphingosine, Xanthan Gum, Ethylhexylglycerin, or a combination thereof.

In certain embodiments, the composition comprises Mineral Oil, Paraffin, Ozokerite, Dimethicone, Hyaluronic Acid, Sodium Hydroxide, Ceramide 1, Ceramide 3, Ceramide 6-II, Tocopheryl Acetate, Phytosphingosine, Cholesterol, Sodium Lauroyl Lactylate, Carbomer, Panthenol, Water, L-proline, Xanthan Gum, or a combination thereof.

In certain embodiments, the composition comprises Purified Water, Glycerin, Ceteareth-20 and Cetearyl Alcohol, Caprylic/Capric Triglyceride, Behentrimonium Methosulfate and Cetearyl Alcohol, Cetyl Alcohol, Ceramide 3, Ceramide 6-11, Ceramide 1, Hyaluronic Acid, Cholesterol, Petrolatum, Dimethicone, Potassium Phosphate, Dipotassium Phosphate, Sodium Lauroyl Lactylate, Disodium EDTA, Phenoxyethanol, Methylparaben, Propylparaben, Phytosphingosine, Carbomer, Xanthan Gum, or a combination thereof.

In certain embodiments, the composition comprises Aqua/Water/Eau, Glycerin, Petrolatum, Caprylic/Capric Triglyceride, Hydrogenated Vegetable Oil, Sucrose Distearate, Dextrin, *Helianthus annuus* (Sunflower) Seed Oil Unsaponifiables, *Prunus domestica* Seed Extract, or a combination thereof.

In certain embodiments, the composition comprises Mineral Oil, Paraffin *Avena sativa*, (Oat) Kernel Flour, *Theobroma cacao* (Cocoa), Seed Butter, Tocopheryl Acetate, or a combination thereof.

In certain embodiments, the composition comprises Water (Aqua), Glycerin, Dimethicone, Stearic Acid, Caprylic/Capric Triglyceride, Glycol Stearate, PEG-100 Stearate, Petrolatum, Glyceryl Stearate, Caprylyl Glycol, Phenoxyethanol, Cetyl Alcohol, Acrylates/C10-30 Alkyl Acrylate Crosspolymer, Triethanolamine, *Helianthus annuus* (Sunflower) Seed Oil, Triolein, Disodium EDTA, Stearamide AMP, Carbomer, Titanium Dioxide (CI 77891), or a combination thereof. In certain embodiments, the composition comprises *vulgare* (Wheat Germ) Oil, Tochopherol Pentaerythrityl Tetra-DI-T-Butyl Hydroxyhydrocinnamate, Allantoin, Isopropyl Palmitate, Paraffinum Liquidum (Mineral Oil), Isopropyl Myristate, Aloe Barbadensis (Aloe Vera) Leaf Extract, BHE, or a combination thereof.

In certain embodiments, the composition comprises Petrolatum (10-50%, 25-60%, 50-80%), Zinc Oxide (5-15%, 10-25%, 15-20%, 20-30%), Titanium Oxide (5-15%, 10-25%, 15-20%, 20-30%), Octocrylene (5-10%, 10-15%, 15-20%), Octinoxate (5-10%, 10-15%, 15-20%), or a combination thereof.

In certain embodiments, the composition comprises Beeswax, *Betula alba* (White Birch) Bark Extract, Butyrospermum Parkii (Shea Butter), *Calendula* Oil, Corn Starch, *Glycine soja* (Soybean) Oil, Lanolin, Pantothenyl Ethyl Ether, Paraffin, Propylparaben, Tocopheryl Acetate, or a combination thereof.

In certain embodiments, the composition comprises Petrolatum, Cod Liver Oil, Lanolin, Glycerin, Beeswax, Sorbitan Sesquioleate, Fragrance, Pentaerythrityl Tetra-di-t-butyl Hydroxyhydrocinnamate, Tocopheryl Acetate, Talc, or a combination thereof.

In certain embodiments, the composition comprises White Petrolatum, Corn Starch, Anhydrous Lanolin, Stearyl Alcohol, Beeswax, Bisabolol, Cholesterol, Water, Glycerine, Oat (*Avena sativa*) Kernel Extract, Polysorbate 80, or a combination thereof.

In certain embodiments, the composition comprises Alpha-tocopherol Acetate, Butylated Hydroxytoluene, Lanolin, Lavender Oil, Light Mineral Oil, Methylparaben, Petrolatum, Polysorbate 60, or a combination thereof.

In certain embodiments, the composition comprises Mineral Oil, White Petrolatum, White Wax, or a combination thereof.

In certain embodiments, the composition comprises α-tocopherol Acetate, Aloe Vera Leaf, Light Mineral Oil, Paraffin, Petrolatum or a combination thereof.

In certain embodiments, the composition comprises Light Mineral Oil, White Beeswax, White Petrolatum, or a combination thereof.

In certain embodiments, the composition comprises Carnauba Wax, Isopropyl Palmitate (and) Isopropyl Myristate (and) Aloe Barbadensis Leaf Extract, Lanolin, Fragrance, Petrolatum, Sorbitan Sesquioleate, Tocopheryl Acetate (Vitamin E), or a combination thereof.

In certain embodiments, the composition comprises Bismuth Oxychloride, C12-15 Alkyl Benzoate, Caprylhydroxamic Acid, Caprylyl Glycol, Cetyl PEG/PPG 10/1 Dimethicone, Cyclohexasiloxane, Cyclopentasiloxane, Dimethicone, Dimethicone Crosspolymer, Dimethicone/Vinyl Dimethicone Crosspolymer, Dimethiconol, Disodium EDTA, Glycerin, Hydrogen Dimethicone, Iron Oxides, Mica, Microcrystalline Wax, PEG-10 Dimethicone, PEG-30 Dipolyhydroxystearate, Polyglyceryl-4 Isostearate, Polyhydroxystearic Acid, Polysorbate 20, Sodium Chloride, Stearyl Dimethicone, Tetrahexyldecyl Ascorbate, Tocopheryl Acetate, Triethanolamine, Triethoxycaprylylsilane, Water, or a combination thereof.

In certain embodiments, the composition comprises Water, C12-15 Alkyl Benzoate, Styrene/Acrylates Copolymer, Octyldodecyl Citrate Crosspolymer, Phenyl Trimethicone, Cetyl PEG/PPG-10/1 Dimethicone, Dimethicone, Polyhydroxystearic Acid, Glycerin, Ethyl Methicone, Cetyl Dimethicone, Silica, *Chrysanthemum parthenium* (Feverfew) Flower/Leaf/Stem Juice, Glyceryl Behenate, Phenethyl Alcohol, Caprylyl Glycol, Cetyl Dimethicone/Bis-Vinyldimethicone Crosspolymer, Acrylates/Dimethicone Copolymer, Sodium Chloride, Phenoxyethanol, Chlorphenesin, or a combination thereof.

In certain embodiments, the composition comprises Octyldodecyl Neopentanoate, C12-15 Alkyl Benzoate, Polyethylene, Paraffin, Silica, Neopentyl Glycol Diethylhexanoate, Ozokerite, Isopropyl Myristate, Adipic Acid/Diglycol Crosspolymer, Triethoxycaprylylsilane, Neopentyl Glycol Diisostearate, Caprylyl Glycol, Tocopheryl Acetate, or a combination thereof.

In certain embodiments, the composition comprises Water, *Cocos nucifera* (Coconut) Oil, Butyloctyl Salicylate, Diheptyl Succinate, Methyl Dihydroabietate, Butyrospermum Parkii (Shea Butter), Fragrance, Capryloyl Glycerin/Sebacic Acid Copolymer, Sodium Stearoyl Glutamate, Cetearyl Alcohol, *Theobroma cacao* (Cocoa) Seed Butter, Coco-Glucoside, Tocopherol, Microcrystalline Cellulose, Cellulose Gum, Bisabolol, Cetyl Alcohol, Arachidyl Alcohol, Behenyl Alcohol, Arachidyl Glucoside, Polyhydroxystearic Acid, Sodium Hyaluronate, Sodium Gluconate, Phenoxyethanol, Ethylhexylglycerin, Citric Acid, or a combination thereof.

In certain embodiments, the composition comprises Water, Diisopropyl Adipate, Ethylhexyl Palmitate, Ethylhexyl Stearate, Cetyl PEG/PPG-10/1 Dimethicone, Glycerin, Cetyl Dimethicone, Hydrogenated Castor Oil, Hydrated Silica, Cyclopentasiloxane, Polyethylene, Aloe Barbadensis Leaf Extract, Tocopheryl Acetate, *Theobroma cacao* (Cocoa) Seed Butter, Beeswax, Cyclohexasiloxane, Triethoxycaprylylsilane, Sodium Chloride, DMDM Hydantoin, Fragrance, or a combination thereof.

In certain embodiments, the composition comprises Water, Dimethicone, Isododecane, C12-15 Alkyl Benzoate, Undecane, Triethylhexanoin, Isohexadecane, Nylon-12, Caprylyl Methicone, Butyloctyl Salicylate, Phenethyl Benzoate, Styrene/Acrylates Copolymer, Silica, Tridecane, Dicaprylyl Carbonate, Dicaprylyl Ether, Talc, Dimethicone/Peg-10/15 Crosspolymer, Aluminum Stearate, Pentylene Glycol, Peg-9 Polydimethylsiloxyethyl Dimethicone, Alumina, Polyhydroxystearic Acid, Phenoxyethanol, Magnesium Sulfate, Caprylyl Glycol, Iron Oxides, Peg-8 Laurate, Disteardimonium Hectorite, Triethoxycaprylylsilane, Tocopherol, Propylene Carbonate, Artemia Extract, Benzoic Acid, C9-15 Fluoroalcohol Phosphate, Peg-9, or a combination thereof.

In certain embodiments, the composition comprises allantoin, butyloctyl salicylate, C12-15 alkyl benzoate, caprylyl glycol, dimethiconol/propylsilsesquioxane/silicate crosspolymer, glyceryl behenate, glyceryl dibehenate, glyceryl stearate, isodecyl salicylate, isopropyl isostearate, lecithin, neopentyl glycol diheptanoate, 1,2-hexanediol, polyester-7, polyglyceryl-3 polyricinoleate, propanediol, silica silylate, sodium chloride, squalane, tribehenin, tridecyl salicylate, water, or a combination thereof.

In certain embodiments, the composition comprises *Helianthus annus* Sunflower Seed Oil *Cocos nucifera* Coconut Oil Cera Alba Beeswax *Ricinus communis* Castor Seed Oil *Rubus idaeus* Red Raspberry Seed Oil Butyrospermum Parkii Shea Butter *Prunus armeniaca* Apricot Kernel Oil Argania *spinosa* Argan Kernel Oil *Rosa canina* Rosehip Fruit Oil Tocopherol, or a combination thereof.

In certain embodiments, the composition comprises Water, Cyclopentasiloxane, Zinc Oxide, Propanediol, Titanium Dioxide, Butylene Glycol Dicaprylate/Dicaprate, Lauryl Polyglyceryl-3 Polydimethylsiloxyethyl Dimethicone, Methyl Methacrylate Crosspolymer, Butyloctyl Salicylate, Caprylyl Methicone, *Citrus aurantium dulcis* (Orange) Oil, *Citrus nobilis* (Mandarin Orange) Peel Oil, *Litsea Cubeba* Fruit Oil, 1,2-Hexanediol, Disteardimonium Hectorite, Magnesium Sulfate, Stearic Acid, Aluminum Hydroxide, Polyglyceryl-3 Polydimethylsiloxyethyl Dimethicone, Triethoxycaprylylsilane, Sorbitan Caprylate, Glyceryl Caprylate, Ethylhexylglycerin, Tocopherol, or a combination thereof.

In certain embodiments, the composition comprises Water, Dimethicone, Isododecane, C12-15 Alkyl Benzoate, Undecane, Triethylhexanoin, Isohexadecane, Nylon-12, Caprylyl Methicone, Butyloctyl Salicylate, Phenethyl Benzoate, Styrene/Acrylates Copolymer, Silica, Tridecane, Dicaprylyl Carbonate, Dicaprylyl Ether, Talc, Dimethicone/PEG-10/15 Crosspolymer, Aluminum Stearate, Pentylene Glycol, PEG-9 Polydimethylsiloxyethyl Dimethicone, Alumina, Polyhydroxystearic Acid, Phenoxyethanol, Magnesium Sulfate, Propylene Glycol, Caprylyl Clycol, PEG-8 Laurate, Disteardimonium Hectorite, Triethoxycaprylylsilane, Diethylhexyl Syringylidenemalonate, Tocopherol, Propylene Carbonate, *Cassia alata* Leaf Extrace, Maltodextrin, Benzoic Acid, PEG-9, or a combination thereof.

In certain embodiments, the composition comprises Water, C12-15 Alkyl Benzoate, Isopropyl Palmitate, Butyloctyl Salicylate, Ethylhexyl Pelargonate, Cetyl PEG/PPG-10/1 Dimethicone, Propylene Glycol, Cyclopentasiloxane, Bis-Octyldodecyl Dimer Dilinoleate/Propanediol Copolymer, Dimethicone, Ethylhexyl Methoxycrylene, Polyester-27, Triethoxycaprylylsilane, Beeswax, Hydroxyacetophenone, Sodium Chloride, PEG-12 Dimethicone Crosspolymer, 1,2-Hexanediol, Caprylyl Glycol, Tocopherol, or a combination thereof.

In certain embodiments, the composition comprises Octyldodecyl Neopentanoate, C12-15 Alkyl Benzoate, Polyethylene, Paraffin, Silica, Neopentyl Glycol Diethylhexanoate, Ozokerite, Isopropyl Myristate, Adipic Acid/Diglycol Crosspolymer, Triethoxycaprylylsilane, Neopentyl Glycol Diisostearate, Caprylyl Glycol, *Avena sativa* (Oat) Kernel Oil, or a combination thereof.

In certain embodiments, the composition comprises Octyldodecyl Neopentanoate, C12-15 Alkyl Benzoate, Polyethylene, Paraffin, Silica, Neopentyl Glycol Diethylhexanoate, Ozokerite, Isopropyl Myristate, Adipic Acid/Diglycol Crosspolymer, Triethoxycaprylylsilane, Neopentyl Glycol Diisostearate, Caprylyl Glycol, *Avena sativa* (Oat) Kernel Oil, Tocopheryl Acetate, or a combination thereof.

In certain embodiments, the composition comprises C12-15 Alkyl Benzoate, Octyldodecyl Neopentanoate, Dimethicone, Paraffin, Ozokerite, Beeswax, Phenyl Trimethicone, *Euphorbia cerifera* (Candelilla) Wax, Polyethylene, Polyhydroxystearic Acid, Dipropylene Glycol Dibenzoate, Triethoxycaprylylsilane, PPG-15 Stearyl Ether Benzoate, Caprylyl Glycol, Ethylhexyglycerin, *Avena sativa* (Oat) Kernel Flour, BHT, or a combination thereof.

In certain embodiments, the composition comprises Water, Isobutane, Isododecane, Cetyl PEG/PPG-10/1 Dimethicone, Caprylic/Capric Triglyceride, Butyloctyl Salicylate, phenoxyethanol, polyhydrostearic acid, Triethoxycaprylylsilane, Sodium Citrate, or a combination thereof.

In certain embodiments, the composition comprises Water, Caprylic/Capric Triglyceride, Isohexadecane, Butyloctyl Salicylate, Octyldodecyl Citrate Crosspolymer, Cetyl PEG/PPG-10/1 Dimethicone, Lauryl PEG-8 Dimethicone, C30-38 Olefin/Isopropyl Maleate/MA Copolymer, Sodium Chloride, Ethylhexyl Methoxycrylene, Dimethicone, Phenoxyethanol, Caprylyl Glycol, PEG-8, Alumina, Glycerin, Sodium Citrate, Tocopheryl Acetate, or a combination thereof.

In certain embodiments, the composition comprises Arachidyl Alcohol, Arachidyl Glucoside, Behenyl Alcohol, Bisabolol, Butyloctyl Salicylate, Butyrospermum Parkii (Shea) Butter, *Calendula officinalis* Flower Extract, *Camellia sinensis* Leaf Extract, Caprylhydroxamic Acid, Caproyl Glycerin/Sebacic Acid Copolymer, Caprylyl Glycol, Cellulose Gum, Cetearyl Alcohol, Cetyl Alcohol, *Chamomilla recutita (matricaria)* Flower Extract, Citric Acid, *Citrus aurantium dulcis* (Orange) Peel Oil, Coco-Glucoside, *Cocos nucifera* (Coconut) Oil, *Cucumis sativus* (Cucumber) Fruit Extract, Diheptyl Succinate, Glycerin, Methyl Dihydroabietate, Microcrystalline Cellulose, Polyhydroxystearic Acid, *Persea gratissima* (Avocado) Fruit Extract, *Prunus armeniaca* (Apricot) Kernel Oil, Sodium Gluconate, Sodium Hyaluronate, Sodium Stearoyl Glutamate, *Theobroma cacao* (Cocoa) Seed Butter, Tocopherol, Triethyl Citrate, *Vanilla planifolia* Fruit Extract, Water Certified Organic, or a combination thereof.

In certain embodiments, the composition comprises Arachidyl Alcohol, Arachidyl Glucoside, Behenyl Alcohol, Bisabolol, Butyloctyl Salicylate, Butyrospermum Parkii (Shea) Butter, *Calendula officinalis* Flower Extract, *Camellia SINENSIS* Leaf Extract, Caprylhydroxamic Acid, Caproyl Glycerin/Sebacic Acid Copolymer, Caprylyl Glycol, Cellulose Gum, Cetearyl Alcohol, Cetyl Alcohol, *Chamomilla recutita (matricaria)* Flower Extract, Citric Acid, *Citrus aurantium dulcis* (Orange) Peel Oil, Coco Glucoside, *Cocos nucifera* (Coconut) Oil, *Cucumis sativus* (Cucumber) Fruit Extract, Diheptyl Succinate, Glycerin, Methyl Dihydroabietate, Microcrystalline Cellulose, Polyhydroxystearic Acid, *Persea gratissima* (Avocado) Fruit Extract, *Prunus armeniaca* (Apricot) Kernel Oil, Sodium Gluconate, Sodium Hyaluronate, Sodium Stearoyl Glutamate, *Theobroma cacao* (Cocoa) Seed Butter, Tocopherol, Triethyl Citrate, *Vanilla planifolia* Fruit Extract, Water, or a combination thereof.

In certain embodiments, the composition comprises Purified Water, Caprylic/capric Triglyceride, Polyglyceryl-4 Isostearate, Glycerin, Hydrogenated Glyceryl Abietate, Hexyl Laurate, Cetyl Dimethicone, Aloe Barbadensis Leaf Juice, Hydrogenated Castor Oil, Magnesium Sulfate, *Helianthus annuus* (Sunflower) Seed Oil, *Simmondsia chinensis* (Jojoba) Seed Oil, Tocopherol, *Olea europaea* (Olive) Fruit Oil, *Rubus idaeus* (Raspberry) Seed Oil, *Vaccinium macrocarpon* (Cranberry) Seed Oil, Sodium Hyaluronate, *Carica papaya (papaya)* Fruit Extract, *Ribes nigrum* (Black Currant) Extract, Citrus Paridisi (Pink Grapefruit) Peel Oil, Sorbitan Sesquioleate, Caprylhydroxamic Acid, Triethoxycaprylylsilane, Glyceryl Caprylate, or a combination thereof.

In certain embodiments, the composition comprises purified water, aloe barbadensis leaf juice, capric caprylic triglycerides, sorbitan stearate (coconut based), pine wood resin, vegetable glycerin, cetyl dimethicone, hydrogenated castor oil, magnesium sulfate (epsom salt), sunflower oil, jojoba oil, ascorbic acid (vitamin c), tocopherols (vitamin e), olive oil, raspberry seed oil, cranberry seed oil, hyaluronic acid (made from vegetable), glucose & glucose oxidase and lactoperoxidase, papaya, or a combination thereof.

In certain embodiments, the composition comprises Alumina Aluminum Stearate Beeswax C12-15 Alkyl Benzoate Caprylyl Glycol Cetyl Dimethicone Cetyl PEG/PPG-10/1 Dimethicone Chlorphenesin Dimethicone Disodium EDTA Ethylhexyl Palmitate Ethylhexyl Stearate Hexyl Laurate Hydrogenated Castor Oil Methyl Glucose Dioleate Octyldodecyl Neopentanoate PEG-7 Hydrogenated Castor Oil Phenoxyethanol Polyglyceryl-4 Isostearate Polyhydroxystearic Acid Propanediol Purified Water Sorbitan Oleate Stearic Acid Tocopheryl Acetate Trimethylsiloxy silicate VP/Hexadecene Copolymer, or a combination thereof.

In certain embodiments, the composition comprises Dimethicone, Caprylic/Capric Triglyceride, Dimethicone Crosspolymer, Dimethicone/Vinyl Dimethicone Crosspolymer, Butyloctyl Salicylate, Glyceryl Isostearate, Polyester-8, Polysilicone-15, Behenic Acid, *Camelia sinensis* Leaf Extract, Caprooyl Phytosphingosine, Ceramide AP, Ceramide EOP, Ceramide EOS, Ceramide NP, Ceramide NS, Ceteareth-25, Cetyl Alcohol, Cholesterol, Glycerin, Iron Oxides, PEG/PPG-18/18 Dimethicone, *Punica granatum* Extract, Silica, Tetrahexyldecyl Ascorbate, Tocopheryl Acetate, Triethoxycaprylysilane, *vaccinum macrocarpon* (Cranberry) Fruit Extract, or a combination thereof.

In certain embodiments, the composition comprises Water, Glycerin, C12-15 Alkyl Benzoate, Dimethicone, Isododecane, Styrene/Acrylates Copolymer, Glyceryl Stearate, Butyloctyl Salicylate, Dicaprylyl Carbonate, Propanediol, Stearic Acid, Aluminum Hydroxide, Peg-100 Stearate, Sorbitan Stearate, Niacinamide, Peg-8 Laurate, Ceramide Np, Ceramide Ap, Ceramide Eop, Sorbitan Isostearate, Carbomer, Cetearyl Alcohol, Ceteareth-20, Triethoxycaprylylsilane, Dimethiconol, Sodium Citrate, Sodium Lauroyl Lactylate, Sodium Dodecylbenzenesulfonate, Myristic Acid, Sodium Hyaluronate, Cholesterol, Palmitic Acid, Phenoxyethanol, Chlorphenesin, Tocopherol, Hydroxyethyl Acrylate/Sodium Acryloyldimethyl Taurate Copolymer, Caprylyl Glycol, Citric Acid, Panthenol, Xanthan Gum, Phytosphingosine, Polyhydroxystearic Acid, Polysorbate 60, Ethylhexylglycerin, or a combination thereof.

In certain embodiments, the composition comprises Alumina, Cyclohexasiloxane, Cyclopentasiloxane, Dimethicone, Dimethicone Crosspolymer, Dimethicone/Vinyl Dimethicone Crossspolymer, Dimethiconol, Lauryl PEG/PPG-18/18 Methicone, Methicone, PEG-10 Dimethicone, or a combination thereof.

In certain embodiments, the composition comprises Aqua, *Cocos nucifera* (Coconut oil), *Persea gratissima* (Avocado oil), Cetearyl Alcohol/Polysorbate 60 (Vegetable emulsifying wax NF), *Butyrospernum Parkii* (Shea butter), *Rubus idaeus* (Red Raspberry seed oil), Glyceryl Oleate Citrate & Caprylic/Capric Triglyceride, Glycerin, Cera alba (Beeswax), Ethylhexylglycerin & Propanediol, Polyhydroxystearic Acid, Sodium Gluconate, *Cocos nucifera* (Coconut essential oil), Vanilla Plantifolia (Vanilla essential oil), or a combination thereof.

In certain embodiments, the composition comprises Organic Sunflower Oil, Organic Beeswax, Sunflower Vitamin E, or a combination thereof.

In certain embodiments, the composition comprises *Helianthus annuus* (Sunflower) Seed Oil, Cera Alba (Beeswax), Tocopherol (Sunflower Vitamin E), or a combination thereof.

In certain embodiments, the composition comprises Petrolatum, Coconut Alkanes, Coco-Caprylate/Caprate, and an analgesic. In certain embodiments, the composition comprises Petrolatum, Coconut Alkanes, Coco-Caprylate/Caprate, and Lidocaine. In some embodiments, the composition is in the form of a radiation spray.

In certain embodiments, the composition comprises Petrolatum, Coconut Alkanes, Coco-Caprylate/Caprate, Camphor (Cough Suppressant and Topical Analgesic), Menthol (Cough Suppressant and Topical Analgesic), and *Eucalyptus globulus* Leaf Oil.

In certain embodiments, the composition comprises Petrolatum, Coconut Alkanes, Coco-Caprylate/Caprate, Camphor (Cough Suppressant and Topical Analgesic), Menthol (Cough Suppressant and Topical Analgesic), *Eucalyptus globulus* Leaf Oil, *Myristica fragrans* (Nutmeg) Kernel Oil, Turpentine Oil, C18-C36 Acid Triglyceride, Jojoba Esters, C12-C18 Acid Triglyceride, Squalene, Thymol, Phytosteryl Macadamiate, Phytosterols, and Tocopherol. In some embodiments, the composition is in the form of a vapor spray.

In certain embodiments, the composition comprises polyol or a diol. Exemplary diols may include, without limitations, one or more of propylene glycol, propanediol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol, dibutylene glycol, isopentyldiol, ethoxydiglycol, or a combination thereof. The diol included in the delivery systems described herein is present at a concentration of about 1-25 wt %, about 0.1-10 wt %, about 0.1-5 wt %, about 0.1-1 wt %, about 1-5 wt %, about 1-10 wt %, about 5-10 wt %, about 1-15 wt %, about 10-15 wt %, about 15-20 wt %, about 20-25 wt %, about 25-30 wt %, about 30-35 wt %, about 35-40 wt %, about 40-45 wt %, about 45-50 wt %, about 50-55 wt %, about 55-60 wt %, about 60-65 wt %, about 65-70 wt %, about 70-75 wt %, about 75-80 wt %, about 80-85 wt %, about 85-90 wt %, or about 90-95 wt %, based on the total weight of the composition. For example, the diol can be present at a concentration of about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt % or about 25 wt %, based on the total weight of the composition.

In certain embodiments, the composition comprises bakuchiol at an amount of about 0.01-10 wt %, about 0.01-1 wt %, about 0.01-1 wt %, about 0.1-0.3 wt %, about 0.3-0.5 wt %, about 0.5-0.7 wt %, about 0.7-1 wt %, or about 1-3 wt %, about 3-5 wt %, about 5-7 wt %, about 7-10 wt %, about 10-15 wt %, about 15-20 wt %, or about 20-25 wt %, based on total weight of the composition.

In certain embodiments, the composition comprises water (Aqua) at an amount of about 0.001-25 wt % based on the weight of the formulation. For example, the composition can comprise water at concentration ranges of about 0.1-25 wt % based on the weight of the formulation. For example, the composition can comprise about 0.1-20%, about 0.1-15 wt %, about 0.1-10 wt %, about 0.1-5 wt %, about 0.1-1 wt %, about 0.1-0.5 wt %, about 0.1-0.3 wt %, about 0.3-0.5 wt %, about 0.5-0.7 wt %, about 0.7-1 wt %, or about 1-3 wt %, about 3-5 wt %, about 5-7 wt %, about 7-10 wt %, about 10-15 wt %, about 15-20 wt %, or about 20-25 wt % of water (Aqua) based on total weight of the formulation.

In certain embodiments, the composition comprises Caprylic/Capric Triglyceride at an amount of about 0.001-25 wt % based on the weight of the formulation. For example, the composition can comprise at concentration ranges of about 0.1-25 wt % based on the weight of the formulation. For example, the composition can comprise about 0.1-20%, about 0.1-15 wt %, about 0.1-10 wt %, about 0.1-5 wt %, about 0.1-1 wt %, about 0.1-0.5 wt %, about 0.1-0.3 wt %, about 0.3-0.5 wt %, about 0.5-0.7 wt %, about 0.7-1 wt %, or about 1-3 wt %, about 3-5 wt %, about 5-7 wt %, about 7-10 wt %, about 10-15 wt %, about 15-20 wt %, or about 20-25 wt % of Caprylic/Capric Triglyceride based on total weight of the formulation.

In certain embodiments, the composition comprises glycerin at an amount of about 0.001-25 wt % based on the weight of the formulation. For example, the composition can comprise at concentration ranges of about 0.1-25 wt % based on the weight of the formulation. For example, the composition can comprise about 0.1-20%, about 0.1-15 wt %, about 0.1-10 wt %, about 0.1-5 wt %, about 0.1-1 wt %, about 0.1-0.5 wt %, about 0.1-0.3 wt %, about 0.3-0.5 wt %, about 0.5-0.7 wt %, about 0.7-1 wt %, or about 1-3 wt %, about 3-5 wt %, about 5-7 wt %, about 7-10 wt %, about 10-15 wt %, about 15-20 wt %, or about 20-25 wt % of glycerin based on total weight of the formulation.

In certain embodiments, the composition comprises Methyl Dihydroabietate at an amount of about 0.01-10 wt % based on the weight of the formulation. For example, the composition can comprise about 0.01-1 wt %, about 0.01-0.5 wt %, about 0.01-0.1 wt %, about 0.01-0.05 wt %, about 0.1-10 wt %, about 0.1-5 wt %, about 0.1-5 wt %, about 0.1-1 wt %, about 0.1-0.5 wt %, about 0.1-0.3 wt %, about 0.3-0.5 wt %, about 0.5-0.7 wt %, about 0.7-1 wt %, or about 1-3 wt %, about 3-5 wt %, about 5-7 wt %, or about 7-10 wt % of Methyl Dihydroabietate based on total weight of the formulation.

In certain embodiments, the composition comprises cetearyl alcohol at an amount of about 0.01-10 wt % based on the weight of the formulation. For example, the composition can comprise about 0.01-1 wt %, about 0.01-0.5 wt %, about 0.01-0.1 wt %, about 0.01-0.05 wt %, about 0.1-10 wt %, about 0.1-5 wt %, about 0.1-5 wt %, about 0.1-1 wt %, about 0.1-0.5 wt %, about 0.1-0.3 wt %, about 0.3-0.5 wt %, about 0.5-0.7 wt %, about 0.7-1 wt %, or about 1-3 wt %, about 3-5 wt %, about 5-7 wt %, or about 7-10 wt % of cetearyl alcohol based on total weight of the formulation.

In certain embodiments, the composition comprises Bisabolol at an amount of about 0.01-10 wt % based on the weight of the formulation. For example, the composition can comprise about 0.01-1 wt %, about 0.01-0.5 wt %, about 0.01-0.1 wt %, about 0.01-0.05 wt %, about 0.1-10 wt %, about 0.1-5 wt %, about 0.1-5 wt %, about 0.1-1 wt %, about 0.1-0.5 wt %, about 0.1-0.3 wt %, about 0.3-0.5 wt %, about 0.5-0.7 wt %, about 0.7-1 wt %, or about 1-3 wt %, about 3-5 wt %, about 5-7 wt %, or about 7-10 wt % of Bisabolol based on total weight of the formulation.

In certain embodiments, the composition comprises lactic acid at an amount of about 0.001-10 wt % based on the weight of the formulation. For example, the composition can comprise about 0.001-1 wt %, about 0.001-0.5 wt %, about 0.001-0.1 wt %, about 0.001-0.05 wt %, about 0.001-0.01 wt %, about 0.001-0.005 wt %, about 0.001-0.003 wt %, about 0.001-0.002 wt %, 0.1-10%, about 0.1-5%, about 0.1-5%, about 0.1-1%, about 0.1-0.5%, about 0.1-0.3 wt %, about 0.3-0.5 wt %, about 0.5-0.7 wt %, about 0.7-1 wt %, or about 1-3 wt %, about 3-5 wt %, about 5-7 wt %, or about 7-10 wt % of lactic acid based on total weight of the formulation.

In certain embodiments, the composition comprises citric acid at an amount of about 0.001-10 wt % based on the weight of the formulation. For example, the composition can comprise about 0.001-1 wt %, about 0.001-0.5 wt %, about 0.001-0.1 wt %, about 0.001-0.05 wt %, about 0.001-0.01 wt %, about 0.001-0.005 wt %, about 0.001-0.003 wt %, about 0.001-0.002 wt %, 0.1-10%, about 0.1-5%, about 0.1-5%, about 0.1-1%, about 0.1-0.5%, about 0.1-0.3 wt %, about 0.3-0.5 wt %, about 0.5-0.7 wt %, about 0.7-1 wt %, or about 1-3 wt %, about 3-5 wt %, about 5-7 wt %, or about 7-10 wt % of citric acid based on total weight of the formulation.

In certain embodiments, the composition comprises coco-glucoside at an amount of about 0.001-1 wt % based on the weight of the formulation. For example, the composition can comprise about 0.001-0.01 wt %, about 0.001-0.5 wt %, about 0.001-0.4 wt %, about 0.001-0.3 wt %, about 0.001-0.25 wt %, about 0.001-0.2 wt %, about 0.001-0.15 wt %, about 0.001-0.1 wt %, about 0.001-0.05 wt %, about 0.001-0.04 wt %, about 0.001-0.03 wt %, about 0.001-0.01 wt %, about 0.001-0.025 wt %, about 0.001-0.02 wt %, about 0.001-0.015 wt %, about 0.005-0.01 wt %, about 0.01-0.05 wt %, about 0.05-0.1 wt %, about 0.1-0.15 wt %, about 0.15-0.2 wt %, about 0.2-0.25 wt %, about 0.25-0.3 wt %, about 0.3-0.35 wt %, about 0.35-0.4 wt % or about 0.4-0.45 wt %, about 0.45-0.5 wt %, about 0.5-0.55 wt %, about 0.55-0.6 wt %, about 0.6-0.65 wt %, about 0.65-0.7 wt %, about 0.7-0.75 wt %, about 0.75-0.8 wt %, about 0.8-0.85 wt %, about 0.85-0.9 wt %, about 0.9-0.95 wt %, or about 0.95-1 wt % of coco-glucoside based on the weight of the formulation.

In some embodiments, the composition comprises a glucan. In some embodiments, the composition comprises a beta-glucan. In some embodiments, the composition comprises Sodium Carboxymethyl Beta-Glucan at a concentration range of about 0.01-10 wt % based on the weight of the formulation. For example, the composition can comprise about 0.1-10 wt %, about 0.1-5 wt %, about 0.1-5 wt %, about 0.1-1 wt %, about 0.1-0.5 wt %, about 0.1-0.3 wt %, about 0.3-0.5 wt %, about 0.5-0.7 wt %, about 0.7-1 wt %, or about 1-3 wt %, about 3-5 wt %, about 5-7 wt %, or about 7-10 wt % of beta-glucan based on total weight of the formulation.

In certain embodiments, the composition comprises isohexadecane at an amount of about 0.01-10 wt % based on the weight of the formulation. For example, the composition can comprise about 0.01-1 wt %, about 0.01-0.5 wt %, about 0.01-0.1 wt %, about 0.01-0.05 wt %, about 0.1-10%, about 0.1-5%, about 0.1-5%, about 0.1-1%, about 0.1-0.5%, about 0.1-0.3 wt %, about 0.3-0.5 wt %, about 0.5-0.7 wt %, about 0.7-1 wt %, or about 1-3 wt %, about 3-5 wt %, about 5-7 wt %, or about 7-10 wt % of isohexadecane based on total weight of the formulation. In certain embodiments, the composition comprises 30-60 wt % of isohexadecane. In certain embodiments, the composition comprises 45 wt % of isohexadecane.

In certain embodiments, the composition comprises silica at an amount of about 0.01-10 wt % based on the weight of the formulation. For example, the composition can comprise about 0.01-1 wt %, about 0.01-0.5 wt %, about 0.01-0.1 wt %, about 0.01-0.05 wt %, about 0.1-10 wt %, about 0.1-5 wt %, about 0.1-5 wt %, about 0.1-1 wt %, about 0.1-0.5 wt %, about 0.1-0.3 wt %, about 0.3-0.5 wt %, about 0.5-0.7 wt %, about 0.7-1 wt %, or about 1-3 wt %, about 3-5 wt %, about 5-7 wt %, or about 7-10 wt % of silica based on total weight of the formulation.

In some embodiments, the compositions comprise any one or more of Caprylhydroxamic Acid, Polyhydroxystearic Acid, Bentonite, Ethylhexylglycerin, Heptyl Undecylenate, Hexylene Glycol, Cetyl Glyceryl Ether, Caprylyl Glycol, or Phenoxyethanol. In certain embodiments, the composition comprises any one or more of Caprylhydroxamic Acid, Polyhydroxystearic Acid, Bentonite, Ethylhexylglycerin, Heptyl Undecylenate, Hexylene Glycol, Cetyl Glyceryl Ether, Caprylyl Glycol or Phenoxyethanol, individually or collectively at an amount of about 0.001-1 wt % based on the weight of the formulation. For example, the composition can comprise about 0.001-0.01 wt %, about 0.001-0.5 wt %, about 0.001-0.4 wt %, about 0.001-0.3 wt %, about 0.001-0.25 wt %, about 0.001-0.2 wt %, about 0.001-0.15 wt %, about 0.001-0.1 wt %, about 0.001-0.05 wt %, about 0.001-0.04 wt %, about 0.001-0.03 wt %, about 0.001-0.01 wt %, about 0.001-0.025 wt %, about 0.001-0.02 wt %, about 0.001-0.015 wt %, about 0.005-0.01 wt %, about 0.01-0.05 wt %, about 0.05-0.1 wt %, about 0.1-0.15 wt %, about 0.15-0.2 wt %, about 0.2-0.25 wt %, about 0.25-0.3 wt %, about 0.3-0.35 wt %, about 0.35-0.4 wt % or about 0.4-0.45 wt %, about 0.45-0.5 wt %, about 0.5-0.55 wt %, about 0.55-0.6 wt %, about 0.6-0.65 wt %, about 0.65-0.7 wt %, about 0.7-0.75 wt %, about 0.75-0.8 wt %, about 0.8-0.85 wt %, about 0.85-0.9 wt %, about 0.9-0.95 wt %, or about 0.95-1 wt % based on the weight of the formulation.

In certain embodiments, the compositions are packaged into a spray delivery system that provides a mist or spray such as a can-in-can aerosol system. Optionally, the spray barrier formulation can be packaged into a bag-on-valve aerosol system. In certain embodiments, the product is delivered by a system that separates the formulation from the propellant. Those skilled in the art will realize that there are several known methods of mixing ingredients to obtain a sprayable composition and the procedure described should not be considered to limit the scope of the disclosure.

In certain embodiment, the viscosity of petrolatum used in the formulation is about 150,000 centipoise at 25° C. An exemplary viscosity range for the petrolatum used in the formulation of the present disclosure is between about 20,000 centipoise and 600,000 centipoise at 25° C.

In certain embodiment, the compositions disclosed herein have a low viscosity such that the compositions may be applied from spray bottle with a spray pump or a container equipped with an atomizing head in the form of a mist onto a desired body parts, including but not limited to, face, lips, legs, face, etc. In certain embodiments, the spray pump bottle is configured to spray a mist of the composition onto the user's skin. In certain aspects, the spray pump bottle is configured to spray a mist.

In certain embodiments, the disclosed compositions have a viscosity of 3 to 500 centipoise ("cP"), 3 to 100 cP, 3 to 75 cP, 3 to 40 cP, 3 to 10 cP, 3 to 5 cP, 500 to 1,000 cP, 1,000-5000 cP, 5,000-7,000 cP at a temperature ranging from 65° F. to 100° F., from 70° F. to 85° F., and from 72° F. to 80° F.

In certain embodiments, the sprayable formulation has particle sizes from 50 to 100 microns, 10-50 microns, 5-10 microns or 1-5 microns.

In certain embodiments, to further aid in solubility and dispensability of the compositions by, for example, reducing overall composition viscosity, water is included at a concentration of 1 to 70 wt %, 1 to 15 wt %, 1 to 10 wt %, 2 to 65 wt %, 2 to 8 wt %, 2 to 6 wt %, 3 to 60 wt %, or 3 to 5 wt % of the overall composition. In certain embodiments, water aids in solubilizing various components and further acts synergistically to moisturize and aid in moisture retention of the user's skin.

In certain embodiments, in order to provide a sprayable formulation, a gradual reduction of viscosity with constant shear (finite amount of time required to change from high viscosity to low viscosity at a constant shear rate) is required. The present disclosure provides a formulation with reduced viscosity and increasing shear rate so as to provide an immediate change proportional to the amount of shear allowing for a sprayable formulation, while also allowing the formulation to remain sufficiently viscous to suspend the composition when under low or no shear. In certain embodiments, the formulation has minimal coalescing, does not agglomerate or otherwise settle out of solution when no shear is applied to the formulation. In certain embodiments, when shear is applied to the formulation, it is able to be sprayed. In certain embodiments, when the formulation hits the skin and there is no applied shear, the formulation will again thicken such that it will not run off the surface of the skin and therefore create an even coating on the skin.

In certain embodiments, the compositions exhibit lower viscosity, enhanced processability, and/or improved sprayability compared to existing composition comprising petrolatum. By sprayable it means that the formulation is dispensed through a hand-held spray dispenser by pressing a dispensing button to spray the formulation onto the skin. Any conventional spray dispenser may be used to dispense the skin protectant formulation including aerosol or pressurized propellant dispensers, motor driven pump dispensers, or dispensers using manual spray pump mechanisms.

Also disclosed is a container configured for dispensing a mist or aerosol, the container including a reservoir containing a formulation disclosed herein; and a nozzle that is fluidly connected to the reservoir, the nozzle adapted for dispensing the formulation as mist or aerosol. In certain embodiments, spray bottle includes a pump that draws liquid (i.e., the formulation) from a reservoir up a siphon tube and forces it through a nozzle. Depending on the sprayer, the nozzle of spray bottle may or may not be adjustable, so as to select between squirting a stream or mist. In certain embodiment, the spray container is a multi-angle spray head/dispenser. In certain embodiments, the disclosed formulations may be further packaged, for example, in moisture resistant, hermetically sealed packaging that may be repeatedly opened and closed. In the alternative, this packaging may contain a single use amount of the disclosed formulation.

7. METHODS OF TREATMENT

The present disclosure provides methods of treating conditions of the skin of a subject by topically treating the skin with the composition. Exemplary ailments which may be treated using a topical composition are radiation dermatitis, thermal burns, dermatomyofibromas, myositis, burns, diaper rash, itching, acne, sunburn, windburn, fever blister, cold sore, insect bite, insect sting, poison ivy, poison oak, poison sumac, dermatitis, other skin conditions, skin discoloration. In certain embodiments, the topical composition is used to treat Stretch marks, wrinkles, age spots, facial and body scarring, heat or thermal burns, radiation (sun) burns, rosacea, chapped (dry) lips and other skin conditions.

In certain embodiment, the method comprises topical administration of the compositions to the affected area of the subject and is repeated from one to three times daily through-out the course of treatment.

The disclosure provides a method to fortify the epidermal barrier so as to prevent occupationally or environmentally induced or genetically predisposed cutaneous disorders.

Effective results in most cases are achieved by topical application of a thin layer over the affected area, or the area where one seeks to achieve the desired effect. Depending on the condition being addressed, its stage or degree, and whether application is done for therapeutic or preventive reasons, effective results are achieved with application rates of from one application every two or three days to four or more applications per day.

The present disclosure is generally applicable to the treatment of mammalian skin, including for example humans, domestic pets, and livestock and other farm animals.

8. CONDITIONS THAT MAY BE TREATED BY THE DISCLOSED COMPOSITIONS

Disclosed compositions will successfully treat and prevent diseases and disorders of the skin and mucous membranes which cause disruption or dysfunction of the epidermal barrier. As a result, these formulations may be effectively applied to any of the following situations and cutaneous conditions:

Aging, wrinkles, photodamage, stretch marks, scars, liver spots, sunburn, heat or thermal burns, ice burns and frostbites. In one embodiment, the composition may be used to treat bed sores.

Important causes of morbidity and mortality in premature infants less than 33 weeks of gestational age are fluid and electrolyte abnormalities, hypothermia, and infection with the skin being the portal of entry. The development of mature barrier function coincides with the deposition of adequate amounts of the three major epidermal lipids in appropriate proportions.

Eczematous dermatitis are a group of inflammatory hyperproliferative skin diseases characterized by poorly demarcated, scaly, itchy or tender patches that may involve wide-spread areas of the body. Two of the most common types are atopic and seborrheic dermatitis. Both have a genetic predisposition and display abnormalities of stratum corneum lipids and barrier function even in clinically uninvolved skin. The other major eczematous dermatitis result from environmental or occupational insults of solvents, chemicals, detergents, hot water, low ambient humidity, ultraviolet or X radiation. These disorders include allergic or irritant contact dermatitis, eczema craquele, photoallergic, phototoxic, or phytophotodermatitis, radiation, and stasis dermatitis. Eczema craquele begins as dehydrated or dry skin that reaches such severity that complete destruction of the epidermal barrier occurs, which results in inflammation and hyperproliferation. The predominant therapy for eczematous dermatitis comprises topical corticosteroids and systemic antihistamines with or without antibiotics. Unfortunately, the skin remains excessively sensitive for months after the apparent clinical resolution of the lesions which results in rapid rebound of the lesions with significantly less environmental insult. Therefore, there is a great need for an effective therapeutic formulation that will normalize the barrier of both clinically uninvolved and involved skin to prevent disease exacerbations and/or limit disease extent.

Ulcers and erosions result from trauma or ischemia of the skin or mucous membranes. These insults include chemical or thermal burns, and vascular compromise as in venous, arterial, embolic or diabetic ulcers. The lesions are not only painful but form a portal for pathogenic microbes. Current therapy consists primarily of antibiotics, occlusive dressings, and vascular compression bandages.

The ichthyoses are a group of incurable, disfiguring common to rare genetic diseases characterized by disorders of abnormal epidermal cornification with or without associated abnormal barrier function and epidermal hyperproliferation. The palliative treatments for these diseases consist of systemic and topical retinoids, and topical α-hydroxy and salicylic acids. These modalities can produce significant topical irritation and both systemic retinoids and topical salicylic acid carry a significant risk of serious systemic toxicity.

The epidermolysis bullosae are a group of rare genetic diseases resulting from an absence or defect in epidermal/dermal cohesion. Cutaneous trauma to normal skin with normal daily activity results in complete or partial loss of the epidermis producing blisters, erosions, and ulcers. The only therapy for one type is diphenylhydantoin and/or systemic retinoids. Both treatments produce a significant number of severe systemic side effects with chronic usage.

Psoriasis is a markedly hyperproliferative, inflammatory papulosquamous disease characterized by sharply demarcated, scaly plaques most frequently located at areas of the body which suffer trauma, specifically knees, elbows, hands, feet, and scalp. Nearly all of the currently available topical and systemic therapies carry a significant risk of systemic and/or cutaneous toxicity. Moreover, these treatments generally are followed by a rapid rebound of the disease when they are withdrawn. None of these treatments repair the barrier and some actually worsen it. The current medications include retinoids, corticosteroids, sulfones, antineoplastic agents, anthralin, tar, psoralens and ultraviolet A or B light. It has recently been reported that prolonged remission was achieved in 60% of lesions treated with weekly applications of occlusive tape for a 10-week period. This modality artificially restores epidermal barrier function to some degree.

The cutaneous changes of intrinsic aging and photoaging (dermatoheliosis) result from environmental ravages combined with intrinsic changes which produce atrophy, fragility, inelasticity, decreased cell cohesion, hypoproliferation, and delayed healing after insults to the barrier. The stratum corneum lipids display a depletion of ceramide and nonpolar lipid species with a relative increase in cholesterol. The current treatments consist of topical application of retinoids or α-hydroxy acids, both of which often produce irritation, especially in the elderly.

In certain embodiments, the disclosed composition is used for preventing or treating dry skin, rash, diaper rash, irritation and itch relief, chap lips, poison ivy, oak and sumac, sunburn, windburn, frostbite. In certain embodiments, the disclosed composition is used as cough suppressant, wound healing, skin healing, cosmetic and beauty products, baby care products, lip balm, sunscreen.

The limiting factor for occupational or athletic performance, even for the occasional recreational athlete is frictional blistering of the skin by mechanical shearing forces. Prevention with layered clothing or application of synthetic films are the only currently available, somewhat helpful remedies.

The major limiting factor for the topical use of corticosteroids, especially in the young and elderly is cutaneous atrophy which predisposes to infection and slows the rate of healing. Topical retinoids and α-hydroxy acids may partially reverse the atrophy, but the irritation potential of these agents is significantly increased.

There are many known or potential therapeutic compounds whose utility has been prevented or is compromised because of cutaneous irritation or barrier disruption. A formulation comprising these compounds incorporated with the lipids of this disclosure will expand the therapeutic armamentarium potentially available to physicians.

The integrity of the epidermal barrier is known to be the major factor that regulates epidermal DNA synthesis. It is also known that maintenance of a normal epidermal barrier will inhibit epidermal hyperproliferation. The discoveries of the present disclosure, therefore, lead to treatments for hyperproliferative cutaneous diseases, notable examples of which are papulosquamous and eczematous diseases.

In some embodiments, the benefit of the treatment of the present disclosure includes other areas of the subject being treated beyond the skin. In some embodiments, the compositions of the present disclosure treat the respiratory system of the subject. Common respiratory disorders and diseases that may be treated include chronic obstructive pulmonary disease, asthma, bronchitis, respiratory distress, occupational lung diseases, pulmonary hypertension. The present compositions can also treat symptoms related to the effect of tobacco smoke irritation, air pollution, occupational chemicals and dusts, and infections in the lower and upper respiratory system. In some embodiments, the present compositions can also treat synovial infusion, edema, and inflammation in the joints, including but not limited to arthritis.

9. METHOD OF MAKING THE FORMULATIONS

All compounding, filling and storage procedures follow cGMP requirements. All equipment and tools that are in contact with individual ingredients are cleaned, sanitized and dried prior to use. All ingredients are stored in a clean, dry and temperature-controlled area between 15° C. and 25° C. The ingredients are set up at the main mixing area. They are approved for use, weighed, measured and placed in separate, clean, properly identified labeled, suitable size tared containers.

Step 1: Snow White Petrolatum USP was added into a main reactor vessel that was equipped with a propeller mixer. The power and temperature of the main reactor vessel were controlled with variable speed controls. The Snow White Petrolatum USP was mixed under high speed and heat to 50° C.-55° C. and maintained at this temperature.

Step 2: In a separate vessel, additional components of the formulation were mixed and heated to 85° C.-90° C. until uniform. After the additional components are melted and well combined, the mixture was then slowly added to the main reactor vessel in step 1 and mixed until uniform. The temperature was maintained at 50° C.-55° C.

Step 3: In a separate vessel, additional components of the formulation were mixed until uniform and maintained at 50° C.-55° C. The mixture was then slowly added to the main reactor vessel of step 1 and mixed until uniform. The mixture in the main reactor vessel was then removed from the heat and homogenized until the uniformly dispersed.

Step 4: In a separate vessel, additional components of the formulation were mixed until uniform and added to the main reactor vessels of step 1 and mixed until uniform. This process was repeated until all ingredients were combined.

Step 5: Continue mixing the mixture in the main reactor vessel and cooling the mixture to 35° C. A sample of the mixture was then tested and approved.

10. EXAMPLES

The following examples are illustrative. Modifications will be apparent to, and can be readily made by, those skilled in the art without departing from the spirit and scope of the disclosure. The scope of the appended claims is not to be limited to the examples.

| INCI Name/Range of wt % and specific example | Minimum Wt % | Specific Wt % | Max Wt % |
| --- | --- | --- | --- |
| Snow White Petrolatum USP | 30 | 50.0 | 70 |
| Coconut Alkanes and Coco-Caprylate/Caprate | 30 | 47.5 | 65 |
| Ceramide(s) | 0.05 | 0.25 | 0.5 |
| Jojoba Oil/Macadamia Seed Oil Esters | 0.1 | 0.75 | 1.5 |
| Squalene | 0.1 | 0.37 | 1 |
| Phytosteryl Macadamiate | 0.01 | 0.063 | 0.1 |
| Phytosterol | 0.005 | 0.015 | 0.1 |
| Tocopherol | 0.001 | 0.0045 | 0.1 |
| *Ipomoea Batatas* Root Extract | 0.01 | 0.033 | 0.1 |

Example 1—Skin Protectant Spray

Example 2—Skin Protectant Spray

| Ingredients/Range of Wt % and specific example | Minimum Wt % | Specific Wt % | Max. Wt % |
| --- | --- | --- | --- |
| Petrolatum up to 60% | 30 | 50 | 60 |
| Coconut Alkanes | 30 | 45 | 70 |
| Coco-Caprylate/Caprate | 3 | 5 | 10 |
| C 18-36 Acid Triglyceride | 0.5 | 2 | 5 |
| *Ipomoea Batatas* Root Extract | 0.01 | 0.05 | 0.1 |
| Jojoba Oil/Macadamia Seed Oil Esters | 0.1 | 0.75 | 1.5 |
| Ceramide AP | 0.01 | 0.05 | 0.1 |
| Ceramide NP | 0.01 | 0.05 | 0.1 |
| Squalene | 0.1 | 0.37 | 1 |
| Tocopherol | 0.001 | 0.0045 | 0.1 |
| Phytosterols | 0.005 | 0.02 | 0.1 |
| C 12-18 Acid Triglyceride | 0.1 | 0.5 | 1 |
| Phytosteryl Macadamiate | 0.01 | 0.07 | 0.1 |
| Acacia Senegal Gum | 0.01 | 0.04 | 0.1 |
| Citric Acid | 0.001 | 0.003 | 0.01 |

INITIAL SPECIFICATIONS:

Appearance: Hazy, semi-viscous liquid
Color: Purple
Odor: Characteristic
pH: N/A
Viscosity (Brookfield DV-11+: Spindle T-E @ 10 rpm, 25° C. J: 3,500 cps Example 3—Skin Protectant Spray

| Ingredients/range of wt % and specific example | Minimum wt % | Specific wt % | Max wt % |
| --- | --- | --- | --- |
| Zinc Oxide 10.0%-15% | 10 | 12.5 | 15 |
| Water (Aqua) | 0.1 | 1 | 25 |
| Caprylic/Capric Triglyceride | 0.1 | 1 | 25 |
| Glycerin | 0.1 | 1 | 25 |
| Methyl Dihydroabietate | 0.01 | 1 | 10 |
| Propanediol | 1 | 10 | 25 |
| Cetearyl Alcohol | 0.01 | 1 | 10 |
| Bakuchiol | 0.01 | 1 | 10 |
| Bisabolol | 0.01 | 1 | 10 |
| Lactic Acid | 0.001 | 0.003 | 0.01 |
| Sodium Carboxymethyl Beta-Glucan | 0.01 | 1 | 10 |
| *Ipomoea Batatas* Root Extract | 0.01 | 0.05 | 0.1 |
| Cucumis Sativus (Cucumber) Fruit Extract | 0.01 | 0.05 | 0.1 |
| Vaccinium Myrtillus Fruit Extract | 0.01 | 0.05 | 0.1 |
| Garlic (Allium Sativum) Extract | 0.01 | 0.05 | 0.1 |
| Jojoba Esters | 0.1 | 0.75 | 1.5 |
| Coco-Glucoside | 0.001 | 0.1 | 1 |
| Citric Acid | 0.001 | 0.003 | 0.01 |
| Acacia Senegal Gum | 0.01 | 0.04 | 0.1 |
| Caprylhydroxamic Acid | 0.001 | 0.1 | 1 |
| Polyhydroxystearic Acid | 0.001 | 0.1 | 1 |
| Bentonite | 0.001 | 0.1 | 1 |
| Ethylhexylglycerin | 0.001 | 0.1 | 1 |
| Heptyl Undecylenate | 0.001 | 0.1 | 1 |
| Hexylene Glycol | 0.001 | 0.1 | 1 |
| Cetyl Glyceryl Ether | 0.001 | 0.1 | 1 |
| Caprylyl Glycol | 0.001 | 0.1 | 1 |
| Phenoxyethanol | 0.001 | 0.1 | 1 |

INITIAL SPECIFICATIONS:

Appearance: Opaque, semi-viscous lotion
Color: Purple
Odor: Characteristic
pH: 7.15
Viscosity (Brookfield DV-II+: Spindle RV-5 @ 10 rpm, 25° C.): 7,000 cps Example 4—Skin Protectant Spray

| Ingredients/range of weight % and specific example | Minimum wt % | Specific wt % | Max wt % |
| --- | --- | --- | --- |
| Zinc Oxide 10.0%-15% | 10 | 12.5 | 15 |
| Coconut Alkanes | 30 | 45 | 70 |
| Dimethicone | 1 | 2.5 | 5 |
| Isohexadecane | 0.01 | 1 | 10 |

-continued

| Ingredients/range of weight % and specific example | Minimum wt % | Specific wt % | Max wt % |
|---|---|---|---|
| Coco-Caprylate/Caprate | 3 | 5 | 10 |
| Methyl Dihydroabietate | 0.01 | 1 | 10 |
| Silica | 0.01 | 1 | 10 |
| *Ipomoea Batatas* Root Extract | 0.01 | 0.05 | 0.1 |
| Triethoxycaprylylsilane | 0.01 | 1 | 10 |
| Acacia Senegal Gum | 0.01 | 0.04 | 0.1 |
| Citric Acid | 0.001 | 0.003 | 0.01 |

INITIAL SPECIFICATION:

Appearance: Opaque, semi-viscous lotion
Color: Purple
Odor: Characteristic
pH: N/A
Viscosity: N/A

Example 5—Skin Protectant Spray

| Ingredients/Range of Wt % and specific example | Minimum wt % | Specific wt % | Max wt % |
|---|---|---|---|
| Zinc Oxide 15.0% | 10 | 12.5 | 15 |
| Petrolatum | 30 | 50 | 70 |
| Coconut Alkanes | 30 | 45 | 70 |
| Coco-Caprylate/Caprate | 3 | 5 | 10 |
| C18-36 Acid Triglyceride | 0.5 | 1.38 | 5 |
| Water (Aqua) | 0.1 | 1 | 25 |
| Caprylic/Capric Triglyceride | 0.1 | 1 | 25 |
| Glycerin | 0.1 | 1 | 25 |
| Methyl Dihydroabietate | 0.01 | 1 | 10 |
| Propanediol | 1 | 10 | 25 |
| Cetearyl Alcohol | 0.01 | 1 | 10 |
| Bakuchiol | 0.01 | 1 | 10 |
| Bisabolol | 0.01 | 1 | 10 |
| Lactic Acid | 0.001 | 0.003 | 0.01 |
| Sodium Carboxymethyl Beta-Glucan | 0.01 | 1 | 10 |
| *Ipomoea Batatas* Root Extract | 0.01 | 0.05 | 0.1 |
| *Cucumis Sativus* (Cucumber) Fruit Extract | 0.01 | 0.05 | 0.1 |
| *Vaccinium Myrtillus* Fruit Extract | 0.01 | 0.05 | 0.1 |
| Garlic (*Allium Sativum*) Extract | 0.01 | 0.05 | 0.1 |
| Jojoba Esters | 0.1 | 0.75 | 1.5 |
| Coco-Glucoside | 0.001 | 0.1 | 1 |
| Citric Acid | 0.001 | 0.003 | 0.01 |
| Acacia Senegal Gum | 0.01 | 0.04 | 0.1 |
| Caprylhydroxamic Acid | 0.001 | 0.1 | 1 |
| Polyhydroxystearic Acid | 0.001 | 0.1 | 1 |
| Bentonite | 0.001 | 0.1 | 1 |
| Ethylhexylglycerin | 0.001 | 0.1 | 1 |
| Heptyl Undecylenate | 0.001 | 0.1 | 1 |
| Hexylene Glycol | 0.001 | 0.1 | 1 |
| Cetyl Glyceryl Ether | 0.001 | 0.1 | 1 |
| Caprylyl Glycol | 0.001 | 0.1 | 1 |
| Phenoxyethanol | 0.001 | 0.1 | 1 |

INITIAL SPECIFICATIONS:

Appearance: Opaque, semi-viscous lotion
Color: Purple
Odor: Characteristic
pH: 7.15
Viscosity (Brookfield DV-II+: Spindle RV-5 @ 10 rpm, 25° C.): 7,000 cps In a separate example, the above formulation comprises 15% ZnO; 40% petrolatum, and the coconut alkanes and coco-Caprylate/Caprate are replaced with 45% isohexadecane.

Example 6—Skin Protectant Spray

| Ingredients/range of weight % and specific example | Minimum wt % | Specific wt % | Max. wt % |
|---|---|---|---|
| Zinc Oxide 15.0% | 10 | 12.5 | 15 |
| Petrolatum | 30 | 50 | 70 |
| Coconut Alkanes | 30 | 45 | 70 |
| Coco-Caprylate/Caprate | 3 | 5 | 10 |
| C18-36 Acid Triglyceride | 0.5 | 1.38 | 5 |
| Dimethicone | 1 | 2.5 | 5 |
| Isohexadecane | 0.01 | 1 | 10 |
| Methyl Dihydroabietate | 0.01 | 1 | 10 |
| Silica | 0.01 | 1 | 10 |
| *Ipomoea Batatas* Root Extract | 0.01 | 0.05 | 0.1 |
| Triethoxycaprylylsilane | 0.01 | 1 | 10 |
| Acacia Senegal Gum | 0.01 | 0.04 | 0.1 |
| Citric Acid | 0.001 | 0.003 | 0.01 |

Appearance: Opaque, semi-viscous lotion
Color: Purple
Odor: Characteristic
pH: N/A
Viscosity: N/A In a separate example, the above formulation comprises 15% ZnO; 40% petrolatum, and the coconut alkanes and coco-Caprylate/Caprate are replaced with 45% isohexadecane.

Example 7—Skin Protectant Spray

| INCI Name/Range of wt % | Minimum wt % | Specific wt % | Max wt % |
|---|---|---|---|
| Petrolatum USP | 30 | 50 | 70 |
| Coconut Alkanes and Coco-Caprylate/Caprate | 30 | 46 | 70 |
| C18-36 Acid Triglyceride | 0.5 | 1.5 | 5 |
| Ceramide(s) | 0.02 | 0.1 | 0.5 |
| Jojoba Oil/Macadamia Seed Oil Esters | 0.1 | 1 | 2.5 |
| Squalene | 0.1 | 0.5 | 1 |
| Phytosteryl Macadamiate | 0.01 | 0.06 | 0.1 |
| Phytosterol | 0.05 | 0.15 | 0.2 |
| Tocopherol | 0.01 | 0.0045 | 0.25 |
| *Ipomoea Batatas* Root Extract | 0.01 | 0.05 | 5 |
| C12-18 Acid Triglyceride | 0.1 | 0.5 | 1 |
| Acacia Senegal Gum | 0.001 | 0.02 | 0.1 |
| Maltodextrin | 0.001 | 0.03 | 0.1 |
| Citric Acid | 0.001 | 0.03 | 0.1 |

Example 8—Skin Protectant Spray

| Ingredients/Range of wt % | Minimum wt % | Specific wt % | Max wt % |
|---|---|---|---|
| Petrolatum (Snow White petrolatum USP) | 30 | 50 | 70 |
| Coconut Alkanes | 30 | 42.12 | 70 |
| Coco-Caprylate/Caprate | 3 | 4.68 | 7 |
| C18-36 Acid Triglyceride | 0.5 | 1.38 | 5 |
| C12-18 Acid Triglyceride | 0.1 | 0.42 | 1 |
| Ceramide NP | 0.01 | 0.05 | 0.1 |
| Ceramide AP | 0.01 | 0.05 | 0.1 |
| Jojoba Esters | 0.1 | 0.75 | 1.5 |
| Squalene | 0.1 | 0.37 | 1 |
| Phytosteryl Macadamiate | 0.01 | 0.063 | 0.1 |
| Phytosterols | 0.005 | 0.15 | 0.1 |
| Tocopherol | 0.001 | 0.0045 | 0.1 |
| *Ipomoea Batatas* Root Extract | 0.01 | 0.033 | 0.1 |

Example 9—Skin Protectant Spray

-continued

| Ingredients/Range of wt % | Minimum wt % | Specific wt % | Max wt % |
|---|---|---|---|
| Citric Acid | 0.001 | 0.003 | 0.01 |
| Acacia Senegal Gum | 0.001 | 0.033 | 0.1 |
| Maltodextrin | 0.001 | 0.031 | 0.1 |

Example 9—Skin Protectant Spray

| Ingredients: | % wt/wt | % Breakdown | INCI name |
|---|---|---|---|
| Snow White petrolatum USP | 50.0 | 100.0 | Petrolatum |
| Vegesil 345 | 46.8 | 90.0 | (i)Coconut Alkanes |
|  |  | 10.0 | (ii) Coco-Caprylate/Caprate |
| Ceramide IIIB | 0.05 | 100.0 | Ceramide NP |
| Ceramide VI | 0.05 | 100.0 | Ceramide AP |
| L22 | 3.0 | 25.0 | (i) Jojoba Esters |
|  |  | 12.25 | (ii) Squalene |
|  |  | 2.1 | (iii) Phytosteryl Macadamiate |
|  |  | 0.5 | (iv) Phytosterols |
|  |  | 0.15 | (v) Tocopherol |
|  |  | 46.0 | (vi) C18-36 Acid Triglyceride |
|  |  | 14.0 | (vii) C12-18 Acid Triglyceride |
| Natpure Xfine Potato SP313 | 0.1 | 33.0 | (i)*Ipomoea Batatas* Root Extract |
|  |  | 3.0 | (ii) Citric Acid |
|  |  | 33.0 | (iii) Acacia Senegal Gum |
|  |  | 31.0 | (iv) Maltodextrin |
| Physical Properties: |  | Specification limits: |  |
| Appearance: |  | Translucent, slightly viscous gel |  |
| Color: |  | Purple |  |
| Odor: |  | Characteristic |  |
| Specific Gravity @ 25° C. |  | 0.78-0.83 |  |
| Viscosity @ 25° C. (Brookfield DVII+: Spindle RV-4 @ 10 rpm, 1 min) |  | 1,000 cps-5,000 cps |  |
| Supplementary Tests Petrolatum in the range of 40.0%-60.0% |  |  |  |
| Microbiological Tests |  | Less than 10 CFU/g |  |
| Aerobic plate count |  | Less than 10 CFU/g |  |
| Yeast and mold |  |  |  |

Example 10—Skin Protectant Spray

| INCI Name/ Specific Wt % | Minimum wt % | Specific wt % | Max. wt % |
|---|---|---|---|
| Snow White Petrolatum USP | 30 | 65 | 50 |
| Coconut Alkanes and Coco-Caprylate/Caprate | 65 | 30 | 45-47.5 |
| Ceramide(s) | 0.05-0.5 | 0.05-0.5 | 0.05-0.5 |
| Jojoba Oil/Macadamia Seed Oil Esters | <5.0 | <5.0 | 2.5 |
| Squalene | <2.0 | <1.0 | <0.5 |
| Phytosteryl Macadamiate | 0.01-0.1 | 0.01-0.1 | 0.01-0.1 |
| Phytosterol | 0.05-0.3 | 0.05-0.3 | <0.2 |
| Tocopherol | 0.01-0.25 | 0.01-0.25 | <0.05 |
| *Ipomoea Batatas* Root Extract | 0.01-5 | 0.01-5 | <0.1 |

Example 11—Radiation Spray

| Ingredients/Range of Wt % and specific example | Minimum wt % | Specific wt % | Max wt % |
|---|---|---|---|
| Petrolatum | 30 | 50 | 70 |
| Coconut Alkanes | 30 | 45 | 70 |
| Coco-Caprylate/Caprate | 3 | 5 | 10 |
| Lidocaine | 0.01 | 0.1 | 10 |
| INITIAL SPECIFICATIONS: |  |  |  |

Appearance: Hazy, non-viscous oil
Color: Straw
Odor: Characteristic

Example 12—Vapor Spray

| Ingredients/Range of Wt % and specific example | Minimum wt % | Specific wt % | Max wt % |
|---|---|---|---|
| Petrolatum | 30 | 50 | 70 |
| Coconut Alkanes | 30 | 45 | 70 |
| Coco-Caprylate/Caprate | 3 | 5 | 10 |
| Camphor | 1 | 2.5 | 5 |
| Menthol | 1 | 2.5 | 5 |
| *Eucalyptus Globulus* Leaf Oil | 1 | 2.5 | 5 |
| *Myristica Fragrans* (Nutmeg) Kernel Oil | 0.1 | 1 | 5 |
| Turpentine Oil | 0.1 | 1 | 5 |
| C18-C36 Acid Triglyceride | 0.5 | 1.5 | 5 |
| Jojoba Esters | 0.1 | 0.75 | 1.5 |
| C12-C18 Acid Triglyceride | 0.1 | 0.5 | 1 |
| Squalene | 0.1 | 0.5 | 1 |
| Thymol | 0.1 | 0.5 | 1 |
| Phytosteryl Macadamiate | 0.01 | 0.06 | 0.1 |
| Phytosterols | 0.005 | 0.015 | 0.1 |
| Tocopherol | 0.001 | 0.0045 | 0.1 |
| INITIAL SPECIFICATIONS: |  |  |  |

Appearance: Hazy, non-viscous oil
Color: Straw
Odor: Characteristic

Example 13—Method of Making the Formulation

Individual ingredients were weighed and measured and placed in separate, clean, properly identified suitable size tared containers.

Step 1: Snow White Petrolatum USP was added into a main reactor vessel that was equipped with a propeller mixer. The power and temperature of the main reactor vessel were controlled with variable speed controls. The Snow White Petrolatum USP was mixed under high speed and heat to 50° C.-55° C. and maintained at this temperature.

Step 2: In a separate vessel, Vegesil and ceramides were mixed and heated to 85° C.-90° C. until uniform. After the Vegesil and ceramides are melted and well combined, the mixture was then slowly added to the main reactor vessel in step 1 and mixed until uniform. The temperature was maintained at 50° C.-55° C.

Step 3: In a separate vessel, L22 and Natpure Xfine Potato were mixed until uniform and maintained at 50° C.-55° C. The mixture was then slowly added to the main reactor vessel of step 1 and mixed until uniform. The mixture in the main reactor vessel was then removed from the heat and homogenized until the Natpure Xfine Potato SP313 was uniformly dispersed.

Step 4: Continue mixing the mixture in the main reactor vessel and cooling the mixture to 35° C. A sample of the mixture was then tested and approved.

Exemplary Products, Systems and Methods are Set Out in the Following Items:

1. A skin barrier protective delivery system comprising:
   (i) a mixture of Coconut Alkanes at a concentration range of 30-70 wt % and Coco-Caprylate/Caprate at a concentration range of 3-7 wt %; and
   (ii) petrolatum, wherein the petrolatum is present at a concentration of at least 30 wt %,
   wherein the delivery system is sprayable.
2. The skin barrier protective delivery system of item 1, wherein the mixture of Coconut Alkanes and Coco-Caprylate/Caprate is present at a concentration range of 30 wt %-65 wt %.
3. The skin barrier protective delivery system of item 1, wherein the mixture of Coconut Alkanes and Coco-Caprylate/Caprate is present at a concentration of at most 70 wt %.
4. The skin barrier protective delivery system of item 1, wherein the petrolatum is present at a concentration of about 40%.
5. The skin barrier protective delivery system of item 1, wherein the petrolatum is present at a concentration of about 50%.
6. The skin barrier protective delivery system of item 1, further comprising at least one of a ceramide, a triglyceride, a phytosterol, a phytosterol ester, a terpene, a plant-based ester or wax, tocopherol and/or a phospholipid.
7. The skin barrier protective delivery system of item 6, comprising at least two of a ceramide, a triglyceride, a phytosterol, a phytosterol ester, a terpene, a plant-based ester or wax, tocopherol and/or a phospholipid.
8. The skin barrier protective delivery system of item 6, comprising at least three of a ceramide, a triglyceride, a phytosterol, a phytosterol ester, an isohexadecane, a terpene, a plant-based ester or wax, tocopherol and/or a phospholipid.
9. The skin barrier protective delivery system of any one of items 4 to 8, wherein the plant-based ester or wax is selected from the group consisting of jojoba oils, jojoba esters, candelilla wax, carnauba wax, rice bran wax and sunflower wax.
10. The skin barrier protective delivery system of item 9, wherein the plant-based ester or wax comprises jojoba esters.
11. The skin barrier protective delivery system of any one of items 4 to 8, wherein the terpene is selected from the group consisting of a triterpene, a hemiterpene, a monoterpene, a sesquiterpene, a diterpene, a sesterterpene and a tetraterpene.
12. The skin barrier protective delivery system of item 10, wherein the terpene is a triterpene.
13. The skin barrier protective delivery system of item 12, wherein the triterpene is squalene.
14. The skin barrier protective delivery system of any one of items 4 to 8, wherein the phytosterol ester comprises esters derived from a seed or nut oil.
15. The skin barrier protective delivery system of item 14, wherein the seed or nut oil is selected from the group consisting of macadamia oil, almond oil, avocado oil, canola oil, coconut oil, corn oil, cottonseed oil, grapeseed oil, hazelnut oil, palm oil peanut oil, pine seed oil, pecan oil pumpkin seed oil, safflower oil, sesame oil, soy oil, sunflower oil, and walnut oil.
16. The skin barrier protective delivery system of item 15, wherein the phytosterol ester is phytosteryl macadamiate.
17. The skin barrier protective delivery system of item 1, comprising a ceramide, a triglyceride, a phytosterol, phytosterol macadamiate, squalene, jojoba esters, and tocopherol.
18. The skin barrier protective delivery system of item 1, comprising ceramide NP, ceramide AP, jojoba esters, squalene, phytosterols, phytosteryl macadamiate, tocopherol, C18-C36 acid triglyceride, and C12-18 acid triglyceride.
19. The skin barrier protective delivery system of any one of the preceding items, further comprising at least one of a polysaccharide, a gum, a buffering agent, and a root plant extract.
20. The skin barrier protective delivery system of item 19, wherein the polysaccharide is selected from the group consisting of maltodextrin, cellulose, hydroxyethylcellulose, hydroxypropylcellulose, carboxymethylcellulose, starch, hydrolyzed starch, partially hydrolyzed starch, xylans, inulin, cellobiose, scleroglucan, chitosan, ulvan, fucoidan, alginate, pectin, heparin, hyaluronic acid, and mixtures thereof.
21. The skin barrier protective system of item 19 or 20, wherein the polysaccharide is maltodextrin.
22. The skin barrier protective delivery system of item 19, wherein the gum is selected from the group consisting of guar gums, xanthan gums, pullulan gums, agar-agar gums, carrageenan gums, gellan gums, gum arables, and tragacanth gums.
23. The skin barrier protective system of item 19, wherein the gum is *Acacia senegal* gum.
24. The skin barrier protective delivery system of item 19, wherein the root plant extract is derived from a root plant selected from the group consisting of sweet potato, potato, beet, carrot, parsnip, horseradish and radish.
25. The skin barrier protective delivery system of item 24, wherein the root plant extract is *Ipomoea batatas* root extract.
26. The skin barrier protective delivery system of item 19, wherein the acid is citric acid.
27. The skin barrier protective delivery system of item 19, comprising at least one of *Ipomoea batatas* root extract, citric acid, *Acacia senegal* gum, and maltodextrin.
28. The skin barrier protective delivery system of item 19, comprising *Ipomoea batatas* root extract, citric acid, *Acacia senegal* gum, and maltodextrin.
29. The skin barrier protective delivery system of item 1, comprising ceramide NP, ceramide AP, jojoba esters, squalene, phytosterols, phytosteryl macadamiate, tocopherol, C18-C36 acid triglyceride, C12-18 acid triglyceride, *Ipomoea batatas* root extract, *Acacia senegal* gum, citric acid, and maltodextrin.
30. The skin barrier protective delivery system of item 1, wherein the ratio of the mixture of Coconut Alkanes and/or Coco-Caprylate/Caprate to Petrolatum is about 1:1
31. The skin barrier protective delivery system of item 1, comprising:
    (i) at least 30 wt % Petrolatum;
    (ii) Coconut Alkanes in the range of 30-70 wt %;
    (iii) Coco-Caprylate/Caprate in the range of 3-7 wt %;
    (iv) ceramide NP in the range of 0.01-0.1 wt %;
    (v) ceramide AP in the range of 0.01-0.1 wt %;
    (vi) Jojoba Esters in the range of 0.1-1.5 wt %;

(vii) Squalene in the range of 0.1-1 wt %;
(viii) Phytosteryl Macadamiate in the range of 0.01-0.1 wt %;
(ix) Phytosterols in the range of 0.005-0.1 wt %;
(x) Tocopherol in the range of 0.001-0.1 wt %;
(xi) C18-36 Acid Triglyceride in the range of 0.5-5 wt %;
(xii) C12-18 Acid Triglyceride in the range of 0.1-1 wt %;
(xiii) *Ipomoea batatas* root extract in the range of 0.01-0.1 wt %;
(xiv) citric acid in the range of 0.001-0.01 wt %;
(xv) *Acacia senegal* gum in the range of 0.001-0.1 wt %; and
(xvi) Maltodextrin in the range of 0.001-0.1 wt %,
wherein the delivery system is a sprayable formulation.

32. The skin barrier protective delivery system of item 31, comprising:
(i) 50 wt % Petrolatum;
(ii) 42-43 wt % Coconut Alkanes;
(iii) 4-5 wt % Coco-Caprylate/Caprate;
(iv) 0.05 wt % ceramide NP;
(v) 0.05 wt % ceramide AP;
(vi) 0.75 wt % Jojoba Esters;
(vii) 0.3-0.4 wt % Squalene;
(viii) 0.05-0.06 wt % Phytosteryl Macadamiate;
(ix) 0.01-0.02 wt % Phytosterols;
(x) 0.0045 wt % Tocopherol;
(xi) 1-2 wt % C18-36 Acid Triglyceride;
(xii) 0.4-0.5 wt % C12-18 Acid Triglyceride;
(xiii) 0.03-0.04 wt % *Ipomoea batatas* root extract;
(xiv) 0.003-0.004 wt % citric acid;
(xv) 0.03-0.04 wt % *Acacia senegal* gum; and
(xvi) 0.03-0.04 wt % Maltodextrin.

33. The skin barrier protective delivery system of any one of the preceding items, further comprising zinc oxide.

34. A skin barrier protective delivery system comprising
(i) 25-60 wt % Petrolatum;
(ii) 10-25 wt % zinc oxide (ZnO); and
(iii) 30-60 wt % Isohexadecane.

35. A skin barrier protective delivery system comprising
(i) 40 wt % Petrolatum;
(ii) 15 wt % zinc oxide (ZnO); and
(iii) 45 wt % Isohexadecane.

36. The skin barrier protective delivery system of any one of the preceding items, having a viscosity of from about 500 cps to about 10,000 cps.

37. The skin barrier protective delivery system of any one of the preceding items, having a viscosity of from about 1,000 cps to about 5,000 cps.

38. The skin barrier protective delivery system of any one of the preceding items, further comprising an active ingredient.

39. The skin barrier protective delivery system of item 35, wherein the active ingredient is present in an amount of from about 0.0001% to about 35% by weight.

40. The skin barrier protective delivery system of item 35 or 36, wherein the active ingredient is selected from the group consisting of an antifungal agent, an antibacterial agent, an antiviral agent, an anti-acne agent, an anti-aging agent, an anti-pruritic agent, a UV absorbing agent, a sunscreen agent, a skin pigment modulating agent, a skin lightening agent, a skin darkening agent, a hair growth enhancing agent, a hair growth inhibiting agent, an antidandruff agent, an anti-seborrheic agent, an anti-psoriasis agent, a hair removal agent, an exfoliating agent, a wound healing agent, an anti-inflammatory agent, a blood microcirculation improvement agent, a sebum modulating agent, a hormone, an immune modulating agent, a botanical extract, a moisturizing agent, an emollient, an astringent, an antiperspirant, a vitamin, a retinoid, a cleansing agent, a sensory agent, a color change agent, an antibiotic, an anti-irritant, an anesthetic, an analgesic, a steroid, a tissue healing agent, a tissue regenerating agent, a collagen or elastin boosting agent, a skin protectant agent, an agent to promote excess fat reduction or cellulite control or body toning benefits, an amino acid, a peptide, a mineral, a hydroxy acid, an anti-emetic agent, an anti-anginal agent, a bronchodilator agent, osteoporosis treatment agent, an anti-depressant agent, an anti-migraine agent, smoking cessation agent, anti-diarrheal agent, anti-ulcer agent, mood disorder agent, anti-obesity agents, erectile dysfunction control agents, anti-Parkinson agents, MAO inhibitors, sleep disorder agents, anti-diabetic agents, and combinations thereof.

41. The skin barrier protective delivery system of any one of the preceding items, further comprising a skin whitening agent selected from the group consisting of hydroquinone, arbutin, hydroquinone derivatives, Paper Mulberry extract (*Broussonetia kazinoke*), Mitracarpe extract (*Mitracarpus scaber*), Bearberry extract (*Arctostaphylos uva ursi*), Yellow Dock extract (*Rumex crispus* and *Rumex occidentalis*), Glutathione, Leucocyte extract, *Aspergillus orizae* extract (*Aspergillus orizae*), Licorice Root extract (*Glycyrrhiza glabra*), Rosmarinic acid (*Rosmarinus officinalis*), Tetrahydrocurcumin, Green Tea extract (*Camellia sinensis*), Yohimbe extract (*Pausinystalia yohimbe*), Ecklonia cava extract, niacinamide, Hydroxytetronic acid, *Spondias mombin* extract, *Maprounea guianensis* extract, *Walteria indica* extract, *Gouania blanchetiana* extract, *Cordia schomburgkii* extract, *Randia armata* extract, *Hibiscus furcellatus* extract, and combinations thereof.

42. The skin barrier protective delivery system of any one of the preceding items, further comprising an antioxidant selected from the group consisting of Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, Emblica extract, and combinations thereof.

43. The skin barrier protective delivery system of any one of the preceding items, further comprising a UVA/UVB sunscreen agent is selected from the group consisting of Titanium dioxide, Zinc oxide, Galanga extract (*Kaempferia galanga*), Benzophenone-3, Benzophenone-4, Ethylhexyl Methoxycinnamate, Homosalate, Ethylhexyl salicylate, Octocrylene, Menthyl anthranilate, Avobenzone, Lawsone, Sulisobenzone, Trolamine salicylate, Lawsone, Glyceryl aminobenzoate, Cinoxate, PABA, and combinations thereof.

44. The skin barrier protective delivery system of any one of the preceding items, further comprising a pharmaceutically acceptable carrier selected from the group consisting of water and oil emulsions, suspensions, colloids, microemulsions, clear solutions, suspensions of nanoparticles, emulsions of nanoparticles, or anhydrous compositions.

45. The skin barrier protective delivery system of any one of items 1-44, which does not comprise a flammable component.

46. The skin barrier protective delivery system of item 45, which is free of a flammable solubilizer or alcohol.

47. A pharmaceutical composition comprising the skin barrier protective delivery system of any one of the preceding items.

48. A pharmaceutical composition in the form of a sprayable gel, comprising the skin barrier protective delivery system of any one of the preceding items.

49. A device comprising the pharmaceutical composition according to item 47 or 48.

50. The device of item 49, wherein the device does not comprise a propellant or aerosol or bag-on-valve.

51. The device of item 49 or 50, wherein the device is in the form of an atomizer pump.

52. The device of item 51, wherein the device is a dip tube atomizer pump.

53. A method for protecting skin of a subject in need thereof, comprising administering to the skin of the subject the skin barrier protective delivery system of any one of items 1-46, a pharmaceutical composition according to item 47 or 48, or the device of any one of items 49-52.

54. A skin barrier protective delivery system comprising: (i) a mixture of long chain Alkanes having a carbon length greater than 10 carbons, wherein the long chain Alkanes are present at a concentration range of 30-70 wt %; and (ii) petrolatum, wherein the petrolatum is present at a concentration of at least 30 wt %, wherein the delivery system is sprayable.

55. A skin barrier protective delivery system comprising: (i) a mixture of long chain Alkanes having a carbon length greater than 10 carbons at a concentration range of 30-70 wt % and esters of long chain alcohols at a concentration of 3-7 wt %; and (ii) petrolatum, wherein the petrolatum is present at a concentration of at least 30 wt %, wherein the delivery system is sprayable.

56. The skin barrier protective delivery system of item 54 or 55, in the form of a sprayable gel.

57. A skin barrier protective delivery system comprised of: (a) a mixture of Coconut Alkanes and Coco-Caprylate/Caprate and (b) Petrolatum, wherein the petrolatum is present at a concentration of at least 30%, and the ratio of (a) to (b) is from 7:3 to 1:3.

58. A skin barrier protective delivery system consisting essentially of: (a) a mixture of Coconut Alkanes and Coco-Caprylate/Caprate and (b) Petrolatum, wherein the petrolatum is present at a concentration of at least 30%, and the ratio of (a) to (b) is from 7:3 to 1:3.

59. The skin barrier protective delivery system of any one of the preceding items, wherein the ratio of Coconut Alkanes to Coco-Caprylate/Caprate is from about from about 7:3 to about 1:3.

60. The skin barrier protective delivery system of any one of the preceding items, further containing at least two of a ceramide, a phytosterol, squalene, a plant-based esters or wax, and/or a phospholipid.

61. An emulsion comprising the skin barrier protective delivery system of any of the preceding items.

62. The skin barrier protective delivery system of any of the preceding items, that is sprayable.

63. The skin barrier protective delivery system of any of the preceding items having a viscosity of from about 500 cps to about 10,000 cps.

64. A skin barrier protective delivery system comprised of a mixture of Coconut Alkanes and Coco-Caprylate/Caprate at a concentration of at least 30%, and the ratio of Coconut Alkanes and Coco-Caprylate/Caprate is from 7:3 to 1:3.

65. A skin barrier protective delivery system consisting essentially of a mixture of Coconut Alkanes and Coco-Caprylate/Caprate and the ratio of Coconut Alkanes and Coco-Caprylate/Caprate is from 7:3 to 1:3.

66. The skin barrier protective delivery system of any one of the preceding items, wherein the ratio of Coconut Alkanes to Coco-Caprylate/Caprate is from about from about 7:3 to about 1:3.

67. The skin barrier protective delivery system of any one of the preceding items, further containing at least two of a ceramide, a phytosterol, squalene, a plant-based esters or wax, and/or a phospholipid.

68. An emulsion comprising the skin barrier protective delivery system of any of the preceding item.

69. The skin barrier protective delivery system of any one of the preceding items, that is sprayable.

70. The skin barrier protective delivery system of any one of the preceding items, having a viscosity of from about 500 cps to about 10,000 cps.

71. The skin barrier protective delivery system of any one of the preceding items, further comprising an active ingredient.

72. The skin barrier protective delivery system of any one of the preceding items, wherein the active ingredient is about 0.0001% to about 95% by weight.

73. The skin barrier protective delivery system of any one of the preceding items, wherein the active ingredient is selected from the group consisting of an antifungal agent, an antibacterial agent, an antiviral agent, an anti-acne agent, an antiaging agent, an anti-pruritic agent, a UV absorbing agent, a sunscreen agent, a skin pigment modulating agent, a skin lightening agent, a skin darkening agent, a hair growth enhancing agent, a hair growth inhibiting agent, an antidandruff agent, an anti-seborrheic agent, an anti-psoriasis agent, a hair removal agent, an exfoliating agent, a wound healing agent, an anti-inflammatory agent, a blood microcirculation improvement agent, a sebum modulating agent, a hormone, an immune modulating agent, a botanical extract, a moisturizing agent, an emollient, an astringent, an antiperspirant, a vitamin, a retinoid, a cleansing agent, a sensory agent, a color change agent, an antibiotic, an anti-irritant, an anesthetic, an analgesic, a steroid, a tissue healing agent, a tissue regenerating agent, a collagen or elastin boosting agent, a skin protectant agent, an agent to promote excess fat reduction or cellulite control or body toning benefits, an amino acid, a peptide, a mineral, a hydroxy acid, an anti-emetic agent, an anti-anginal agent, a bronchodilator agent, osteoporosis treatment agent, an anti-depressant agent, an anti-migraine agent, smoking cessation agent, anti-diarrheal agent, anti-ulcer agent, mood disorder agent, anti-obesity agents, erectile dysfunction control agents, anti-Parkinson agents, MAO inhibitors, sleep disorder agents, anti-diabetic agents, or combinations thereof.

74. The skin barrier protective delivery system of any one of the preceding items, further comprising a skin whitening agent selected from the group consisting of hydroquinone, arbutin, hydroquinone derivatives, Paper Mulberry extract (*Broussonetia kazinoke*), Mitracarpe extract (*Mitracarpus scaber*), Bearberry extract (*Arctostaphylos uva ursi*), Yellow Dock extract (*Rumex crispus* and *Rumex occidentalis*), Glutathione, Leucocyte extract, *Aspergillus orizae* extract (*Aspergillus orizae*), Licorice Root extract (*Glycyrrhiza glabra*), Rosmarinic acid (*Rosmarinus officinalis*), Tetrahydrocurcumin, Green Tea extract (*Camellia sinensis*), Yohimbe extract (*Pausinystalia yohimbe*), Ecklonia cava extract, niacinamide, Hydroxytetronic acid, *Spondias mombin* extract, *Maprounea guianensis* extract, *Walteria indica* extract, *Gouania blanchetiana* extract, *Cordia schomburgkii* extract, *Randia armata* extract, *Hibiscus furcellatus* extract, and combinations thereof.

75. The skin barrier protective delivery system of any one of the preceding items, further comprising an antioxidant selected from the group consisting of Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, Emblica extract, and combinations thereof.

76. The skin barrier protective delivery system of any one of the preceding items, further comprising a UVA/UVB sunscreen agent is selected from the group consisting of Titanium dioxide, Zinc oxide, Galanga extract (*Kaempferia galanga*), Benzophenone-3, Benzophenone-4, Ethylhexyl Methoxycinnamate, Homosalate, Ethylhexyl salicylate, Octocrylene, Menthyl anthranilate, Avobenzone, Lawsone, Sulisobenzone, Trolamine salicylate, Lawsone, Glyceryl aminobenzoate, Cinoxate, and PABA. and combinations thereof.

77. The skin barrier protective delivery system of any one of the preceding items, in a formulation selected from the group consisting of lotion, cream, gel, spray, thin liquid, body splash, mask, serum, solid cosmetic stick, lip balm, shampoo, liquid soap, bar soap, bath oil, cologne, hair conditioner, salve, collodion, impregnated patch, impregnated strip or skin surface implant.

78. The skin barrier protective delivery system of any one of the preceding items, further comprising a pharmaceutically acceptable carrier selected from the group consisting of water and oil emulsions, suspensions, colloids, microemulsions, clear solutions, suspensions of nanoparticles, emulsions of nanoparticles, and anhydrous compositions.

79. A skin barrier protective delivery system comprising: (i) at least 30 wt % Petrolatum; (ii) Coconut Alkanes in the range of 30-70 wt %; (iii) Coco-Caprylate/Caprate in the range of 3-7 wt %; (iv) ceramide NP in the range of 0.01-0.1 wt %; (v) ceramide AP in the range of 0.01-0.1 wt %; (vi) Jojoba Esters in the range of 0.1-1.5 wt %; (vii) Squalene in the range of 0.1-1 wt %; (viii) Phytosteryl Macadamiate in the range of 0.01-0.1 wt %; (ix) Phytosterols in the range of 0.005-0.1 wt %; (x) Tocopherol in the range of 0.001-0.1 wt %; (xi) C18-36 Acid Triglyceride in the range of 0.5-5 wt %; (xii) C12-18 Acid Triglyceride in the range of 0.1-1 wt %; (xiii) *Ipomoea batatas* root extract in the range of 0.01-0.1 wt %; (xiv) citric acid in the range of 0.001-0.01 wt %; (xv) *Acacia senegal* gum in the range of 0.001-0.1 wt %; and (xvi) Maltodextrin in the range of 0.001-0.1 wt %, wherein the delivery system is a spray formulation.

80. The skin barrier protective delivery system of any one of the preceding items, comprising: (i) 50 wt % Petrolatum; (ii) 42-43 wt % Coconut Alkanes; (iii) 4-5 wt % Coco-Caprylate/Caprate; (iv) 0.05 wt % ceramide NP; (v) 0.05 wt % ceramide AP; (vi) 0.75 wt % Jojoba Esters; (vii) 0.3-0.4 wt % Squalene; (viii) 0.05-0.06 wt % Phytosteryl Macadamiate; (ix) 0.01-0.02 wt % Phytosterols; (x) 0.0045 wt % Tocopherol; (xi) 1-2 wt % C18-36 Acid Triglyceride; (xii) 0.4-0.5 wt % C12-18 Acid Triglyceride; (xiii) 0.03-0.04 wt % *Ipomoea batatas* root extract; (xiv) 0.003-0.004 wt % citric acid; (xv) 0.03-0.04 wt % *Acacia senegal* gum; and (xvi) 0.03-0.04 wt % Maltodextrin.

81. The skin barrier protective delivery system of any one of the preceding items, having a viscosity of from about 500 cps to about 10,000 cps.

82. The skin barrier protective delivery system of any one of the preceding items, having a viscosity of from about 1,000 cps to about 5,000 cps.

83. The skin barrier protective delivery system of any one of the preceding items, further comprising an active ingredient.

84. The skin barrier protective delivery system of any one of the preceding items, wherein the active ingredient is about 0.0001% to about 70% by weight.

85. The skin barrier protective delivery system of any one of the preceding item wherein the active ingredient is selected from the group consisting of an antifungal agent, an antibacterial agent, an antiviral agent, an anti-acne agent, an antiaging agent, an anti-pruritic agent, a UV absorbing agent, a sunscreen agent, a skin pigment modulating agent, a skin lightening agent, a skin darkening agent, a hair growth enhancing agent, a hair growth inhibiting agent, an antidandruff agent, an anti-seborrheic agent, an anti-psoriasis agent, a hair removal agent, an exfoliating agent, a wound healing agent, an anti-inflammatory agent, a blood microcirculation improvement agent, a sebum modulating agent, a hormone, an immune modulating agent, a botanical extract, a moisturizing agent, an emollient, an astringent, an antiperspirant, a vitamin, a retinoid, a cleansing agent, a sensory agent, a color change agent, an antibiotic, an anti-irritant, an anesthetic, an analgesic, a steroid, a tissue healing agent, a tissue regenerating agent, a collagen or elastin boosting agent, a skin protectant agent, an agent to promote excess fat reduction or cellulite control or body toning benefits, an amino acid, a peptide, a mineral, a hydroxy acid, an anti-emetic agent, an anti-anginal agent, a bronchodilator agent, osteoporosis treatment agent, an anti-depressant agent, an anti-migraine agent, smoking cessation agent, anti-diarrheal agent, anti-ulcer agent, mood disorder agent, anti-obesity agents, erectile dysfunction control agents, anti-Parkinson agents, MAO inhibitors, sleep disorder agents, anti-diabetic agents, or combinations thereof.

86. The skin barrier protective delivery system of any one of the preceding items, further comprising a skin whitening agent selected from the group consisting of hydroquinone, arbutin, hydroquinone derivatives, Paper Mulberry extract (*Broussonetia kazinoke*), Mitracarpe extract (*Mitracarpus scaber*), Bearberry extract (*Arctostaphylos uva ursi*), Yellow Dock extract (*Rumex crispus* and *Rumex occidentalis*), Glutathione, Leucocyte extract, *Aspergillus orizae* extract (*Aspergillus orizae*), Licorice Root extract (*Glycyrrhiza glabra*), Rosmarinic acid (*Rosmarinus officinalis*), Tetrahydrocurcumin, Green Tea extract (*Camellia sinensis*), Yohimbe extract (*Pausinystalia yohimbe*), Ecklonia cava extract, niacinamide, Hydroxytetronic acid, *Spondias mombin* extract, *Maprounea guianensis* extract, *Walteria indica* extract, *Gouania blanchetiana* extract, *Cordia schomburgkii* extract, *Randia armata* extract, *Hibiscus furcellatus* extract, and combinations thereof.

87. The skin barrier protective delivery system of any one of the preceding items, further comprising an antioxidant selected from the group consisting of Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, Emblica extract, and combinations thereof.

88. The skin barrier protective delivery system of any one of the preceding items, further comprising a UVA/UVB sunscreen agent is selected from the group consisting of Titanium dioxide, Zinc oxide, Galanga extract (*Kaempferia galanga*), Benzophenone-3, Benzophenone-4, Ethylhexyl Methoxycinnamate, Homosalate, Ethylhexyl salicylate, Octocrylene, Menthyl anthranilate, Avobenzone, Lawsone, Sulisobenzone, Trolamine salicylate, Lawsone, Glyceryl aminobenzoate, Cinoxate, and PABA. and combinations thereof.

89. The skin barrier protective delivery system of any one of the preceding items, in a formulation selected from the group consisting of lotion, cream, gel, spray, thin liquid, body splash, mask, serum, solid cosmetic stick, lip balm, shampoo, liquid soap, bar soap, bath oil, cologne, hair conditioner, salve, collodion, impregnated patch, impregnated strip or skin surface implant.

90. The skin barrier protective delivery system of any one of the preceding items, further comprising a pharmaceutically acceptable carrier selected from the group consisting of water and oil emulsions, suspensions, colloids, microemulsions, clear solutions, suspensions of nanoparticles, emulsions of nanoparticles, and anhydrous compositions.

91. A method of making the skin barrier protective delivery system of claim 1, comprising: (a) mixing petrolatum, long chain alkanes and/or esters of long chain alcohols in a reactor to create a mixture; (b) heating the mixture until a melt is obtained; and (c) cooling the mixture.

92. A method of making the skin barrier protective delivery system of claim 1, comprising: (a) heating petrolatum in a reactor; (b) adding long chain alkanes and esters of long chain alcohols to the reactor to create a mixture; (c) heating the mixture until a melt is obtained; and (d) cooling the mixture.

The foregoing description of the specific embodiments will so fully reveal the general nature of the disclosure that others can, by applying knowledge within the skill of the relevant art(s) (including the contents of the documents cited and incorporated by reference herein), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure. Thus, the present disclosure should not be limited by any of the above-described exemplary embodiments but should be defined only in accordance with the following claims and their equivalents.

All references cited herein are incorporated herein by reference in their entirety and for all purposes to the same extent as if each individual publication or patent or patent application was specifically and individually indicated to be incorporated by reference in its entirety for all purposes.

The invention claimed is:

1. A skin barrier protective delivery system comprising: (i) a mixture of Coconut Alkanes at a concentration range of 30-70 wt % and Coco-Caprylate/Caprate at a concentration range of 3-7 wt %; and (ii) petrolatum, wherein the petrolatum is present at a concentration of at least 30 wt %, wherein the delivery system is sprayable and wherein the skin barrier protective delivery system further comprising each of the following components: ceramide NP, ceramide AP, jojoba esters, squalene, phytosterols, phytosteryl macadamiate, tocopherol, C18-C36 acid triglyceride, C12-18 acid triglyceride, *Ipomoea batatas* root extract, *Acacia senegal* gum, citric acid, and maltodextrin, wherein the C18-C36 acid triglyceride is different from the C12-18 acid triglyceride.

2. A skin barrier protective delivery system comprising: (i) a mixture of Coconut Alkanes at a concentration range of 30-70 wt % and Coco-Caprylate/Caprate at a concentration range of 3-7 wt %; and (ii) petrolatum, wherein the petrolatum is present at a concentration of at least 30 wt %, wherein the delivery system is sprayable and wherein the skin barrier protective delivery system comprises each of the following components:

(i) at least 30 wt % Petrolatum;
(ii) Coconut Alkanes in the range of 30-70 wt %;
(iii) Coco-Caprylate/Caprate in the range of 3-7 wt %;
(iv) ceramide NP in the range of 0.01-0.1 wt %;
(v) ceramide AP in the range of 0.01-0.1 wt %;
(vi) Jojoba Esters in the range of 0.1-1.5 wt %;
(vii) Squalene in the range of 0.1-1 wt %;
(viii) Phytosteryl Macadamiate in the range of 0.01-0.1 wt %;
(ix) Phytosterols in the range of 0.005-0.1 wt %;
(x) Tocopherol in the range of 0.001-0.1 wt %;
(xi) C18-36 Acid Triglyceride in the range of 0.5-5 wt %;
(xii) C12-18 Acid Triglyceride in the range of 0.1-1 wt %;
(xiii) *Ipomoea batatas* root extract in the range of 0.01-0.1 wt %;
(xiv) citric acid in the range of 0.001-0.01 wt %;
(xv) *Acacia senegal* gum in the range of 0.001-0.1 wt %; and
(xvi) Maltodextrin in the range of 0.001-0.1 wt %, wherein the delivery system is a sprayable formulation, and wherein the C18-C36 acid triglyceride is different from the C12-18 acid triglyceride.

3. A skin barrier protective delivery system comprising: (i) a mixture of Coconut Alkanes at a concentration range of 30-70 wt % and Coco-Caprylate/Caprate at a concentration range of 3-7 wt %; and (ii) petrolatum, wherein the petrolatum is present at a concentration of at least 30 wt %, wherein the delivery system is sprayable and wherein the ratio of the mixture of Coconut Alkanes and/or Coco-Caprylate/Caprate to Petrolatum is about 1:1 and wherein the skin barrier protective delivery system comprises each of the following components:

(i) 50 wt % Petrolatum;
(ii) 42-43 wt % Coconut Alkanes;
(iii) 4-5 wt % Coco-Caprylate/Caprate;
(iv) 0.05 wt % ceramide NP;
(v) 0.05 wt % ceramide AP;
(vi) 0.75 wt % Jojoba Esters;
(vii) 0.3-0.4 wt % Squalene;
(viii) 0.05-0.06 wt % Phytosteryl Macadamiate;
(ix) 0.01-0.02 wt % Phytosterols;
(x) 0.0045 wt % Tocopherol;
(xi) 1-2 wt % C18-36 Acid Triglyceride;
(xii) 0.4-0.5 wt % C12-18 Acid Triglyceride;
(xiii) 0.03-0.04 wt % *Ipomoea batatas* root extract;
(xiv) 0.003-0.004 wt % citric acid;
(xv) 0.03-0.04 wt % *Acacia senegal* gum; and
(xvi) 0.03-0.04 wt % Maltodextrin, wherein the C18-C36 acid triglyceride is different from the C12-18 acid triglyceride.

* * * * *